United States Patent
Barrett et al.

(10) Patent No.: US 10,733,476 B1
(45) Date of Patent: Aug. 4, 2020

(54) COMMUNICATION GENERATION USING SPARSE INDICATORS AND SENSOR DATA

(71) Applicant: Color Genomics, Inc., Burlingame, CA (US)

(72) Inventors: Ryan Barrett, San Francisco, CA (US); Nishant Bhat, San Francisco, CA (US); Huy Hong, Palo Alto, CA (US); Katsuya Noguchi, San Francisco, CA (US); Wendy McKennon, San Francisco, CA (US); Krishna Pant, San Jose, CA (US); Taylor Sittler, San Francisco, CA (US); Othman Laraki, Atherton, CA (US); Elad Gil, San Francisco, CA (US)

(73) Assignee: Color Genomics, Inc., Burlingame, CA (US)

( * ) Notice: Subject to any disclaimer, the term of this patent is extended or adjusted under 35 U.S.C. 154(b) by 119 days.

(21) Appl. No.: 15/683,495

(22) Filed: Aug. 22, 2017

Related U.S. Application Data

(63) Continuation-in-part of application No. 15/406,394, filed on Jan. 13, 2017, now Pat. No. 9,774,508, which is a continuation-in-part of application No. 15/169,294, filed on May 31, 2016, now Pat. No. 9,584,882, application No. 15/683,495, which is a continuation-in-part of application No. 15/489,473, filed on Apr. 17, 2017, now Pat. No. 9,773,031, application No. 15/683,495, which is a continuation-in-part of application No. 15/163,191, filed on May 24, 2016, now Pat. No. 9,785,792, application No. 15/683,495, which is a continuation-in-part of application No. 15/133,089, filed on Apr. 19, 2016, now Pat. No. 9,811,552.

(60) Provisional application No. 62/150,218, filed on Apr. 20, 2015, provisional application No. 62/261,982, filed on Dec. 2, 2015, provisional application No. 62/304,487, filed on Mar. 7, 2016, provisional application No. 62/324,080, filed on Apr. 18, 2016, provisional application No. 62/303,531, filed on Mar. 4, 2016, provisional application No. 62/274,660, filed on Jan. 4, 2016.

(51) Int. Cl.
*G06Q 10/00* (2012.01)
*G06K 9/62* (2006.01)
*G06K 9/00* (2006.01)

(52) U.S. Cl.
CPC ....... *G06K 9/6218* (2013.01); *G06K 9/00496* (2013.01); *G06K 9/6227* (2013.01)

(58) Field of Classification Search
CPC .. G06Q 10/00; G06Q 10/063; G06F 19/3418; G16H 10/60; G16B 50/00; H01L 21/768; H01L 21/76886; G06K 9/6218; G06K 9/00496; G06K 9/6227
See application file for complete search history.

(56) References Cited

U.S. PATENT DOCUMENTS

| 9,679,104 B2 * | 6/2017 | van Rooyen | H01L 21/76886 |
| 2014/0108074 A1 * | 4/2014 | Miller | G06Q 10/00 705/7.11 |
| 2015/0310182 A1 * | 10/2015 | Henze | G16H 10/60 705/3 |

* cited by examiner

*Primary Examiner* — Kyung H Shin
(74) *Attorney, Agent, or Firm* — Kilpatrick Townsend & Stockton LLP

(57) ABSTRACT

Techniques, systems, and products for analyzing sparse indicators and sensor data and generating communications are disclosed. The sensors may be associated with or incorporated into devices that may automatically relay sensor data for use in analyses and communication generation.

20 Claims, 20 Drawing Sheets

COMMUNICATION GENERATION USING SPARSE INDICATORS AND SENSOR DATA

CROSS-REFERENCE TO RELATED APPLICATIONS

This application is a continuation-in-part of U.S. application Ser. No. 15/406,394, filed Jan. 13, 2017, now U.S. Pat. No. 9,774,508, issued on Sep. 26, 2017. U.S. application Ser. No. 15/406,394 is a continuation-in-part of U.S. application Ser. No. 15/169,294, filed May 31, 2016, now U.S. Pat. No. 9,584,882, issued Feb. 28, 2017, which claims the benefit of and priority to U.S. Provisional Application No. 62/261,982, filed Dec. 2, 2015. U.S. application Ser. No. 15/406,394 also claims the benefit of and priority to U.S. Provisional Application No. 62/304,487, filed Mar. 7, 2016. This application is also a continuation-in-part of U.S. application Ser. No. 15/489,473, filed Apr. 17, 2017, now U.S. Pat. No. 9,773,031, issued on Sep. 26, 2017. U.S. application Ser. No. 15/489,473 claims the benefit of and priority to U.S. Provisional Application No. 62/324,080, filed Apr. 18, 2016. This application is also a continuation-in-part of U.S. application Ser. No. 15/163,191, filed May 24, 2016, now U.S. Pat. No. 9,785,792, issued on Oct. 10, 2017. U.S. application Ser. No. 15/163,191 claims the benefit of and priority to U.S. Provisional Application No. 62/303,531, filed Mar. 4, 2016. This application is also a continuation-in-part of U.S. application Ser. No. 15/133,089, filed Apr. 19, 2016, now U.S. Pat. No. 9,811,552, issued on Nov. 7, 2017. U.S. application Ser. No. 15/133,089 claims the benefit of and priority to U.S. Provisional Application No. 62/150,218, filed Apr. 20, 2015, and U.S. Provisional Application No. 62/274,660, filed Jan. 4, 2016. Each and all of the aforementioned applications are hereby incorporated by reference in their entireties for all purposes.

FIELD

Methods and systems disclosed herein relate generally to processing of data obtained from various sources for use in communication generation. Specifically, a sparse indicator can be analyzed and used in combination with sensor data to characterize states or status information, which in turn are used to generate communications.

BACKGROUND

Computational resources have become less expensive, and processing capabilities have become more sophisticated. In addition, sensors have proliferated, making sensor data more commonly available. Accordingly, the number and size of data sets has been exponentially increasing. It is therefore important to decide how to effectively and efficiently process these data sets. One approach is to use reference data sets and to selectively concentrate on how individual data sets differ from one or more reference data sets. By detecting these differences, a more compact representation of a data set is reached.

SUMMARY

Described herein are devices, systems, methods, and computer program products for facilitating generation of communications based on sparse indicator information and sensor data. In an aspect, systems for generating communications based on sparse indicator information and sensor data are provided. In some embodiments, a system comprises one or more hardware processors and a non-transitory computer readable storage medium in data communication with the one or more hardware processors, the non-transitory computer readable storage medium comprising instructions that, when executed by the one or more hardware processors, cause the one or more hardware processors to perform operations including receiving, at the one or more hardware processors, a first query from a first remote device, such as a first query that includes an electronic request to conduct a status analysis for a client determining an identifier associated with the client; querying a data store with the identifier to identify one or more sparse indicators associated with the client, such as where each sparse indicator corresponds to an instance of one or more values in the first data set differing from a corresponding one or more values in a reference data set; receiving, in response to the query, (such as by retrieving) the one or more sparse indicators associated with the client from the data store; performing a first status analysis using the one or more sparse indicators, such as a first status analysis that corresponds to determination of a first likelihood of the client transitioning to a particular state; obtaining sensor data associated with the client, such as sensor data providing an indication of a current quality of the client; performing a second status analysis using the one or more sparse indicators and the sensor data associated with the client, such as a second status analysis that corresponds to determination of a second likelihood of the client transitioning to the particular state; generating a communication indicative of the second likelihood of the client transitioning to the particular state; and transmitting the communication to the first remote device. Optionally, the instructions may be executed by the one or more hardware processors to perform methods described herein.

In another aspect, computer implemented methods for generating communications based on sparse indicator information and sensor data are provided. In one example embodiment, a method of this aspect comprises receiving, at one or more hardware processors, a first query from a first remote device, such as a first query that includes an electronic request to conduct a status analysis for a client; determining an identifier associated with the client; querying a data store with the identifier to identify one or more sparse indicators associated with the client, such as where each sparse indicator corresponds to an instance of one or more values in the first data set differing from a corresponding one or more values in a reference data set; receiving, in response to the query, the one or more sparse indicators associated with the client from the data store; performing a first status analysis using the one or more sparse indicators, such as a first status analysis that corresponds to determination of a first likelihood of the client transitioning to a particular state; obtaining sensor data associated with the client, such as sensor data providing an indication of a current quality of the client; performing a second status analysis using the one or more sparse indicators and the sensor data associated with the client, such as a second status analysis that corresponds to determination of a second likelihood of the client transitioning to the particular state; generating a communication indicative of the second likelihood of the client transitioning to the particular state; and transmitting the communication to the first remote device.

Optionally, methods of this aspect may further comprise generating a first communication indicative of the first likelihood of the client transitioning to the particular state; and transmitting the first communication to the first remote device. Optionally, methods of this aspect may further comprise identifying an aggregated likelihood of a plurality of other clients each transitioning to the particular state. Optionally, the communication includes the aggregated likelihood.

Optionally, methods of this aspect may further comprise generating one or more targets for the client, such as one or more targets that are associated with changing the second likelihood of the client transitioning to the particular state. Optionally, the communication includes the one or more targets. In some embodiments, methods of this aspect may further comprise receiving additional sensor data related to the one or more targets or providing an updated indication of an updated state of the client; performing a third status analysis using the one or more sparse indicators, the sensor data, and the additional sensor, such as a third status analysis that corresponds to determination of a third likelihood of the client transitioning to the particular state; generating a communication indicative of the third likelihood of the client transitioning to the particular state; and transmitting the second communication.

Optionally, methods of this aspect may further comprise transmitting a request for permission to access the one or more sparse indicators associated with the client; and receiving a response including authorization to access the one or more sparse indicators associated with the client. Optionally, querying the data store includes using the authorization, such as by transmitting an authorization code or key corresponding to the authorization.

In various embodiments, the sensor data includes one or more of chemical sensor data, potentiometric sensor data, solute sensor data, microfluidic sensor data, environmental sensor data, activity sensor data, accelerometer data, altitude sensor data, biometric sensor data, location sensor data, weather sensor data, biometric sensor data, biomarker sensor data, pH sensor data, cytometric sensor data, optical sensor data, smoke detector data, particulate sensor data, electrical current sensor data, electrical resistance sensor data, and electrical impedance sensor data. For example, in embodiments, the sensor data corresponds to sensor data obtained by one or more sensors associated with the client, such as attached to or worn by a client or located at a same location as the client. It will be appreciated that, in some embodiments, the sensor may be used to identify a biomarker of a client. It will be appreciated that, in some embodiments, sensor data corresponds to raw data signals obtained from one or more sensors. Optionally, sensor data may correspond to processed data derived from raw data signals obtained from one or more sensors.

In some embodiments, obtaining the sensor data includes transmitting a second query to a second remote device, such as a second query that includes a request for the sensor data associated with the client; and receiving, in response to the second query, the sensor data associated with the client. For example, the second remote device may be a cloud device or a server device. Optionally, the query may be associated with a permission or authorization code or key that provides access to the sensor data.

In another aspect, non-transitory computer readable storage mediums for generating communications based on sparse indicator information and sensor data are provided. In embodiments, the non-transitory computer readable storage medium comprises instructions that, when executed by one or more processors, cause the one or more processors to perform operations, such as aspects or steps of one or more methods disclosed herein. Optionally, the operations include receiving, at the one or more hardware processors, a first query from a first remote device, such as a first query that includes an electronic request to conduct a status analysis for a client; determining an identifier associated with the client; querying a data store with the identifier to identify one or more sparse indicators associated with the client, such as where each sparse indicator corresponds to an instance of one or more values in the first data set differing from a corresponding one or more values in a reference data set; receiving, in response to the query, the one or more sparse indicators associated with the client from the data store; performing a first status analysis using the one or more sparse indicators, such as a first status analysis that corresponds to determination of a first likelihood of the client transitioning to a particular state; obtaining sensor data associated with the client, such as sensor data providing an indication of a current quality of the client; performing a second status analysis using the one or more sparse indicators and the sensor data associated with the client, such as a second status analysis that corresponds to determination of a second likelihood of the client transitioning to the particular state; generating a communication indicative of the second likelihood of the client transitioning to the particular state; and transmitting the communication to the first remote device.

Some embodiments described herein relate to a process for processing requests to conduct disease-risk analyses, conducting using genetic information to generate risk variables for developing one or more diseases and/or for controlling access to genetic data.

In some embodiments, genetic data is analyzed in combination with data from one or more other sources. The other data could include data collected from a movement detector (e.g., phone accelerometer, Fitbit, or smart watch), data from a protected health information record (e.g., from a physician's office and/or including a test result), or camera data. A central or remote server may facilitate interactions between a user device and other device to authorize use of the other data. The integrated analysis of the various data types may result in generation of more accurate risk variables that represent a risk of developing a particular disease.

In some embodiments, a system may be configured to prioritize ensuring that clients are provided with evidence-based information prior to authorizing biological analyses and/or to enable clients to authorize post-hoc biological analyses. Accordingly, a graphical user interface may be generated and transmitted to a client device that identifies specific genetic data (e.g., genes) to be used in an analysis and may identify evidence supporting the purported pertinence. The interface may further be configured to accept a user input that authorizes access to and analysis of the specific genetic data. Because it is recognized that additional data may later as being additionally pertinent and/or identify some or all of the original data points as being pertinent to the risk in a different way, the interface may also be configured to accept (a same or different) input permitting post-hoc analysis (which may involve a new laboratory analysis of a stored sample).

In some embodiments, genetic data of clients are analyzed in a temporal manner that roughly corresponds to a time that the samples were received. Reports identifying risk variables generated based on the data, similarly, may be sent to client devices in this rough order. Upon identifying a new type of genetic data that pertains to the condition, all (or a set) of the samples can then be assessed in a near-batch mode. This updated analysis may involve new laboratory analysis of stored samples or a retrieval of data previously collected but not necessarily used. Updated reports may then be sent to client devices in a conditional or unconditional manner. For example, updated reports may be transmitted to a device of each client for which an updated analysis was performed or to a device of each client for which an updated analysis yielded a particular type of result (e.g., a changed result). Post-hoc analysis may pertain to a same condition, a different condition or a treatment efficacy.

In some embodiments, a data store may store, for each of one or more subjects, part or all of a subject's genome. An app developer may request access to part or all of the data, but access constraints may be established to ensure that a subject has authorized such access and potentially that such authorization is reasonable. For example, it may be required that a developer have presented indications as to which data is being requested and/or why to a user and that a user have provided input authorizing the request. As another example, it may be required that all of a developer's requested data be informative (e.g., as supported based on industry knowledge or developer data) of a condition being genetically assessed.

In some embodiments, an app developer may request access to part or all of the data. Such data access may present privacy concerns above and beyond normal data, as it can relate to a subject's health and may be subject to HIPAA. Access restrictions can therefore be accordingly established. The restrictions may be established in a manner that allows differential types of access to data to be granted based on a permission type granted by a subject. For example, a first permission type may grant access to genetic data along with other data (e.g., including a subject's name, past diagnoses, activity patterns, etc.), while a second type may permit access to the genetic data but restrict or deny access to the other data.

In some embodiments, interfaces may be provided to allow developers to specify particular genetic and/or epigenetic data of interest. An interface may identify (for example) what types of data (e.g., what gene sequences) may be available (e.g., for at least one client) or that are available for a given client. Thus, for example, one or more inputs may be collected to identify a client and one or more genes of interest. Further, a developer may be able to specify, via an interface, a type of requested data (e.g., a sequence, variance detection and/or categorization). The request can then be processed to ensure that the data is available and that the developer is authorized to access the data. The authorization check may include sending an email to a client requesting an indication as to whether authorization is being provided.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

Illustrative embodiments of the present invention are described in detail below with reference to the following drawing figures.

DETAILED DESCRIPTION

Figure 1:
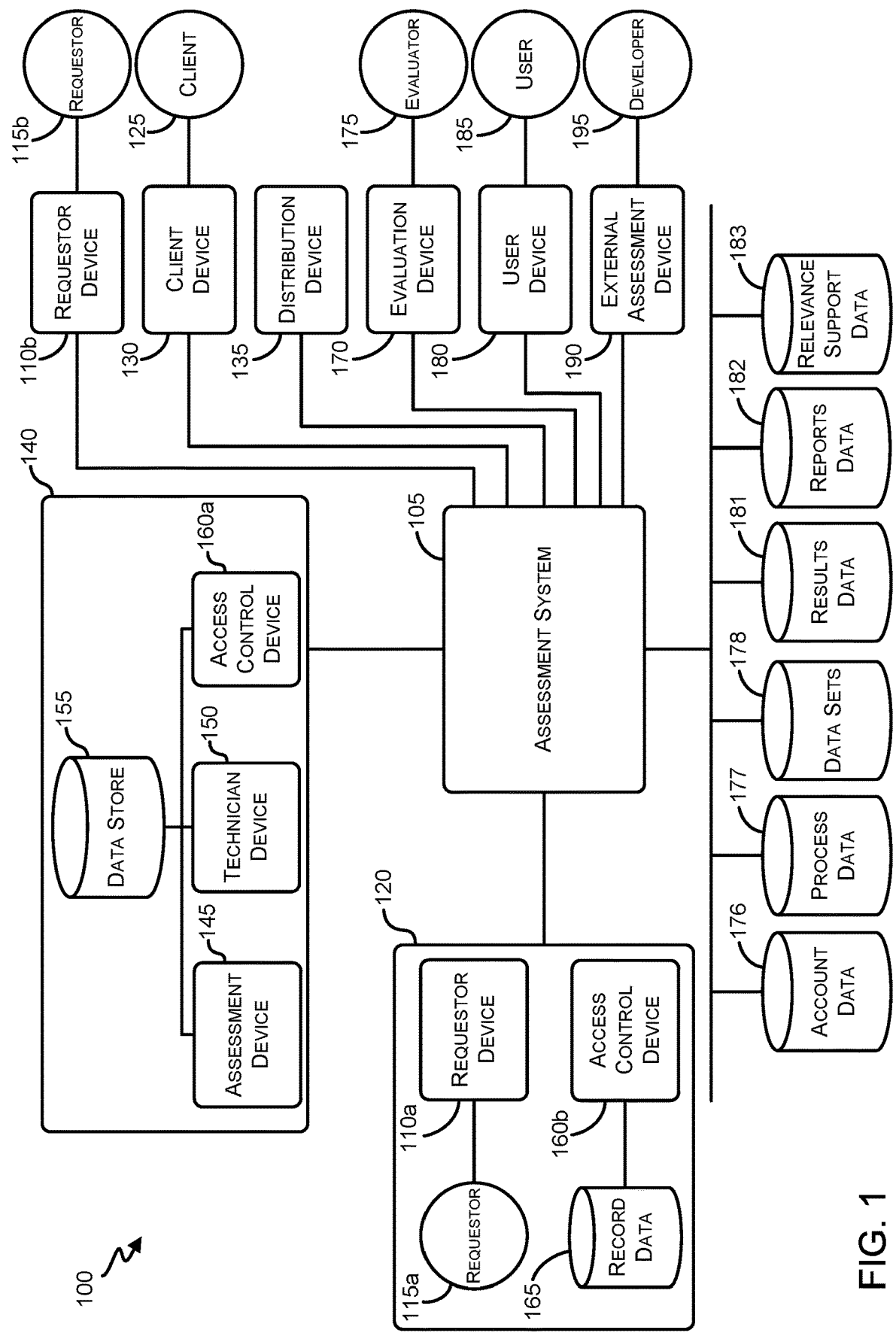
FIG. 1 shows a representation of a data processing network, in accordance with some embodiments.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail.

In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

In general the terms and phrases used herein have their art-recognized meaning, which can be found by reference to standard texts, journal references and contexts known to those skilled in the art. The following definitions are provided to clarify their specific use in the context of the invention.

The term "machine-readable storage medium" or "computer-readable storage medium" includes, but is not limited to, portable or non-portable storage devices, optical storage devices, and various other mediums capable of storing, containing, or carrying instruction(s) and/or data. A machine-readable storage medium or computer-readable storage medium may include a non-transitory medium in which data may be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, data store writes/reads, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a machine-readable medium. A processor(s) may perform the necessary tasks.

Systems depicted in some of the figures may be provided in various configurations. In some embodiments, the systems may be configured as a distributed system where one or more components of the system are distributed across one or more networks in a cloud computing system.

Figure 2:
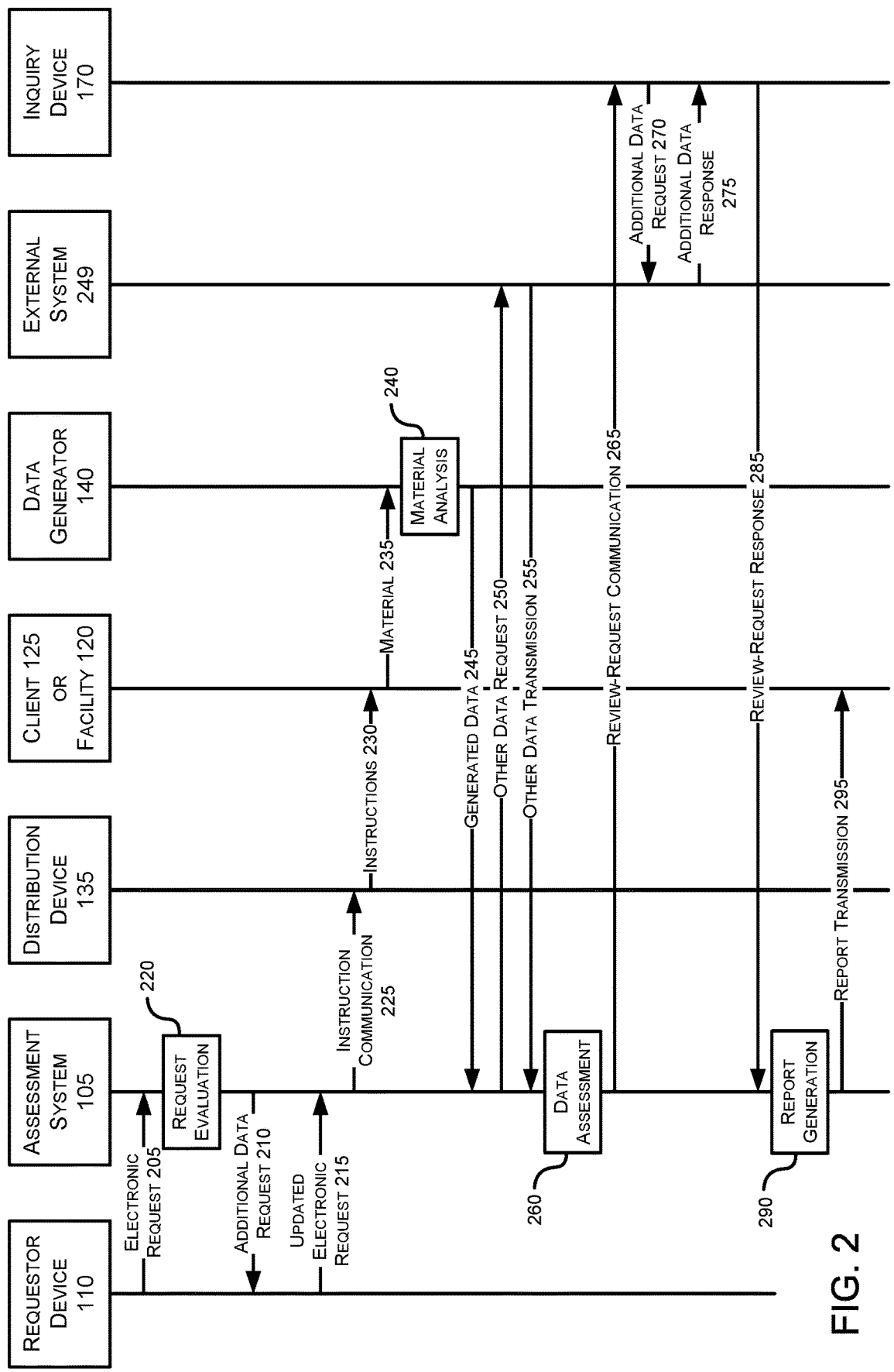
FIG. 2 shows a communication exchange between systems and devices of a data processing network, in accordance with some embodiments.

FIG. 1 shows a representation of an assessment network 100. In addition, FIG. 2 illustrates interactions between various systems or components of assessment network 100 to illustrate the flows of data and materials, for example.

Assessment system 105 may, for example, receive an electronic request 205 from a requestor device 110. Assessment system 105 may include one or more electronic devices (e.g., storage devices, servers, and/or computers) and may, but not need, reside partly or entirely at a remote server. Requestor device 110 may be configured and located to receive input from a requestor 115. In one instance, requestor device 110a is located in an external facility 120. In one instance, requestor device 110b includes an internally linked requestor device 110b, such as one that itself receives invitations, such as from assessment system 105, to generate electronic requests.

Request 205 may include instructions to conduct a dataset analysis, for example. Optionally, request 205 may be encrypted prior to transmission; such an electronic request may be decrypted upon receipt. Request 205 may identify, or otherwise indicate, one or more states to be evaluated during the analysis and/or during an assessment. Request 205 may identify a client and/or include additional data pertaining to the client, such as client-identifying data.

The client may be equated to, by assessment system 105, a client device 130. In some instances, a client device 130, associated with client 125, initially transmits a preliminary electronic request for the analysis and/or assessment to assessment system 105. For example, such a preliminary electronic request may be initiated via interaction with a website associated with assessment system 105. The same or a subsequent preliminary request may identify a particular requestor (e.g., by name, office location, phone number, and/or email address) and/or may request that a requestor 115b associated with an internally linked requestor device 110b submit such a request.

When a particular entity is identified in a preliminary electronic request, assessment system 105 may identify a destination address (e.g., IP address or email address) associated with the entity and transmit a communication identifying information associated with the preliminary request (e.g., the client, a type of analysis, and so on). The communication may include a partial instruction and/or an input field that would confirm that the request of the client 125 is to be generated and transmitted back to assessment system 105. Such a communication may facilitate receipt of the electronic request 205 from requestor device 110b.

When it is requested that a requestor 115b associated with an internally linked requestor device 110b submit such a request, assessment system 105 may transmit a similar communication to a requestor device 110b that may have been selected from among multiple internally linked requestor devices. The selection may be based on a load balancing technique, availability hours, expertise, locations of the multiple requestor devices, a pseudo-random selection technique, and/or an entity affiliation.

Once request 205 has been received from a requestor device 110 (e.g., in response to a preliminary request from a client device 130), assessment system 105 may evaluate, such as at block 220, the request 205 to ensure that all required data has been provided and that all required data pertaining to client 125 has been identified (e.g., via the request, a preliminary request and/or stored data). If assessment system 105 determines that all required information has not been identified, a request 210 for such information may be transmitted to requestor device 110 and/or client device 130. The request 205 may be updated with this information and an updated electronic request 215 may be transmitted to assessment system 105. In various instances, an object provided to a user depends on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided, assessment system 105 may send an instruction communication 225 to a distribution device 135. Optionally, communication 225 may be encrypted prior to transmission; such an encrypted communication may be decrypted upon receipt. Optionally, communication 225 may be transmitted using communications system 108 and/or over one or more network links, such as including transmission, at least in part, over a public communications network, such as the Internet. Communication 225 may include, for example, a name and address of client 125 and, in some instances, an indication as to what is to be provided to client 125 for collection of a material for subsequent analysis. For example, a request 205 may indicate a type of analysis that is to be performed on a material (e.g., an analysis pertaining to a likelihood of getting one or more particular types of states) and/or a type of material (e.g., type of sample) that is to be analyzed. Communication 225 may identify the type of analysis, type of material, and/or kit associated with collection of the material. The communication 225 may thus facilitate and/or trigger a physical distribution of instructions 230, which may include a kit or other sample collection materials, to a client address. The instructions 230 may include, for example, instructions as to how to collect a material, a container for storing the material and/or information pertaining to an instruction or type of analysis to be conducted. Alternatively, the instructions 230 may be provided to a facility 120, such as may be associated with a requestor 115a, who may aid client 125 in obtaining the material.

A material 235 from client 125 may then be directed to and received at a data generator 140 for analysis 240. Data generator 140 may be, for example, part of a facility. Data generator 140 may include one or more assessment devices 145 configured to generate data reads, data elements, or data sets for various data-set units using the material 235 as part of analysis 240. For example, an assessment device 145 may include a data-characterizer device (e.g., sequencer and/or polymerase chain reaction machine). Data generator 140 may further include one or more devices 150, such as a desktop or laptop computer. Generated data 245 generated by or at one or more devices (e.g., assessment device 145 or technician device 150) may be stored at a data store 155, which may be remote from all data generator devices or part of a data generator device. The data 245 may, for example, include identifying client information (e.g., a name and address), facility information (e.g., location and name), device specifications (e.g., manufacturer and model of assessment device) and data. In some embodiments, a facility, such as facility 120 or data generator 140, may correspond to a lab.

In some instances, data is optionally collected or requested from one or more external systems 249. Thus, assessment system 105 may transmit one or more other data requests 250 and one or more other data transmissions 255 may provide the other data. For example, one or more data sets and/or one or more processed versions thereof (e.g., identifying one or more sparse indicators) corresponding to an existing or new client may be received from an external system 249, As another example, assessment system 105 may transmit a client data set to an external system 249, and external system 249 may then return a result of an assessment of the client data set. As yet another example, other data may include a data set (or results based on such data) corresponding to another individual (e.g., an entity related to a client and/or an entity sharing a characteristic with a client). The other individual may be, for example, identified based on input from the client and/or automatically identified (e.g., based on a query of a data store to identify clients associated with inputs or results indicating a shared characteristic or relationship). In some instances, a state assessment variable may be generated based on data from multiple other people, and the data for each other person may be weighted based on (for example) how closely related the person is with a client and/or how many or which characteristics the person shares with a client.

An access control device 160a may control which devices and/or entities may gain access to the data 245, which may apply to devices and/or entities internal to data generator 140 and/or to devices and/or entities external to data generator 140. Access control device 160a may implement one or more rules, such as restricting access to client data to one or more particular devices (e.g., associated with assessment system 105). Such access may further or alternatively be controlled via logins, passwords, device identifier verification, etc.

In various instances, access control device 160a controls access via control of pushed transmissions and/or via control of processing pull requests. For example, a rule may indicate that data 245 pertaining to a material, such as a sample, is to automatically be transmitted to a particular assessment system 105 (and/or device associated therewith) upon completion of a facility-based assessment or detection of particular data (e.g., data matching a request). Access control device 160a may then monitor for such a criterion to be met and may then generate and transmit appropriate data.

Data 245 may include a plurality of data reads, data elements, or sets (e.g., each data read in the plurality of data reads corresponding to a same client, or at least some of the plurality of data reads corresponding to different clients). In various instances, data 245 may be transmitted to assessment system 105 in a batch-mode, in a streaming mode, in real-time as data is produced, and/or upon request. Data 245 may also be stored at a data store local or remote to data generator 140. A given transmission or stream may include data that corresponds to a single, or in other instances to multiple, client, sample, and/or data reads. In some instances, access control device 160a evaluates one or more transmission conditions, which may indicate, for example, whether and/or what data is to be transmitted given a quantity of data collected (e.g., generally, since a past transmission and/or for a given client or sample) and/or given a time since a previous transmission. In one instance, as data reads are generated by an assessment device, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 105. In one instance, the data may then be appended to a stream that is being fed to assessment system 105.

It will be appreciated that assessment network 100 may, in some instances, include multiple data generators 140, each of which may include an assessment device 145, technician device and/or access control device 160*a*. Further, a given data generator 140 may, in some instances, include multiple assessment devices 145, multiple technician devices 150 and/or multiple access control devices 160*a*. Thus, data 245 received at assessment system 105 may include data collected by and/or derived from data collected by different assessment devices, which may result in the data having different biases, units, and/or representation. Similarly, personnel operating different technician devices 150 may utilize different protocols and/or data interpretation techniques, which may again result in receipt of data at assessment system 105 that has different biases, units, variables, and so on. Further, even data originating from a same device may, in time, exhibit different biases, units, and so on, which may be a result of a manipulation of a control of the device and/or equipment wear.

Thus, in some instances, assessment system 105 performs a comparison across data 245 received from a data generator device (e.g., an access control device 160*a* or directly from an assessment device 145 or technician device 150) associated with data generator 140. The comparison may be across, for example, data collected at different facilities, data based on measurements collected at different devices, and/or data collected at different times. It will be appreciated that the comparison may include a direct comparison of collected data or comparing preprocessed versions of the collected data. For example, received data may first be preprocessed via a transformation and/or dimensionality-reduction technique, such as principal component analysis, independent component analysis, or canonical correspondence analysis.

The comparison may include, for example, performing a clustering technique so as to detect whether data corresponding to a given facility, device, or time period predominately resides in a different cluster than data corresponding to one or more other facilities, devices, or time periods. The clustering technique may include, for example, a connectivity based clustering technique, a centroid-based clustering technique (e.g., such as one using k-means clustering), a distribution-based clustering technique, or a density-based clustering technique.

The comparison may additionally or alternatively include a statistical technique, such as one that employs a statistical test to determine whether two or more data sets (e.g., corresponding to different facilities, devices, or time periods) are statistically different. For example, a Chi-square, t-test or ANOVA may be used.

The comparison may additionally or alternatively include a time-series analysis. For example, a regression technique may be used to determine whether output from a given device is gradually changing in time.

When it is determined that particular data corresponding to a given facility, device, or time period is different than data corresponding to one or more other facilities, devices, or time periods (e.g., is assigned to a different cluster than other data or is associated with a p-value below a threshold), a normalization and/or conversion factor may further be identified. For example, a normalization and/or conversion factor may be identified based on centroids of data clusters and/or inter-cluster distances. As another example, a linear or non-linear function may be derived to relate data from a given facility, device, or time period to other data.

In some instances, a determination that particular data corresponding to a given facility, device, or time period is different than data corresponding to one or more other facilities, devices, or time periods may indicate that data from the given facility, device, or time period is not to be used. In such instances, an instruction communication may be sent to a facility to reprocess a material, such as a sample.

In addition to receiving data 245, assessment system 105 may further collect one or more other data that may be used to assess, for example, a likelihood for transitioning into a particular state. For example, one type of other data may include inputs provided at a client device 130, such as inputs that indicate past-state data and/or current-state data, familial-state data and statuses, age, occupation, activity patterns, association with environments having particular characteristics, and so on. The other data may be received by way of one or more other data transmissions 255 from external system 249. Optionally, other data transmission 255 may be encrypted prior to transmission; such an encrypted transmission may be decrypted upon receipt. Optionally, other data transmission 255 may be transmitted over one or more network links, such as including transmission, at least in part, over a public communications network, such as the Internet. Optionally, other data transmission 255 may be transmitted over at least a portion of communications system 108.

Another type of other data may include data automatically detected at a client device 130 or a location associated with the client. For example, a wearable client device may track activity patterns so as to estimate calories burned per day, or the wearable client device may estimate a pulse distribution, client temperature, sleep patterns and/or indoor/outdoor time. This data obtained directly by client device 130 may be directly transmitted (e.g., after request 250 and/or authorization handshake) to assessment system 105 and/or via another client device (e.g., via accessing health-data on a phone or computer device). Optionally, other data obtained directly by client device 130 may be transmitted over one or more network links, such as including transmission, at least in part, over a public communications network, such as the Internet. Optionally, other data obtained directly by client device 130 may be transmitted over at least a portion of a communication system. Optionally, other data obtained directly by client device 130 may be part of other data transmission 255.

Optionally, other data may correspond to data obtained by one or more sensors associated with a client or with a location associated with the client. For example, useful sensor data includes, but is not limited to, chemical sensor data, potentiometric sensor data, solute sensor data, microfluidic sensor data, environmental sensor data, activity sensor data, accelerometer data, altitude sensor data, biometric sensor data, location sensor data, weather sensor data, biometric sensor data, biomarker sensor data, pH sensor data, cytometric sensor data, optical sensor data, smoke detector data, particulate sensor data, electrical current sensor data, electrical resistance sensor data, and electrical impedance sensor data. The use of sensor data may be beneficial and advantageous as the sensors can directly monitor behaviors, actions, states, qualities, client characteristics, environmental characteristics, etc., without necessarily requiring inputs or actions to be taken by the client to obtain the sensor data. In this way, other data can be obtained with limited client interaction.

Yet another type of other data may include record data, which may be stored, for example, at a record data store 165 at and/or associated with an external facility, such as one having provided an electronic request to perform an analysis or assessment pertaining to a client and/or one as identified via input at a client device 130. To illustrate, the other data may identify one or more client reported experiences and/or evaluation results for a client or may include a result of one or more tests.

In some instances, other data may include data pertaining to a different client. For example, it may be determined or estimated that a given client is related to another client. Such determination or estimation may be based on inputs detected at a client device identifying one or more family members (e.g., by name), and a data store may be queried to determine whether any clients match any of the family member identifications. Such relationship determination or estimation may alternatively or additionally be based on a data set analysis, such that a raw or processed data set from the given client is compared to a raw or processed data set from some or all other clients to identify, for example, whether any other clients share a threshold portion of a data set with the client. Upon detecting an above-threshold match, a percentage of value matching may be used to estimate a type of relationship between the clients. Upon identifying a related client, other data corresponding to the related client may be identified. For example, the other data may include a past or current state or quality of the related client. The other data may be identified (for example) based on an input provided by the client or the related client or record data associated with the related client.

Thus, assessment system 105 may have access to, for a given client, one or more data sets, data set availability modification data, client-reported data, record data, test data, activity data, and/or other types of data. These data may be detected, assessed, or otherwise evaluated, at block 260, such as in one or more assessment processes. Data sets may be evaluated to detect and assess sparse indicators, for example, as described below in further detail. The detection and/or assessment at block 260 may be performed, for example, partly or fully at assessment system 105. In some instances, the detection and/or assessment at block 260 is performed in a partly or fully automated manner. In some instances, the detection and/or assessment at block 260 involves processing of inputs provided by a reviewer or evaluator.

Generation of a report, at block 290, may be performed using the results of data assessment of block 260. A report transmission 295 may include the report and be transmitted to client 125 or facility 120, such as by way of client device 130 or requestor device 110a.

Figure 3:
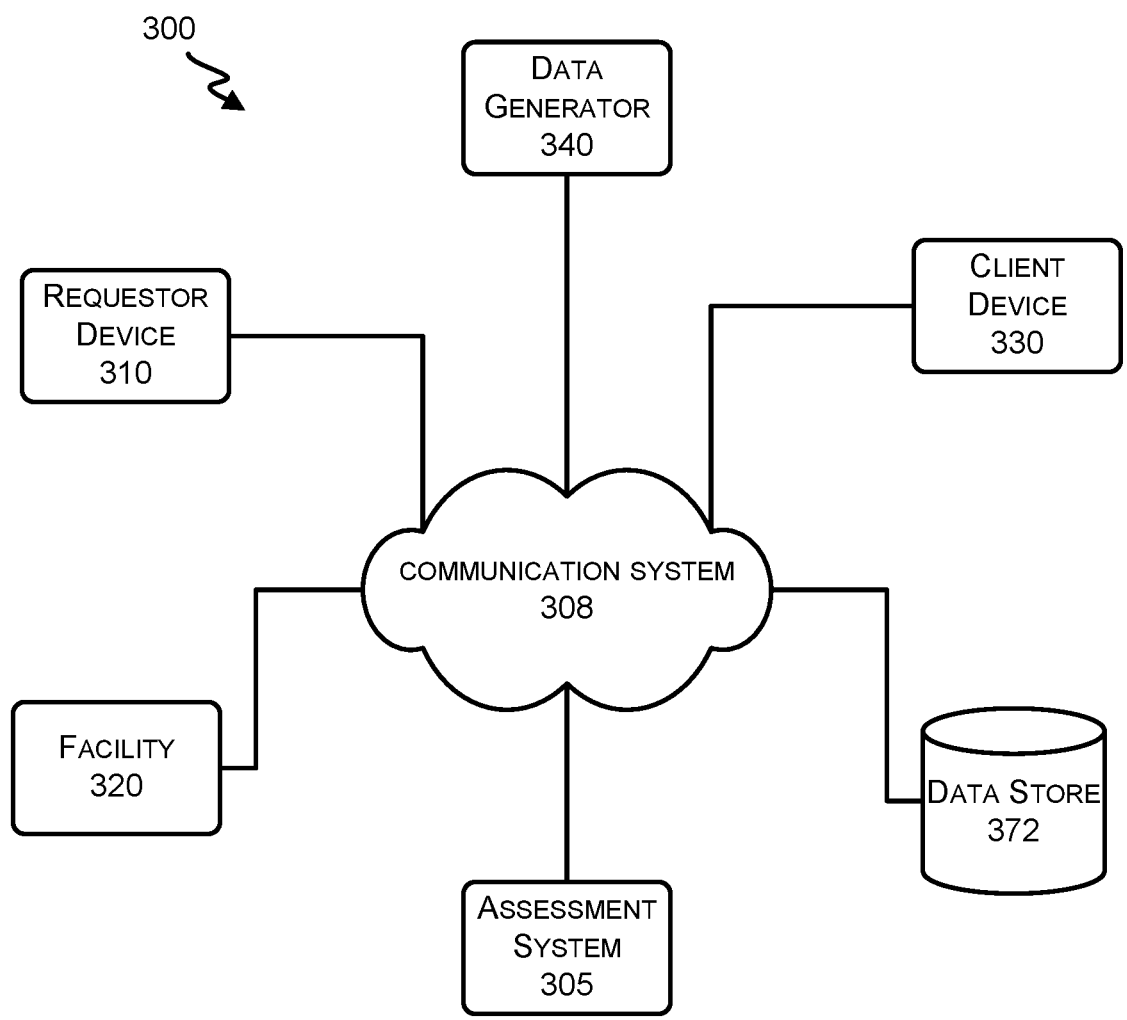
FIG. 3 shows a representation of an example communication network, in accordance with some embodiments.

Referring next to FIG. 3, an assessment network 300 is shown in one embodiment. Assessment network 300 may, but need not, correspond to assessment network 100 shown in FIG. 1. Through the interaction of multiple devices and entities, an assessment system 305 may receive data sets corresponding to individual clients. As illustrated, assessment system 305 may connect, via communication system 308, to each of one or more other systems or devices. Assessment network 300 may also include additional systems or devices, as illustrated in FIG. 3. For example, assessment network 300 may include requestor device 310, facility 320, client device 330, data generator 340, and data store 372, in addition to other systems or devices not explicitly depicted in FIG. 3.

Data may be exchanged between various systems or devices of assessment network, such as by way of communication system 308. Communication system 308 may, for example, include one or more data communication systems or networks, such as a wired or wireless data connection that makes use of or is compliant with one or more Institute of Electrical and Electronics Engineers (IEEE) networking standards, such as 802.3 (Ethernet), 802.11 (Wi-Fi), or 802.16 (WiMAX), or other data communications standards such as IEEE 1394 (FireWire), Bluetooth, Universal Serial Bus (USB), Serial ATA (SATA), Parallel ATA (PATA), Thunderbolt, Fibre Channel, Small Computer System Interface (SCSI), GSM, LTE, etc. Communication system 308 may include one or more TCP/IP compliant interconnections, such as may be present on a private or public communications network, such as the Internet. Communication system 308 may further include servers, systems, and storage devices in the cloud. Communication system 308 may represent or include one or more intermediate systems or data connections between various other components of assessment network 300. Additionally, communication system 308 may represent a direct connection between various other components of assessment network 300, such as a direct connection between assessment system 305 and data store 372, which may optionally allow for communication with data store 372 by other components of assessment network 300 only by way of assessment system 305, for example. It will be appreciated that data store 372 may include one or more data stores, which may optionally be linked or otherwise configured or organized to allow for efficient retrieval and storage of data by reference to different entries in particular data stores or data tables. For example, data store 372 may comprise a relational database or data store, in some embodiments.

One or more of the devices or systems of assessment network 300 may be present at a single location or each may be present at various different locations and be in data communication with one another via communication system 308, depending on the specific configuration. For example, facility 320 and data generator 340 may be at a same location. Requestor device 310 may further be present at facility 320, such as if possessed by a requestor personnel, for example. Similarly, client device 330 may also be present at data generator 340 or facility 320, such as if possessed by a client, for example. In some embodiments, one or more devices or systems of assessment network 300 may be mobile devices, such as a smartphone, tablet computer, laptop, or other compact device, which may facilitate transport between locations or with a user or client. Use of mobile devices may, for example, be advantageous for allowing input to be entered in real-time and/or on request from any location in order to facilitate expedient processing and/or analysis of data or generation of state assessments.

In one instance, assessment system 305 receives a request communication (e.g., via communication system) from a requestor device 310 that identifies a client. Client identifying authentication and/or other information can be received from a client device (e.g., which, in some instances, is also requestor device 310). Assessment system 305 may then prime data generator 340 to detect a material associated with the client and generate a set of reads based thereupon.

Assessment system 305 may process the reads by, for example, aligning individual reads to a reference data set (e.g., reference genome) and generating one or more client data sets. For example, a first client data set may include an identifier data set (e.g., a sequence) that identifies a base at each of a set of positions, such at each position along one or more data-set units (e.g., genes). The identifier data set may be generated by, for example, identifying a set of identifiers as those present in the reads aligned to a given position, at the position, and detecting a most common identifier from amongst the set of identifiers. A second client data set may include a coverage data set that identifies, for each position of a set of positions (e.g., at each position along one or more data-set units) a number of reads aligned to overlap with the position. Assessment system 305 may detect one or more differences (e.g., variants) using the data set(s). For example, a difference may be identified by detecting a difference, at a given position, between a value of the identifier data set and a corresponding value of the reference data set. As another example, a difference may be identified by detecting an abrupt change in a coverage data set (e.g., such that values abruptly change approximately 2- or 3-fold). A sparse indicator may be defined for each difference so as to identify a type of difference observed (e.g., what identifier was present in an identifier data set as opposed to a reference data set or how a coverage data set changed) and a position (e.g., with respect to the reference data set and/or along one or more data-set units) at which the difference was observed.

Each sparse indicator may be assigned to a bucket, which may reflect a predicted impact of the detected difference. In some instances, a set of buckets are defined. Each of one, more or all of the buckets may correspond to a predicted likelihood that a client will progress to a given state. A state may include, for example, utilizing a full memory bank, a condition (e.g., cancer), a quality (e.g., a feature, characteristic, or condition), reduced bandwidth, and/or a connection drop. Thus, buckets may reflect whether and/or a degree to which a difference causes the state (e.g., reflecting memory requirements, whether the difference is (e.g., and/or is likely to be) pathogenic or benign), consumes bandwidth, and/or impairs a connection's stability. For each client, a determination as to how many sparse indicators were assigned to one or more particular buckets may be used to generate a result that identifies a state-progression prediction. The result may be transmitted to requestor device 310 and/or client device 330.

Reads, data sets, sparse indicators, bucket assignments and/or results may be stored (e.g., in association with corresponding client identifiers) in one or more data stores. In some instances, data may be subsequently retrieved for performing an updated assessment (e.g., using a new bucketing protocol or result-generation technique), performing a different type of assessment and/or transmitting data to another device.

Figure 4:
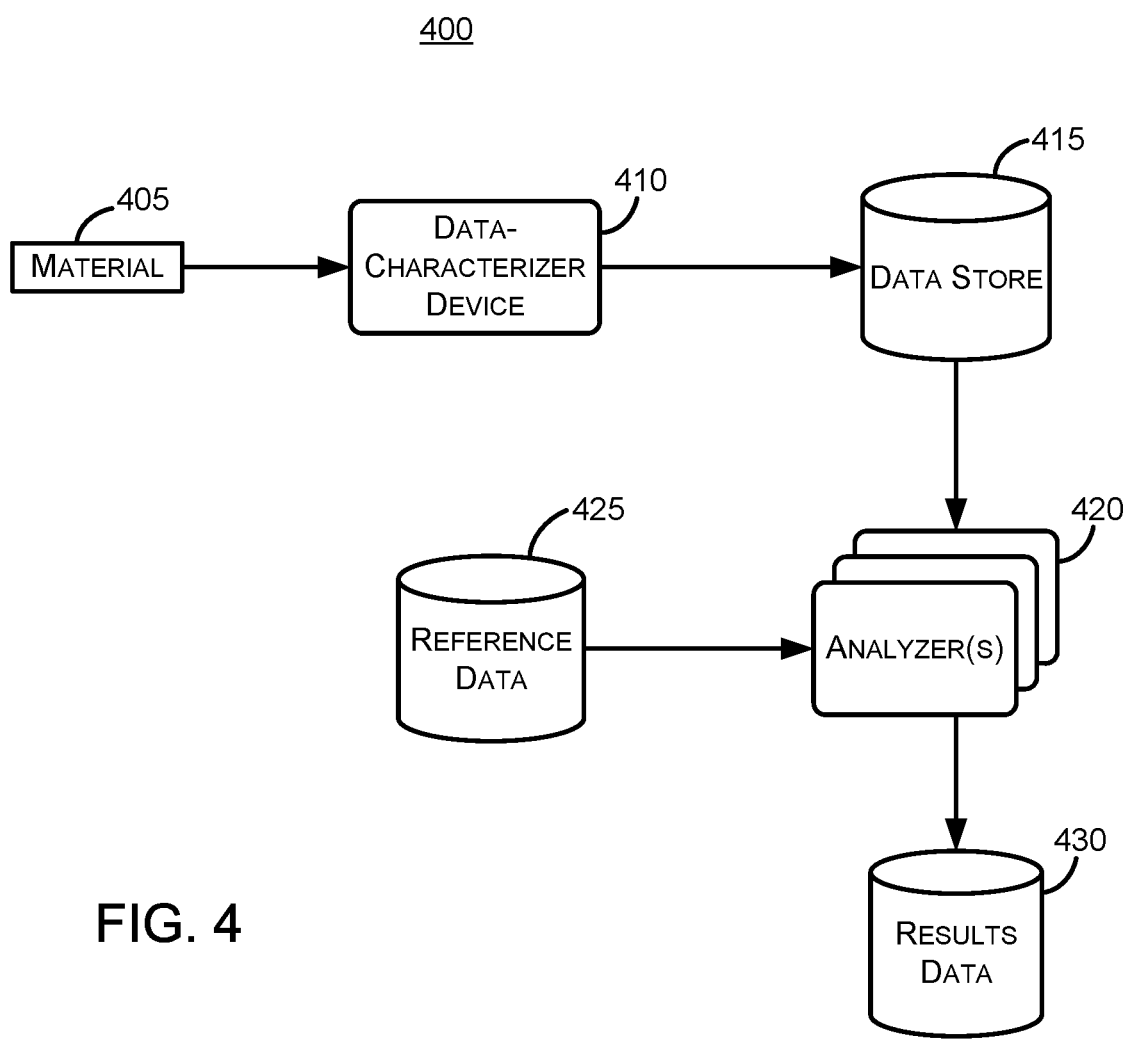
FIG. 4 shows a process flow, in accordance with some embodiments.

Turning next to FIG. 4, a process flow embodiment 400 is shown. Initially, a test material 405 is obtained from a client. As described above, the material 405 may be obtained directly by the client using a collection kit. A client may be able to obtain the material themselves, particularly if the material is easy to collect. Alternatively or additionally, material 405 is obtained at a facility. Obtaining material 405 at a facility may be useful if the material is more difficult to obtain, or if chain-of-custody is a concern.

Material 405 is assessed by a data-characterizer device 410, which may generate a plurality of data sets, including coverage data sets and identifier data sets. As the data sets are determined, they may be stored in data store 415 for subsequent analysis.

Data-characterizer device 410 and data store 415 may be located at a same location, such as a facility. Alternatively, data-characterizer device 410 and data store 415 may be remote from one another. In such a configuration, transmission of data sets from data-characterizer device 410 to data store 415 may occur using any of a variety of data communication standards and/or protocols. In one example, data sets are transmitted from data-characterizer device 410 over a wired and/or wireless network to reach data store 415. In another example, data sets are stored by data-characterizer device 410 directly to a storage medium, such as a flash drive or hard drive, which may be used to facilitate relaying data sets to remote data store 415. Optionally, data store 415 may comprise the storage medium. Data sets stored in data store 415 may be analyzed by data set analyzer 420. Data set analyzer 420 may be located at a same or different location from data-characterizer device 410 and/or data store 415.

Depending on the particular configuration, data sets generated by data-characterizer device 410 and/or stored in data store 415 may be analyzed individually, in real-time as the data sets are produced, or in batches, such as upon completion of a plurality of data sets. Data set analyzer 420 may utilize reference data stored in reference data store 425 in analysis of the data sets generated by data-characterizer device 410 and/or stored in data store 415.

A variety of analyses may be performed on the data sets by data set analyzers 420. For example, data set analyzer 420 may align each read in a data set to a portion of one or more reference sets. Data set analyzer 420 may also generate coverage data and/or identifier data using reads from the data set. Upon completion of the analysis, the information corresponding to the data sets (e.g., coverage data and/or identifier data) and/or alignment indications may be transmitted to and/or stored in one or more results data stores 430, which may correspond to a portion of data store 372.

It will be appreciated that data set analysis may be resource intensive, and thus a plurality of data set analyzers 420 may be used during the analysis process to distribute the resource burden, for example, and/or increase the rate at which data sets may be analyzed. For example, if a plurality of alignments are to be evaluated, such as by determining a potential alignment of an individual data set against multiple reference data sets, it may be desirable to distribute the tasks among multiple data set analyzers 420. Load balancing between a plurality of data set analyzers 420 may be performed to further enhance the use of resources, for example. Additionally, it may be desirable to compare the data sets stored in data store 415 against multiple reference data sets, such as from related family members or from people sharing one or more characteristics, as described above, and comparisons of the data sets with different reference data sets may be performed by different data set analyzers.

Additionally or alternatively, data sets may be analyzed by one or more data set analyzers 420 to identify one or more sparse indicators. Additionally or alternatively, data sets may be analyzed by one or more data set analyzers 420 to categorize each data set, alignment, or detected sparse indicator. Additionally or alternatively, data sets may be analyzed by one or more data set analyzers 420 to score each data set, alignment, or detected sparse indicator. Again, sparse indicators, categories, and scores may be transmitted to and/or stored in results data store 430, which may be included in data store 372.

Detecting sparse indicators may include aligning each data set with a reference data set. The reference data set may include part of a full reference data set and/or may include a data set identified based on identifying median or mode data elements across a plurality of data set derived from samples from a population. In some instances, an alignment is determined to be accurate throughout the data set, and differences between the data set and reference data set can be represented as sparse indicators, each corresponding to one or more positions (e.g., relative to an axis of the reference data set or to an axis of the data set). In some instances, a sparse indicator may further be defined using a value or identifier data of the data set (e.g., that differs from a corresponding value in the reference data set). In some instances, a sparse indicator may be defined based on identifying a type of structural difference detected in the data set relative to the reference data set (e.g., duplication, insertion, inversion or deletion). In some instances, an alignment is determined to be accurate throughout part of the data set but not for another part. It may then be determined that such partial alignment is attributable to the data set, for example, lacking representation of a part of the reference sequence or having an additional set of values. A sparse indicator may therefore identify information corresponding to multiple positions (e.g., reflecting a start and stop of a part of a reference data set not represented in a data set or the converse) and/or multiple values (e.g., reflecting which values were in one of either the reference data set or the data set but not in the other).

In some instances, a state transition likelihood associated with a particular deviation (e.g., sparse indicator) and/or with a combination of deviations is unknown or is associated with a below-threshold confidence. With reference again to FIG. 1 and FIG. 2, upon detecting such a deviation or combination (or a threshold quantity thereof), the particular deviation and/or combination may be identified in a review-request communication 265 and transmitted to an evaluation device 170. Evaluation device 170 may then present the identification to an evaluator 175 and detect input that is indicative of an estimated likelihood to associate with the deviation and/or combination, for example, as part of an optional review analysis process. A review-request response 285 may be transmitted from evaluation device 170 to assessment system 105, for example, to provide the results of any review or input generated by an evaluator 175. The data included in review-request response 285 may be used in report generation process of block 290 and may be included and/or otherwise influence the content of the final report transmitted in report transmission 295.

A result generated by assessment system 105 may include a quantitative or qualitative (e.g., categorical) likelihood variable, such as one corresponding to a transitioning to a particular state. For example, the likelihood variable may include a percentage probability or range of transitioning into a particular state. As another example, the likelihood variable may be partitioned into three categories.

Assessment system 105 may generate an electronic report, at block 290, that includes the result and/or that is selected based on the result. A report communication or transmission 295 may include the report and be transmitted to client 125 or facility 120, such as by way of client device 130 or requestor device 110a. As an example, a report may identify one or more sparse indicators detected in a client data set and/or a bucket of each of one or more sparse indicator. A report may identify a likelihood (e.g., numeric or categorical) of transitioning to a particular state and/or a technique for having generated such a result. A report may identify types of data (e.g., particular data-set units and/or other type of data) used in the analysis. A report may identify a confidence in a result (e.g., a likelihood variable). A report may identify a recommendation (e.g., to contact a requestor or to receive a particular test or evaluation).

In some instances, a report must be approved (e.g., by a requestor 115a or 115b) before it is transmitted to a client device 130. A report-reviewing interface may, but need not, include a configuration to allow a reviewing entity to change or add to the report. A report-reviewing interface may further allow or require a reviewing entity to identify a time at which to send the report to a client.

Assessment system 105 may update and may have access to a variety of data stores, part or all of which may be remote from, co-localized with assessment system 105, and/or included in assessment system 105. One or more of the data stores may include a relational data store, such that data from one data store or structure within a data store may be used to retrieve corresponding data from another data store or structure.

Each of one, more, or all of the data stores may be associated with one or more access constraints. Access constraints applicable to a given data store may be stored as part of the data store or separately (e.g., in an access control data store). Access constraints that apply to one type of data may differ from access constraints that apply to another type of data. For example, account and client data may be associated with stricter access constraints than results data, to make it more difficult for a user, developer, or hacker to be able to link data to a particular individual. An access constraint may identify one or more individuals, devices, systems, and/or occupations permitted to access some or all data in a data store. An access constraint may include a rule, such as one that indicates that a user is permitted to access data pertaining to any of a group of users that the entity was involved in with respect to a transfer of a kit, or that indicates that any low-level authorized user is permitted to access de-identified data but not identifiable data, or that indicates that a high-level authorized user is permitted to access all data. As another example, access constraints may indicate that process data is to be hidden from external developers and available to internal users; that data-set unit, sparse indicator, and data set availability data is to be made available to all authorized external developers and internal users; and that client data is to be availed to authorized internal users and only availed to external developers to the extent to which each corresponding users represented in the data is a user of the developer (e.g., and that the client authorized such data access).

When different access rights apply to different types of data, a query protocol may be established to address instances where a query relates to each type of data. For example, a query may request Variable X for each client corresponding to Data Y, and Variable X and Data Y may correspond to different access constraints. As another example, a query may request a count of clients for which both Data Y and Data Z were detected, and Data Y and Z may correspond to different access constraints. One example of a query protocol is to use a most restrictive overlap of data constraints applying to the query. Another example of a query protocol is to permit use of an at least partly more relaxed access constraint so long as it relates to defining a client set or state and not to results to be returned or processed.

In some instances, an access constraint is configured to inhibit an identification of particular data (e.g., client identity). Such a constraint may relate to a precision of requested data. To illustrate, a constraint may be configured to permit a user to request and receive data identifying client locations, so long as the request is configured to not request too specific of a location and/or so long as the request corresponds to a number of client data elements sufficiently large to obscure (e.g., in a statistical result) a precise location. Compound queries may be more sensitive to potential identification concerns, such that one or more access constraints are configured to permit access to less precise data when multiple data elements are being requested.

Various data stores may be included in assessment networks 100 and 300. The data stores may include, for example, an account data store 176, which may include login credentials for one or more users or clients and/or types of data access to be granted to each user or client; process data store 177, which may identify facility analysis characteristics pertaining to particular data elements (e.g., identifying a facility, piece of equipment, and/or processing time); data sets data store 178, which may identify one or more data sets associated with a given client or material, such as a sample; and one or more data-set expressions or signatures associated with a given client or material, such as a sample. The data stores may further or alternatively include a results data store 181, which may identify one or more sparse indicators identified by and/or one or more results generated by assessment system 105 that are associated with a given client or material, such as a sample.

The data stores may further or alternatively include a reports data store 182, which may include one or more report templates (e.g., each associated with one or more result types) and/or one or more reports to be transmitted or having been transmitted to a client device; and/or a relevance support data store 183, which may identify which types of data (e.g., data-set units, full or partial reference data sets, activity patterns, inputs, records, tests, etc.) are established to be, potentially, established not to be, or unknown whether to be relevant for evaluating a particular type of likelihood (e.g., a likelihood of transitioning into a particular state).

Relevance support data store 183 may include identifications of one or more content objects. The identifications may include, for example, web addresses, journal citations, or article identifiers. In some instances, an identification identifies one or more sources associated with the content object (e.g., scientist, author, journal, or data store). Content objects may be tagged with one or more tags, which may identify, for example, a sparse indicator, a data-set unit, a data set, and/or a type of assessment. In some instances, each of one or more content objects are associated with a score, which may reflect a credibility of the content object. The score may be based, for example, on a publication frequency of a source, an impact factor of a source, a date of publication of the content object, and/or a number of citations to the content object.

It will be appreciated that the illustrated data stores 155, 165, 176, 177, 178, 181, 182, and 183 may each, independently and optionally, be included as a portion of data store 372, which may include a relational database, for example.

Assessment network 100 may also include a user device 180 configured to detect input from a user 185. User 185 may be associated with an account or other authentication data indicating that access to some or all of the data is to be granted. Accordingly, user 185 may be able to interact with various interfaces (presented at user device 180) to view data pertaining to one or more particular clients (e.g., in an identified or de-identified manner), to view summary data that relates to data from multiple clients, to explore relationships between data types, and so on. In some instances, an interface may be configured to accept inputs from a user 185 so as to enable the user to request data pertaining to (for example) materials with sparse indicators in particular data-set units, particular sparse indicators and/or state likelihoods.

In some instances, data is transmitted by assessment system 105 and received at user device 180. The transmitted data may relate to durations of work flow processing time periods. Specifically, as may be appreciated by disclosures included herein, generating outputs for users and/or requestors may involve multiple steps, each of which may include a process, which may be referred to herein as a task, of an entity and/or device. Completion times of individual processes may then be monitored and assessed. A work flow may include a structure and definition for these processes. For example, various work flows may include some or all of the following tasks:

Inputs are collected at client device 130, transmitted by client device 130, and received by assessment system 105, where the inputs correspond to a preliminary request to conduct an assessment based on a material and ensure that all required inputs have been received;

A same or different client device 130 (e.g., a wearable device) collects and transmits other data indicative of the client's activity or status;

Inputs collected at requestor device 110*a*, 110*b* and transmitted to assessment system 105 that correspond to a request for assessment for the client;

Access control device 160*b* at facility 120 collects and transmits record data of the client;

Distribution device 135 receives alert corresponding to new request and address information and confirms shipping of kit for sample collection to the client;

Client 125 receives kit, collects material and sends to data generator 140;

Assessment device(s) 145 collects data-set data, and access control device 160*a* sends facility data to assessment system 105;

Assessment system 105 detects any sparse indicators in data set(s) and/or any modifications in data set expression;

Assessment system 105 assigns any sparse indicators and/or data set availability modifications;

Evaluation device 170 collects inputs identifying an assignment of any sparse indicators and/or data set availability modifications as of an unknown likelihood;

Confirmatory facility testing of any sample associated with a sparse indicator and/or data set availability modification having a particular assignment at same or different facilities;

Assessment system 105 aggregates sparse indicator data, assignment data, record data, user or client inputs, other data, and/or activity or status data and generates one or more likelihood variables;

Assessment system 105 generates electronic report with the one or more likelihood variables;

Evaluation device 170 and/or requestor device 110*a* collect inputs indicating that the electronic report is approved for transmission to client device 130; and Assessment system 105 transmits the electronic report to client device 130.

A work flow may include a task order that indicates that, for example, a first task is to be completed prior to performance of a second task, though a work flow may alternatively be configured such that at least some tasks may be performed in parallel. In some instances, one or more tasks in a work flow are conditional tasks that need not be performed during each iteration of the work flow. Rather, whether a conditional task is to be performed may depend on a circumstance, such as whether a result from a prior task is of a particular type or exceeds a threshold.

Using a work flow, assessment system 105 may track timing of individual tasks during individual iterations of a work flow. Each iteration may correspond to generating a likelihood variable for a given client and may involve various other entities (e.g., reviewers, facilities, etc.), which may be selected based on, for example, user preference, a physical location of a client device, and/or availability. For tasks performed at assessment system 105, timing may be directly determined. For tasks performed by, at, and/or via another device, assessment system 105 may track timing via electronic transmissions between systems. For example, a start may be identified by an instruction communication sent from assessment system 105 and/or a when a communication was received indicating that the corresponding task was beginning. As another example, an end time may be identified by transmission of a communication including a result of the corresponding task sent from assessment system 105 and/or when a communication was received indicating that the corresponding task was complete.

Figure 5:
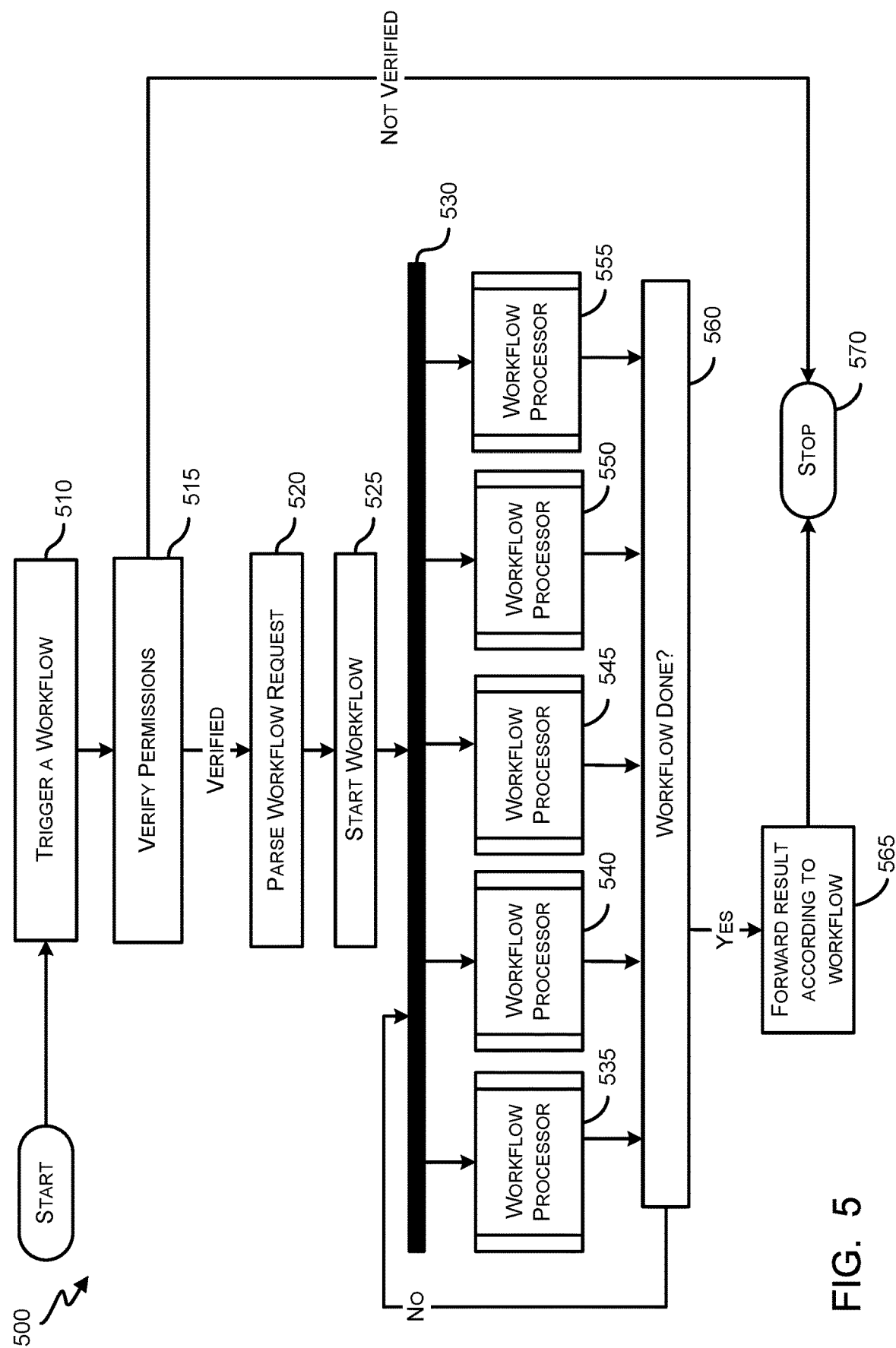
FIG. 5 shows an illustration of a work flow iteration, in accordance with some embodiments.

FIG. 5 shows a representation of an embodiment of a process 500 for processing tasks in the assessment network 100. The process starts when an event triggers a first work flow as shown at block 510. Any number of events occurring internal to the assessment network 100 and external to the assessment network 100 may trigger a first work flow in any number of ways. Each of the assessment system 105, a requestor device 110, a client device 130, a distribution device 135, a facility data generator, an evaluation device 170, a user device 180, and an external assessment device 190 may trigger a work flow, for example. For instance, the assessment system 105 may trigger a work flow when it receives an electronic request 205. A requestor device 110 may trigger a work flow by transmitting electronic request 205. A user device may trigger a work flow based on inputs collected. A data generator 140 may trigger a work flow upon receipt of a sample. Other examples are possible and it will be appreciated from the present description that any one or more data transmissions between various devices and systems of assessment network 100 may trigger a work flow. It will also be appreciated that various work flows may initiated sequentially or simultaneously, depending on the particular need for completion of one work flow to complete before another work flow may begin. In addition, additional work flows may be triggered while in the midst of processing one work flow. In some embodiments, an assessment system or assessment device manages and/or coordinates triggered work flows. Optionally, task start times may be tracked, as described above, and triggering a work flow may include tracking the start time of tasks associated with the work flow.

Some task work flows may require verification of permissions and/or authorizations, such as depicted at block 515, before the work flow is permitted to begin. For example, a transmission of record data of a client may require explicit authorization from a client or a requestor before the transmission may begin, for example, due to the sensitivity of information that may be included in the record data. As another example, transmission of information of a client to an external assessment device may also require client permission. In this way, permission verification may prevent unanticipated or unauthorized transmission of information to a particular work flow processor for which such transmission may be undesirable. Timing of permission request and verification may further be tracked, such as to allow identification of bottlenecks in work flow and/or task processing associated with permission verification. U.S. patent application Ser. No. 15/133,089, filed on Apr. 19, 2016 and U.S. Provisional Applications 62/150,218, filed on Apr. 20, 2016, and 62/274,660, filed on Jan. 4, 2016, disclose details regarding various work flow processes, and are each hereby incorporated by reference in its entirety for all purposes.

As illustrated in FIG. 5, if permissions are not verified, the work flow may be stopped, at block 570. If permissions are verified, the work flow may proceed to block 520. It will be appreciated that not all work flows require permission verification, and so block 515 may be considered to be optional.

Depending on the particular work flow initiated, the work flow request may require parsing, at block 520, to ensure that various portions of the work flow may be handled appropriately. Parsing may include determining that all required inputs, data, and/or materials needed for completing the work flow are available. In the event that additional inputs, data, and/or materials are needed, the work flow may be returned to the triggering device to request the additional inputs, data, and/or materials, for example. Parsing may also include aspects of load-balancing. Parsing may also include, for example, analyzing the work flow request and associated data and/or materials to ensure the data, materials and/or multiple individual sub-work flow processes are directed to an appropriate work flow processor 535, 540, 545, 550, 555, etc. Task start times may optionally be tracked based on completion of parsing a work flow request, for example.

In one embodiment, a work flow may correspond to performing a data set analysis on a sample, which may include dividing the sample into sub-samples. The sub-samples may, for example, be redundantly analyzed to ensure accuracy. Parsing 520 may include identifying necessary resources for completing a particular work flow.

After parsing the work flow request, the triggered work flow is started, at block 525. Optionally, synchronizer 530 oversees the processing of individual work flow processes by work flow processors. Optionally, tracked task start times may correspond to times at which the triggered work flow is actually passed to a work flow processor.

Some task work flows may include multiple individual work flow processes, such as a sequencing work flow for sequencing data-set unit data or sparse indicator data from a sample, where each individual work flow process may correspond to, for example, one or more data sets. These individual work flow processes may be performed in series, for example, such as if a particular work flow process requires input from a previous work flow process. The individual work flow processes may alternatively be performed in parallel, for example, if the separate work flow processes do not rely on an a result from another work flow process that may be performed simultaneously. Additionally, individual work flow processes may be started and completed without regard to other work flow processes that may be operating. Upon a work flow processor 535, 540, 545, 550, 555 completing the designated tasks, at 560, the work flow may be evaluated to determine whether the work flow is completed. If additional processing is required, the work flow may return to synchronizer 530 for appropriate queuing. If no additional processing is required, the work flow result may be forwarded as appropriate, at 565. Once a particular work flow is forwarded, the task associated with the work flow may stop, at block 570. Optionally, task stop or end times may be tracked based on the time at which a work flow proceeds to stop at block 570.

Assessment system 105 may store task start and completion times, and/or task completion time periods (i.e., a difference between corresponding task completion and task start times) in process data store 177 in association with an identifier of the corresponding task and an identifier of a corresponding work flow iteration (e.g., an identifier of a client or sample). Assessment system 105 may collect task start and completion times that correspond, for example, to a given time period, facility, user or client group, analysis type, etc. and analyze the data at a population level. Through such analysis, assessment system 105 may identify average, median, or mode completion time periods for individual tasks so as to identify tasks, facilities, or entities associated with work flow processing delay. Further or alternatively, assessment system 105 may identify a backlog for individual tasks by identifying a number of "open" tasks for which a start time has been identified but for which no completion time is identified. Tasks, facilities, and/or entities associated with high backlog may then be identified.

Such task completion time monitoring may be performed automatically and/or in response to a query communication from user device 180. For example, assessment system 105 may determine, for each handling entity (e.g., facility, distribution device, reviewer, or facility) a portion of tasks completed by a first threshold time identified for a given task. Upon detecting that the portion exceeds a second threshold, an alert communication may be transmitted to user device 180 and/or a device of an associated entity. As another example, assessment system 105 may present a statistic (e.g., mean) corresponding to a processing time of each task in a work flow. The presentation may be interactive, such that more details about a statistic may be presented in response to a user selection of the statistic. For example, the statistic may be broken down by entity and/or task start time period, or more detailed information (e.g., a distribution or list of start and completion times) may be presented.

In some instances, data transmitted from assessment system 105 to user device 180 may relate to data queries received from user device 180. The query may, in some instances, include one that specifically or implicitly identifies one or more data-set units. For example, identification of a given kit or assessment may be associated with one or more data-set units. Assessment system 105 may identify data that any access constraints indicate are accessible to the user, and present high-level population data. For example, assessment system 105 may identify a portion of clients for which any sparse indicator or a particular sparse indicator was detected at each of the one or more data-set units. Such data may be presented in an interactive manner, such that a user may select a represented portion of the data to drill down into that data. For example, the interface may accept a selection of a representation of each data-set unit, and the interface may be updated to identify a distribution of particular sparse indicators detected at the data-set unit.

A drill-down may be configured to, at some level, begin representing non-data set data. For example, a selection of a particular sparse indicator or data-set unit may result in a display identifying a distribution of history data or demographic data from amongst clients associated with the particular sparse indicator or a sparse indicator at the data-set unit. Thus, the drill-down may include retrieving data from different data stores depending on a level of precision. Further, each step in the drill-down may involve evaluating one or more applicable access constraints.

In some instances, a query may pertain to one or more data-set units, and query processing may include retrieving data (or results derived therefrom) and retrieving data set availability data (or results derived therefrom). For example, query processing may include identifying, for each subject and for each of the one or more data-set units, whether a sparse indicator or an data set availability modification was detected. A query result presentation may identify, for example, a portion of subjects for which a sparse indicator or modification was detected for each of the data-set units and/or a query result presentation may identify, for each of the one or more data-set units, a portion of subjects or clients for which a particular type of sparse indicator or modification was detected. The presentation may again be configured to accept drill-down inputs so as to enable a user to further explore the pertinent data.

As another example, query processing may include identifying instances in which, for a given client, both a sparse indicator (e.g., generally or of a particular type) and an data set availability modification (e.g., generally or of a particular type) was detected (e.g., generally, at a particular data-set unit and/or at a particular position at a data-set unit).

Again with reference to FIG. 1, assessment network 100 may also include an external assessment device 190 configured to detect input from a developer 195. Via such inputs, external assessment device 190 may send electronic requests for data (e.g., relating to particular data-set units, a particular user or client and/or particular user or client inputs) to assessment system 105. The inputs may be received, for example, via a webpage, application, or app page, which may identify general types of data that is available for restricted access. Assessment system 105 may evaluate the request to determine, for example, whether a corresponding client 125 authorized such access (which may be verified via a communication exchange between assessment system 105 and client device 130) and/or whether such access is relevant to a purported type of analysis.

The evaluation may include assessing one or more permissions associated with a given user or client. In various instances, a permission may be set to be conditioned upon an entity or system transmitting a request, a type of data being requested, a size of data being requested, or a potential type of processing identified as being a use for the data. For example, a client may specify that an external assessment device may be granted access to data, such as data that includes data sets or sparse indicator detections, if the requested data pertains to fewer than a first threshold number of data-set units, that access to data that includes sparse indicator detection may be granted if the requested data pertains to fewer than a second threshold number of data-set units, and that access to the data is to be otherwise restricted.

Evaluation processing may depend, in part, on whether a system or entity associated with a request has provided any data previously or presently and/or what type of data is being provided. For example, external assessment devices and/or associated systems may provide data (e.g., generated from an external facility and/or client sample), results data, input data, data set availability data, test data, and/or history data.

Evaluation processing may depend on one or more permissions or restrictions associated with a request. The permissions or restrictions may be set, for example, based on client input, or lack thereof, and/or based on which type of analysis and/or data storage was initially agreed to by a client. For example, an interface may be configured so as to enable a user or client to permit or restrict storage of particular types of data (e.g., data sets and/or sparse indicator detection beyond what is needed to perform a requested analysis), to permit or restrict sharing data to one or more other entities (e.g., generally, of a given type or specific entities), and/or to permit or restrict using data to perform one or more other types of analyses. Permissions or restrictions pertaining to whether various analyses may be particularly important given that rules or regulations may require particular results of analyses to be transmitted to a client. Thus, if such information is not desired, analyses must be restricted.

In some instances, an interface may be configured to enable a user or client to specify a degree of identification to be associated with data of the client with regard to storage and/or distribution. For example, a user or client may be able to indicate that data and/or results are to be associated with a pseudo-randomly generated unique identifier of the client rather than client identifying information. As another example, a client may be able to indicate that data is to be stored so as to require a key for access, which may be held by the client. As another example, a client may authorize transmission of the client's data to external assessment devices so long as identifying information of the client (e.g., name, email, address, social security number, phone number, and so on) is not provided without subsequent explicit permission.

In some instances, a same or different permission may be established to apply to other type of data (e.g., with regard to storage and/or distribution), such as personal data, inputs and/or sensor data. In some instances, a same or different permission may be established so as to relate to data collected from external systems. For example, a permission may indicate whether an assessment system is authorized to request physician-system data (and/or what type of data), an external assessment device-data, etc., and/or how an assessment is to handle results provided by an external system.

If the evaluation indicates that access is to be granted, assessment system 105 may, for example, send an instruction communication to data generator 140 to conduct a new analysis of an existing sample, send a data request to a device (e.g., access control device 160b, client device 130), and/or retrieve data from a data store (e.g., and extract pertinent information from any larger data structure, such as extracting data-set unit-specific data from a reference dataset). When part or all of the data is accessible, one or more communications may be transmitted to the developer. The one or more meetings may include the data and/or may include information (e.g., access credentials, login information, or ftp IP address and credential information) to enable the developer to access the data. In some instances, other data different from that which was requested may be provided. The other data may include, for example, quality control metrics of the provided data, other data determined to be relevant to an analysis, and/or other data that is being provided in lieu part or all of data that had been requested.

Various devices in assessment network 100 may communicate with one or more other devices in assessment network 100 via a network, such as a communication system, the Internet, a local-area network, or a short-range network. Communications may be sent in a secure manner to, e.g., inhibit unauthorized access to health-record data. Techniques such as token authentication and/or encryption may be used.

It will be appreciated that the representations of devices and configurations depicted in FIGS. 1, 2, and 3 are illustrative. For example, while a single data generator 140, client device 130, and data stores 178, etc., are shown, a system may include multiple data generators 140, client devices 130, data store 178, etc. As another example, while access control devices 160a, 160b are shown as being connected to data store 155 and record data store 165, additional access control devices may be present in assessment network 100. For example, an access control device may be included within or connected to assessment system 105 so as to control access that requestor device 110b, client device 130, distribution device 135, evaluation device 170, user device 180 and/or external assessment device 190 may achieve.

Figure 6:
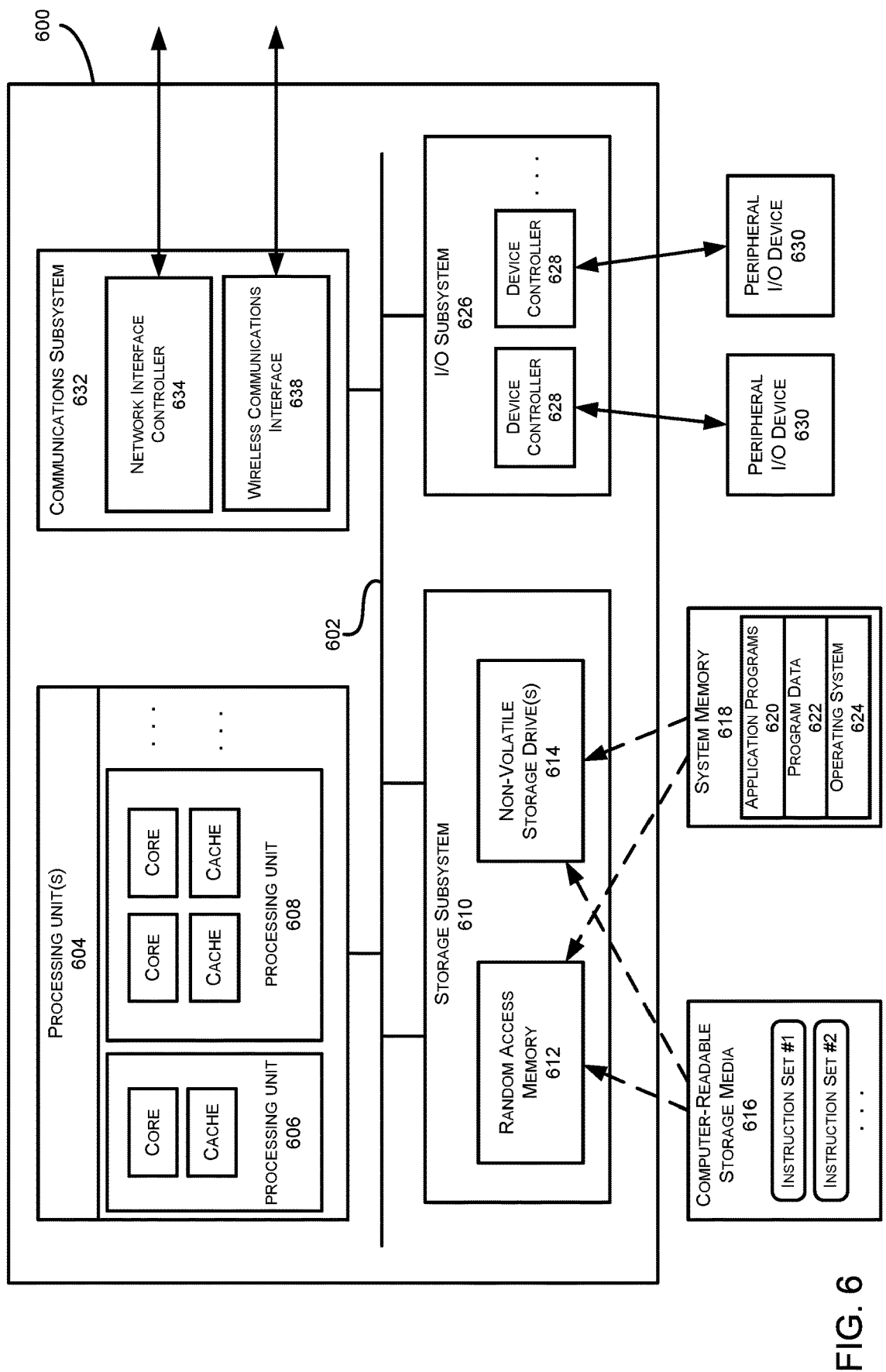
FIG. 6 shows a block diagram of an example data processing network device or system, in accordance with some embodiments.

With reference now to FIG. 6, a block diagram of an illustrative assessment network device 600 is shown. The device 600 may correspond to any of the devices or systems of the assessment network 100 described above, or any other computing devices described herein, and specifically may include, for example, one or several of an assessment system 105, a requestor device 110, a client device 130, a distribution device 135, an assessment device 145, a technician device 150, an access control device 160a, a reviewer or user device 180, an external assessment device 190, external system 249, data-characterizer device 410, data set analyzer 420, and/or any of the work flow processors 535, 540, 545, 550, and 555. Aspects of device 600 may further be incorporated in one or more of data stores 155, 165, 176, 177, 178, 181, 182, 183, 415, 425, and 430 and data store 372. It will be appreciated that each of the devices referred to that may correspond to an instance of device 600 may be independent and unique from all other instances of device 600 and may include fewer or additional components as those illustrated in FIG. 6.

In the example illustrated in FIG. 6, device 600 includes processing units 604 that communicate with a number of peripheral subsystems via a bus subsystem 602. These peripheral subsystems include, for example, a storage subsystem 610, an I/O subsystem 626, and a communications subsystem 632.

Bus subsystem 602 provides a mechanism for letting the various components and subsystems of device 600 communicate with each other. Although bus subsystem 602 is shown schematically as a single bus, alternative embodiments of the bus subsystem may utilize multiple buses. Bus subsystem 602 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which may be implemented as a Mezzanine bus manufactured to the IEEE P1386.1 standard.

Processing unit 604, which may be implemented as one or more integrated circuits (e.g., a conventional microprocessor or microcontroller), controls the operation of device 600. Processing unit 604 may be implemented as a special purpose processor, such an application-specific integrated circuit, which may be customized for a particular use and not usable for general-purpose use. One or more processors, including single core and/or multicore processors, may be included in processing unit 604. As shown in FIG. 6, processing unit 604 may be implemented as one or more independent processing units 606 and/or 608 with single or multicore processors and processor caches included in each processing unit. In other embodiments, processing unit 604 may also be implemented as a quad-core processing unit or larger multicore designs (e.g., hexa-core processors, octo-core processors, ten-core processors, or greater).

Processing unit 604 may execute a variety of software processes embodied in program code, and may maintain multiple concurrently executing programs or processes. At any given time, some or all of the program code to be executed may be resident in processor(s) 604 and/or in storage subsystem 610. In some embodiments, device 600 may include one or more specialized processors, such as digital signal processors (DSPs), outboard processors, graphics processors, application-specific processors, and/or the like.

I/O subsystem 626 may include device controllers 628 for one or more user interface input devices and/or user interface output devices 630. User interface input and output devices 630 may be integral with device 600 (e.g., integrated audio/video systems, and/or touchscreen displays), or may be separate peripheral devices which are attachable/detachable from device 600. The I/O subsystem 626 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 630 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 630 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, haptic devices, and eye gaze tracking devices. Additional input devices 630 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 630 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, haptic devices, and the like. In general, use of the term "output device" is intended to include all possible types of devices and mechanisms for outputting information from device 600 to a user or other computer. For example, output devices 630 may include, without limitation, a variety of display devices that visually convey text, graphics and audio/video information such as monitors, printers, speakers, headphones, automotive navigation systems, plotters, voice output devices, and modems.

Device 600 may comprise one or more storage subsystems 610, comprising hardware and software components used for storing data and program instructions, such as system memory 618 and computer-readable storage media 616. The system memory 618 and/or computer-readable storage media 616 may store program instructions that are loadable and executable on processing units 604, as well as data generated during the execution of these programs. Program instructions may include instructions to perform one or more actions or part(s) or all of one or more methods or processes described herein. For example, program instructions may include instructions for identifying and/or aligning sparse indicators. Program instructions may include instructions for generating, transmitting, and/or receiving communications. Program instructions may include instructions for automated processing. Program instructions may include instructions for generating automated processing and/or stage results. Program instructions may include instructions for performing a work flow iteration.

Depending on the configuration and type of device 600, system memory 618 may be stored in volatile memory (such as random access memory (RAM) 512) and/or in non-volatile storage drives 614 (such as read-only memory (ROM), flash memory, etc.) The RAM 612 may contain data and/or program modules that are immediately accessible to and/or presently being operated and executed by processing units 604. In some implementations, system memory 618 may include multiple different types of memory, such as static random access memory (SRAM) or dynamic random access memory (DRAM). In some implementations, a basic input/output system (BIOS), containing the basic routines that help to transfer information between elements within device 600, such as during start-up, may typically be stored in the non-volatile storage drives 614. By way of example, and not limitation, system memory 618 may include application programs 620, such as user applications, Web browsers, mid-tier applications, server applications, etc., program data 622, and an operating system 624.

Storage subsystem 610 also may provide one or more tangible computer-readable storage media 616 for storing the basic programming and data constructs that provide the functionality of some embodiments. Software (programs, code modules, instructions) that when executed by a processor provide the functionality described herein may be stored in storage subsystem 610. These software modules or instructions may be executed by processing units 604. Storage subsystem 610 may also provide a repository for storing data used in accordance with the present invention.

Storage subsystem 610 may also include a computer-readable storage media reader that may further be connected to computer-readable storage media 616. Together and, optionally, in combination with system memory 618, computer-readable storage media 616 may comprehensively represent remote, local, fixed, and/or removable storage devices plus storage media for temporarily and/or more permanently containing, storing, transmitting, and retrieving computer-readable information.

Computer-readable storage media 616 containing program code, or portions of program code, may include any appropriate media known or used in the art, including storage media and communication media, such as but not limited to, volatile and non-volatile, removable and non-removable media implemented in any method or technology for storage and/or transmission of information. This may include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This may also include nontangible computer-readable media, such as data signals, data transmissions, or any other medium that may be used to transmit the desired information and that may be accessed by device 600.

By way of example, computer-readable storage media 616 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray disk, or other optical media. Computer-readable storage media 616 may include, but is not limited to, Zip drives, flash memory cards, universal serial bus (USB) flash drives, secure digital (SD) cards, DVD disks, digital video tape, and the like. Computer-readable storage media 616 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for device 600.

Communications subsystem 632 may provide a communication interface from device 600 and remote computing devices via one or more communication networks, including local area networks (LANs), wide area networks (WANs) (e.g., the Internet), and various wireless telecommunications networks. As illustrated in FIG. 6, the communications subsystem 632 may include, for example, one or more network interface controllers (NICs) 634, such as Ethernet cards, Asynchronous Transfer Mode NICs, Token Ring NICs, and the like, as well as one or more wireless communications interfaces 638, such as wireless network interface controllers (WNICs), wireless network adapters, and the like. Additionally and/or alternatively, the communications subsystem 632 may include one or more modems (telephone, satellite, cable, ISDN), synchronous or asynchronous digital subscriber line (DSL) units, FireWire interfaces, USB interfaces, and the like. Communications subsystem 632 also may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.11 family standards, or other mobile communication technologies, or any combination thereof), global positioning system (GPS) receiver components, and/or other components.

The various physical components of the communications subsystem 632 may be detachable components coupled to the device 600 via a computer network, a FireWire bus, a serial bus, or the like, and/or may be physically integrated onto a motherboard or circuit board of device 600. Communications subsystem 632 also may be implemented in whole or in part by software.

In some embodiments, communications subsystem 632 may also receive input communication in the form of structured and/or unstructured data feeds, event streams, event updates, and the like, on behalf of one or more users who may use or access device 600. For example, communications subsystem 632 may be configured to receive data feeds in real-time from other communication services, web feeds such as Rich Site Summary (RSS) feeds, and/or real-time updates from one or more third party information sources. Additionally, communications subsystem 632 may be configured to receive data in the form of continuous data streams, which may include event streams of real-time events and/or event updates (e.g., data set completion, results transmission, other data transmission, report transmission, etc.). Communications subsystem 632 may output such structured and/or unstructured data feeds, event streams, event updates, and the like to one or more data stores that may be in communication with device 600.

Due to the ever-changing nature of computers and networks, the description of device 600 depicted in FIG. 6 is intended only as a specific example. Many other configurations having more or fewer components than the device depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, it will be appreciated that there are other ways and/or methods to implement the various embodiments.

Figure 7:
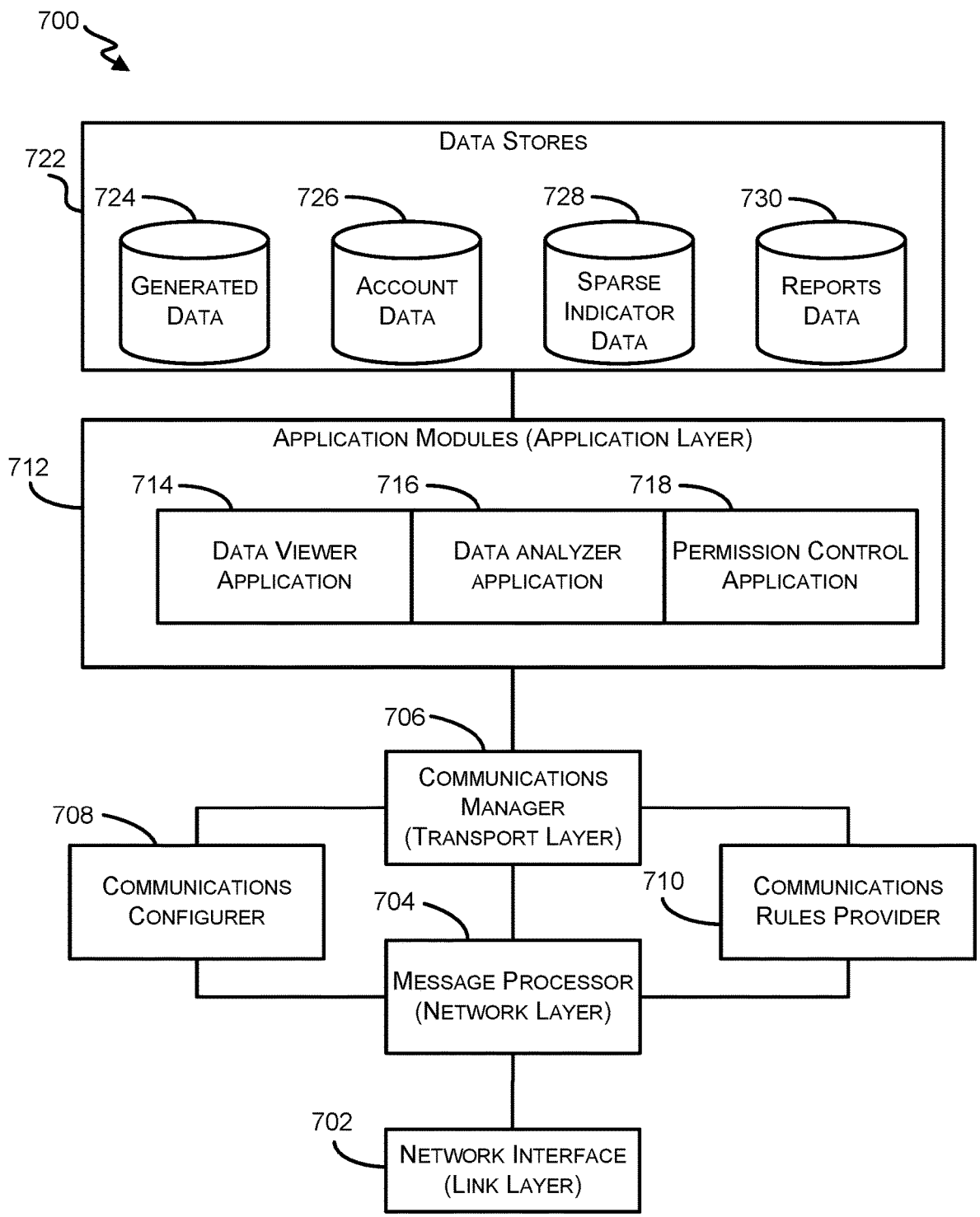
FIG. 7 illustrates components of a data processing network device or system, in accordance with some embodiments.

With reference now to FIG. 7, a diagram of components of an illustrative assessment network device 700 is shown. The device 700 may correspond to any of the devices or systems of the assessment network 100 described above, or any other computing devices described herein, and specifically may include, for example, one or several of an assessment system 105, a requestor device 110, a client device 130, a distribution device 135, an assessment device 145, a technician device 150, an access control device 160a, a reviewer or user device 180, an external assessment device 190, external system 249, data-characterizer device 410, data set analyzer 420, any of the work flow processors 535, 540, 545, 550, and 555, and/or device 600. Aspects of device 700 may further be incorporated in one or more of data stores 155, 165, 176, 177, 178, 181, 182, 183, 415, 425, and 430, and data store 372. It will be appreciated that each of the devices referred to that may correspond to an instance of device 700 may be independent and unique from all other instances of device 700 and may include fewer or additional components as those illustrated in FIG. 7.

Various components may be included in device 700. Components may include some or all of the following: a network interface 702 (which may operate in or function as a link layer of a protocol stack), a message processor 704 (which may operate in or function as a network layer of a protocol stack), a communications manager 706 (which may operate in or function as a transport layer of a protocol stack), a communications configurer 708 (which may operate in or function as a portion of transport and/or network layer in a protocol stack), a communications rules provider 710 (which may operate in or function as part of a transport and/or network layer in a protocol stack), and applications 712 (which may operate in or function as an application layer of a protocol stack).

Network interface 702 receives and transmits messages via one or more hardware components that provide a link-layer interconnect. The hardware components associated with network interface 702 may include, for example, a radio frequency (RF) antenna or a port (e.g., Ethernet port) and supporting circuitry. In some embodiments, network interface 702 may be configured to support wireless communication, e.g., using Wi-Fi (IEEE 802.11 family standards), Bluetooth, or other wireless communications standards.

The RF antenna, if present, may be configured to convert electric signals into radio and/or magnetic signals (e.g., to radio waves) to transmit to another device and/or to receive radio and/or magnetic signals and convert them to electric signals. RF antenna may be tuned to operate within a particular frequency band. In some instances, device 700 includes multiple antennas, and the antennas may be, for example, physically separated. In some instances, antennas differ with respect to radiation patterns, polarizations, take-off angle gain and/or tuning bands. Network interface 702 may include one or more phase shifters, filters, attenuators, amplifiers, switches and/or other components to demodulate received signals, coordinate signal transmission, and/or facilitate high-quality signal transmission and receipt using the RF antenna.

In some instances, network interface 702 includes a virtual network interface, so as to enable the device to utilize an intermediate device for signal transmission or reception. For example, network interface 702 may include or utilize virtual private networking (VPN) software.

Network interface 702 may be configured to transmit and receive signals over one or more connection types. For example, network interface may be configured to transmit and receive Wi-Fi signals, Ethernet signals, cellular signals, Bluetooth signals, etc.

Message processor 704 may coordinate communication with other electronic devices or systems, such as one or more user devices, requestor devices, assessment systems, data stores, assessment devices, distribution device, reviewer device, etc. In one instance, message processor 704 is able to communicate using a plurality of protocols (e.g., any known, future and/or convenient protocol such as, but not limited to, internet protocol (IP), short message service, (SMS), multimedia message service (MMS), etc.). Message processor 704 may further optionally serialize incoming and/or outgoing messages and facilitate queuing of incoming and outgoing message traffic.

Message processor 704 may perform functions of an Internet or network layer in a network protocol stack. For example, in some instances, message processor 704 may format data packets or segments, combine data packet fragments, fragment data packets and/or identify destination applications and/or device addresses. For example, message processor 704 may defragment and analyze an incoming message to determine whether it is to be forwarded to another device and, if so, may address and fragment the message before sending it to the network interface 702 to be transmitted. As another example, message processor 704 may defragment and analyze an incoming message to identify a destination application that is to receive the message and may then direct the message (e.g., via a transport layer) to the application.

Communications manager 706 may implement transport-layer functions. For example, communications manager 706 may identify a transport protocol for an outgoing message (e.g., transmission control protocol (TCP) or user diagram protocol (UDP)) and appropriately encapsulate the message into transport protocol data units. Message processor 704 may initiate establishment of connections between devices, monitor transmissions failures, control data transmission rates, and monitor transmission quality. As another example, communications manager 706 may read a header of an incoming message to identify an application layer protocol used to receive the message's data. The data may be separated from the header and sent to the appropriate application. Message processor 704 may also monitor the quality of incoming messages, detect out of order incoming packets, detect missing packets, reorder out of order packets, request retransmission of missing packets, request retransmission of out of order packets, etc.

In some instances, characteristics of message-receipt or message-transmission quality may be used to identify a quality status of an established communications link. In some instances, communications manager 706 may be configured to detect signals indicating the stability of an established communications link (e.g., a periodic signal from the other device system, which if received without dropouts, indicates a stable link).

In some instances, a communication configurer 708 is provided to track attributes of another system so as to facilitate establishment of a communication session. In one embodiment, communication configurer 708 further ensures that inter-device communications are conducted in accordance with the identified communication attributes and/or rules. Communication configurer 708 may maintain an updated record of the communication attributes of one or more devices or systems. In one embodiment, communications configurer 708 ensures that communications manager 706 may deliver the payload provided by message processor 704 to the destination (e.g., by ensuring that the correct protocol corresponding to the receiving system is used). Optionally, communications configurer 708 may reformat, encapsulate, or otherwise modify the messages directed to the message processor 704 to ensure that the message processor 704 is able to adequately facilitate transmission of the messages to their ultimate destination.

A communications rules provider 710 may implement one or more communication rules that relate to details of signal transmissions or receipt. For example, a rule may specify or constrain a protocol to be used, a transmission time, a type of link or connection to be used, a destination device, and/or a number of destination devices. A rule may be generally applicable or conditionally applicable (e.g., only applying for messages corresponding to a particular app, during a particular time of day, while a device is in a particular geographical region, when a usage of a local device resource exceeds a threshold, etc.). For example, a rule may identify a technique for selecting between a set of potential destination devices based on attributes of the set of potential destination devices as tracked by communication configure 708. To illustrate, a device having a short response latency may be selected as a destination device. As another example, communications rules provider 710 may maintain associations between various devices or systems and resources. Thus, messages corresponding to particular resources may be selectively transmitted to destinations having access to such resources.

A variety of applications 712 may be configured to initiate message transmission, process incoming transmissions, facilitate permissions requests for access to protected data, facilitate automatic access to protected data, facilitate task work flow permission verification, and/or performing other functions. In the instance depicted in FIG. 7, application modules 712 include a data viewer application 714, a data analyzer application 716, and/or a permission control application 718. It will be appreciated that the application modules depicted in FIG. 7 are merely examples and other example application modules are include, but are not limited to, one that is associated with aspects of part or all of each of one or more actions, methods, and/or processes disclosed herein.

Data stores 722 may store data for use by application modules 712, as necessary, and may include, for example, generated data store 724, account data store 726, sparse indicator data store 728, and reports data store 730. Optionally, data store 372 may be included in data stores 722. It will be appreciated that fewer or more or different data stores than those illustrated in FIG. 7 may be included in data stores 722, such as any one or more of data stores 155, 165, 176, 177, 178, 181, 182, and 183 depicted in FIG. 1.

One or more of data stores 724, 726, 728, and 730 may be a relational data store, such that elements in one data store may be referenced within another data store. For example, account data store 726 may associate an identifier of a particular account with an identifier of a particular user or client. Additional information about the user may then be retrieved by looking up the account identifier in sparse indicator data store 728, for example.

The components illustrated in FIG. 7 may be useful for establishing data communications and exchanging data between various other systems. For example, independent instances of device 700 may represent the requestor device 110 and the assessment system 105 illustrated in FIGS. 1 and 2. Other examples are possible.

As an example, data analyzer application 716 may perform alignment of data sets, request reference data, determine sparse indicators, determine scores, determine buckets, etc. Such actions may be performed in response to messages received by device 700 from another instance of device 700. If data that is unavailable locally in device 700 is needed by an application module 712, a request may be transmitted by device 700, first by generating the request, forwarding the request to communications manager 706, which then may process and modify the request as necessary for subsequent handling by message processor 704. In turn, message processor 704 may process and modify the request as necessary, such as by adding header and/or footer information, for subsequent handling by network interface 702. Network interface 702 may then perform further processing and modification of the request, such as by adding additional header and/or footer information, and then facilitate transmission of the request to a remote system, such as an external system that may possess the needed data.

Figure 8:
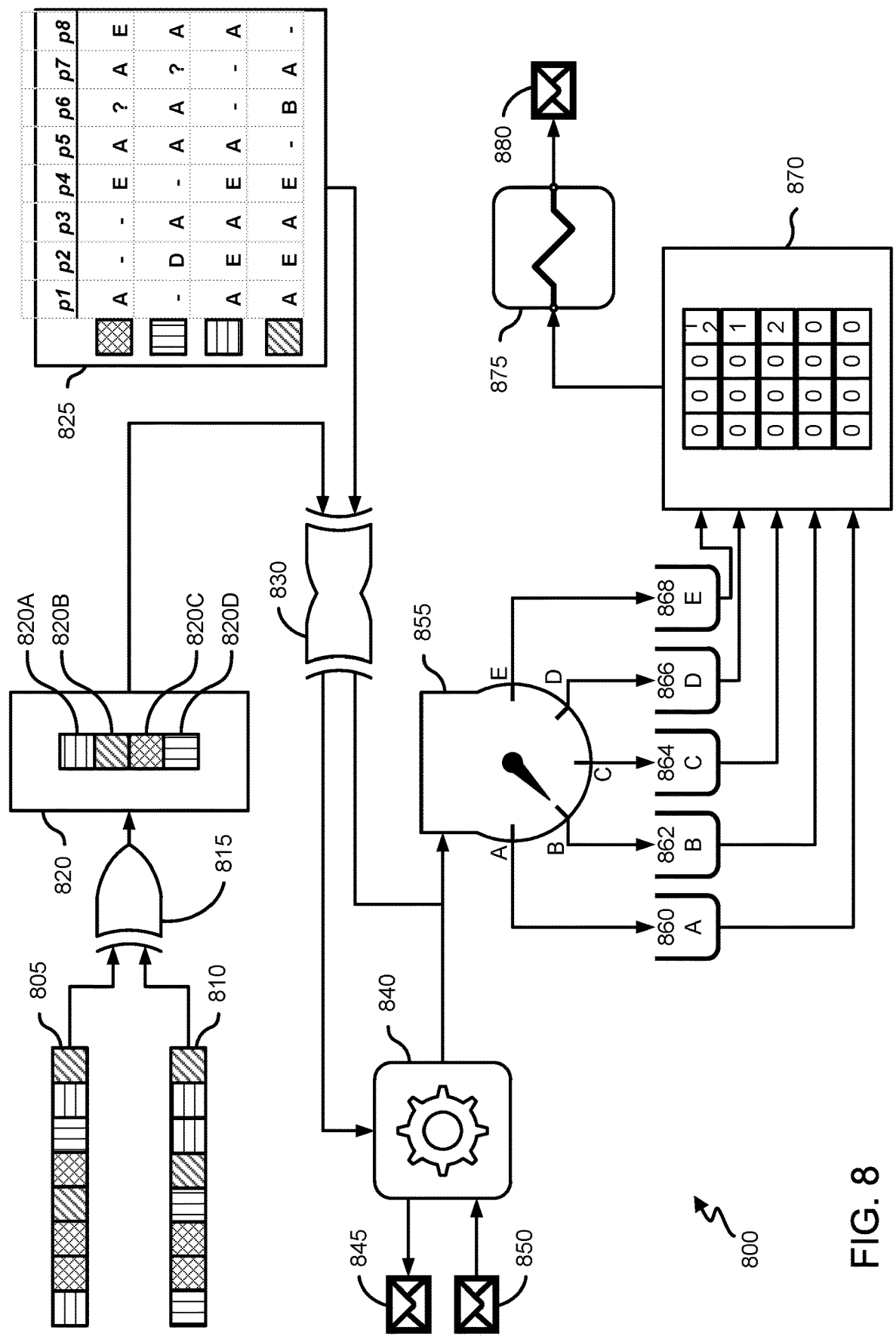
FIG. 8 shows a representation of a system for generating communications, in accordance with some embodiments.

Referring next to FIG. 8, a representation of a system 800 for assigning sparse indicators to data buckets is shown, such as by performing a work flow iteration(s), performing automated processing for stage(s), generating stage result(s) from one or more stages of a work flow, and analyzing data buckets. System 800 may represent portions of assessment system 105 and may, for example, include portions of data generator 140. System 800 may be in data communication with one or more other components of assessment network 100 or 300, such as client device 130 and data store 372, for example.

System 800 includes an assessment device 815, which may be used to analyze and/or compare generated data 805 with reference data 810 to generate a data stream 820, which may include one or more sparse indicators 820A, 820B, 820C, 820D, etc. Thus, it will be appreciated that data 805 may include data aligned with a portion of a reference set, such that individual values of data 805 may be compared to corresponding values in reference data 810. In some embodiments, multiple individual data sets are obtained for a particular client and a compiled data set may be assembled from alignments of a plurality of the individual data sets. The compiled data set may then be compared with one or more reference data sets or a compiled reference data set to identify sparse indicators associated with the compiled data set for the particular client. It will also be appreciated that generated data 805 may include identifier data and coverage data that may be used by assessment device 815 in generating data stream 820, such as by comparing identifier data with reference data 810 and using coverage data in tandem to determine a type, identity, value, and/or confidence metric associated with a sparse indicator in data stream 820.

Different types of sparse indicators may be identified, such as a one-element sparse indicator representing a single data element different from a reference data set, or a clustered sparse indicator representing a set of consecutive data elements different from a reference data set. A clustered sparse indicator may be detected upon determining (for example) that a series of elements in a data set generally differ from those in a reference data set or that values in a coverage set change across the set so as to indicate that a portion of the reference data set is over- or underrepresented in the data set. Thus, in some instances, a reference set may include a reference coverage set. Although only four sparse indicators 820A-820D are depicted as part of data stream 820, it will be appreciated that more or fewer sparse indicators may be identified for a particular set of generated data and that the four sparse indicators 820A-820D are merely examples.

System 800 further includes a look-up engine 830, which may determine whether each individual sparse indicator corresponds to bucket-assignment data in stored data 825 (e.g., a look-up table). For example, a look-up table may include a set of entries, each of which corresponds to a sparse indicator. A sparse indicator may be identified (for example) by a position and identifier or by a range of positions and type of sparse identifier (e.g., type of structural sparse identifier and/or one or more corresponding position ranges in a reference data set). For example, FIG. 8 illustrates stored data 825 arranged in a table or array, such that a value along a first dimension can represent an identifier detected in a client data set and a value along a second dimension can represent a position at which the identifier was detected. Elements that correspond to those in a reference data set need not have a value. Each of one or more other elements may include bucket-assignment data, which may identify a bucket to which the sparse indicator is to be assigned and, in some instances, a confidence of such assignment. In some instances, one or more elements indicate that bucket-assignment data is not yet available).

The depicted stored data 825 may be useful for identifying bucket-assignment data for sparse indicators corresponding to differences between a client data set and reference data set at individual positions. It will be appreciated that additional stored data 825 may identify bucket-assignment for other types of sparse indicators (e.g., structural sparse indicators), such as a sparse indicator that indicates that elements from Position X to Position Y are not present in a client data set.

If a look-up of a particular sparse indicator is successful, look-up engine 830 may proceed to assign the sparse indicator in accordance with the bucket-assignment data. If a look-up of the particular sparse indicator is not successful or if a work flow calls for additional stages, the information associated with the sparse indicator and/or the result(s) from the look-up may be directed to data processor 840.

Look-up engine 830 may further allow for filtering of sparse indicators, such as to determine when a reviewer-assisted analysis of a particular sparse indicator is not needed or not to be performed. For example, some sparse indicators may be pre-assigned to particular data bucket(s) and look-up engine may identify these sparse indicators as such. In another example, some sparse indicators may not be suitable for an iterative analysis and/or may be predetermined such that no resources are to be used in analyzing the sparse indicator. For example, some sparse indicators are associated with a position in a full data set for which analysis is determined to be unnecessary. Optionally, some sparse indicators are associated with a position in a full data set and value for which analysis is determined to be unnecessary.

System 800 further includes a data processor 840, which may perform iterative performance of automated processing for each of the sparse indicators in data stream 820. It will be appreciated that more data processors 840 may be included in system 800, such as to allow parallel and/or sequential work flow performance. Data processor 840 may perform fully automated processing of stages of a work flow and forward stage result(s) to bucketor 855 for data bucket assignment.

In some embodiments of automated processing for one or more sparse indicators, data processor 840 may encounter one or more stages having a stage-progression condition that is not satisfied or may determine that a reviewer-engagement condition is satisfied (e.g., due to a failure to identify a bucket for a sparse indicator in a look-up data store or due to determining that a bucket assignment for a sparse indicator is associated with a confidence metric that is below a predefined quantitative or qualitative threshold). Optionally, data processor 840 may generate and transmit a query communication 845 that includes one or more of a position associated with a sparse indicator, one or more values associated with the sparse indicator, and a result(s) from a previous stage of the work flow. The query communication 845 may be transmitted, for example, from system 800 to an evaluation device 170 to facilitate review and/or input by evaluator 175. For example, evaluation device 170 may receive the query communication 845 and display the included information to allow the evaluator 175 to provide response data to satisfy the stage-progression condition. Evaluation device 170 may then generate a response communication 850 that includes response data. Data processor 840 may receive response communication 850 and use the included response data to complete or augment the automated processing to generate stage result(s). Once the stages are completed according to the work flow, stage result(s) may be forward to bucketor 855.

System 800 further includes bucketor 855, which may assign each sparse indicator to a bucket of a plurality of data buckets, such as by using stage result(s) from data processor 840 and/or look-up result(s) from look-up engine 830. Bucketor 855 may then assign a particular data bucket for the particular sparse indicator being analyzed. It will be appreciated that more bucketors 855 may be included in system 800. In system 800, five data buckets 860, 862, 864, 866, and 868 are depicted, though it will be appreciated that more or fewer data buckets may be utilized. Some or all of data buckets 860-868 may, for example, span a range along a spectrum of a degree of likeliness that a client will transition into or experience a particular state. Upon full or partial completion of the assignment of the sparse indicators in data stream 820 to data buckets, information may be passed to bucket assessor 870. It will be appreciated that counts assigned to a set of buckets may be determined with respect to each of multiple position ranges (or units) or combinations thereof. For example, for a given data set, a count may be generated for each of a set of buckets and for each of a set of units that reflects a number of sparse indicators detected for the unit that correspond to the bucket.

System 800 further includes bucket assessor 870. Although bucket assessor 870 is shown schematically as a separate component from bucketor 855, it will be appreciated that bucket assessor 870 and bucketor 855 may be combined in a single component or process. Bucket assessor 870 may identify a number of sparse indicators assigned to particular buckets 860-868 using one or more counters, for example. Bucket assessor 870 may optionally determine whether one or more buckets include counts above a predetermined threshold (e.g., whether a count exceeds zero). The predetermined threshold may be (for example) defined by a user, generated based on machine learning, generated based on a virtual structural representor, and/or generated based on a population analysis. For example, in one instance, it may be determined whether a count in a given bucket or a total count across a combination of buckets (e.g., a bucket corresponding to a highest predicted likelihood, amongst the buckets, of transitioning into or being in a particular state or two buckets corresponding to the two highest predicted likelihoods) exceeds zero. It will be appreciated that predetermined thresholds for each data bucket may be independent of other predetermined thresholds. Bucket assessor 870 may forward the counts corresponding to the buckets 860-868 to signal generator 875.

A signal generator 875 may use the counts and/or results of a threshold comparison, for example, to generate a communication 880 indicative of whether a number of sparse indicators assigned to particular data buckets exceed the predetermined threshold(s). In some embodiments, different templates for communication 880 may be used depending on which data bucket(s) exceed the predetermined threshold(s) and or by how much a threshold(s) is exceeded, for example. Communication 880 may identify, for example, whether one or more sparse indicators are assigned to a bucket representing a highest probability, amongst the buckets, of transitioning into or being at a particular state. Communication 880 may identify, for example, whether one or more sparse indicators are assigned to each of one or more other buckets.

Figure 9:
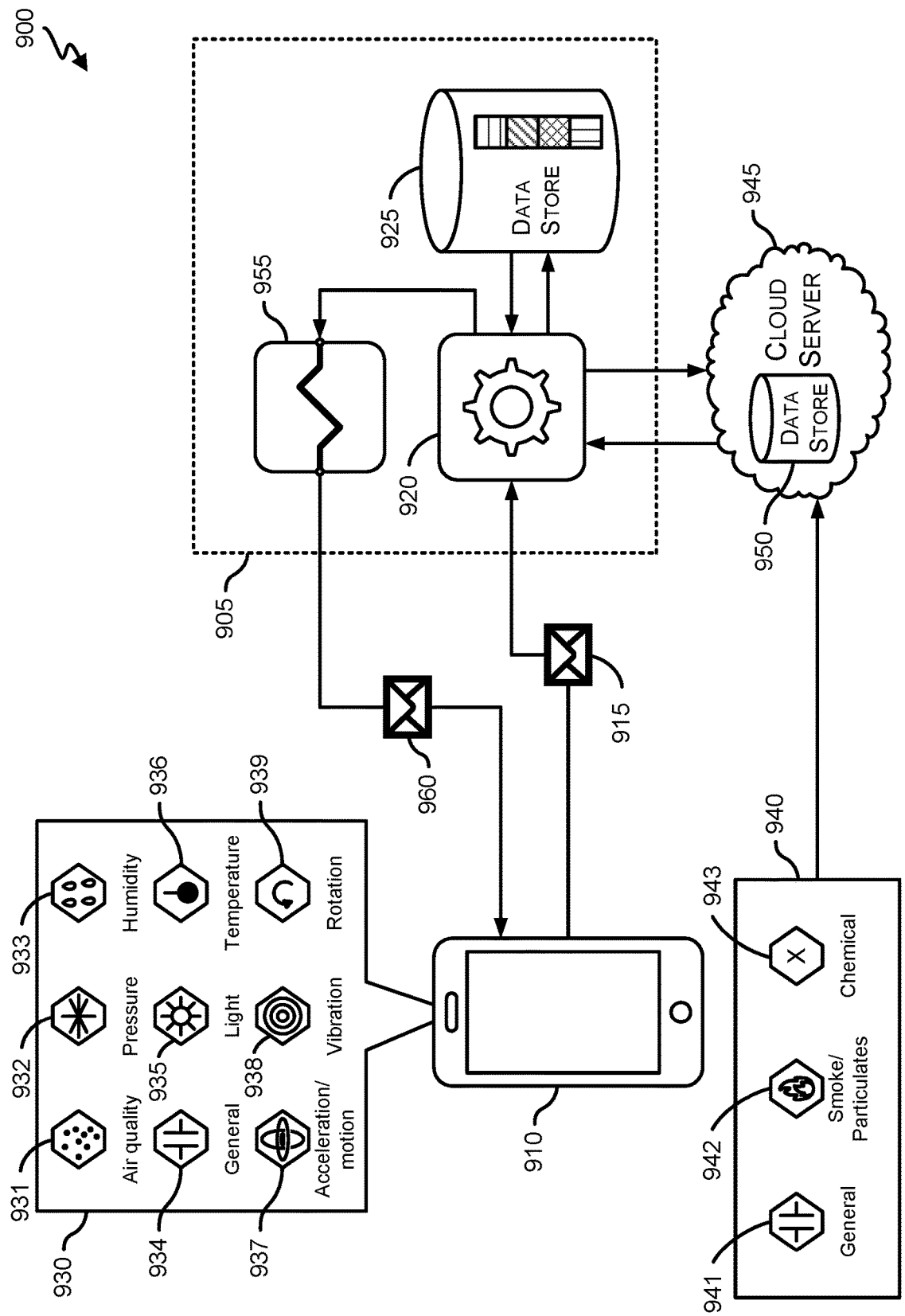
FIG. 9 shows a representation of a system for generating communications using sparse indicator information and sensor data.

Referring next to FIG. 9, a representation of a system 900 for analyzing sparse indicator information and sensor data is shown. System 900 may represent portions of assessment network 100 or 300 and may, for example, include additional or fewer elements than indicated in FIG. 9. System 900 may be in data communication with one or more other components of assessment network 100 or 300 not shown in FIG. 9, such as requestor device 110a or 110b, one or more facilities 120, one or more data generators 140, and/or one or more data stores 372, for example.

System 900 includes an assessment system 905 and client device 910. Client device 910 may generate and transmit an analysis request 915 to assessment system 905 to initialize determination of a status analysis for a client using sparse indicator information associated with the client and sensor data associated with the client. Analysis request 915 may be received at a data processor 920 of assessment system 905. Data processor 920 may query a data store 925 to obtain the sparse indicator information associated with the client. It will be appreciated that data processor 920 may first determine an identifier associated with the client in order to obtain the sparse indicator information associated with the client from the data store 925.

Assessment system 905 may also receive data from one or more sensors 930 associated with the client, such as at data processor 920, for use in the assessment analysis. For example, the sensor data may correspond to environmental sensor data, chemical sensor data, and/or motion or accelerometer data that may impact an analysis of a likelihood determination for a client transitioning to a particular state, for example.

Sensor data may also include information about or indicative of a current quality (e.g., a state, or condition) of a client or may be used to determine a current quality of a client. For example, the sensor data may provide or correspond to a marker or indicator identifying a current quality of a client, such as an indication of whether a particular marker is present or absent in a fluid associated with a client, such as a hormone, metabolite, chemical, structure, toxin, protein, etc. The sensor data may optionally be quantitative and the associated quality may also relate to a level or degree or amount of the marker detected. The quality may relate to, for example, a range of progression of a state or condition. In some embodiments, the sensor data may be compared with one or more thresholds indicating different quality levels and the current quality of the client may be assigned to a particular quality level based on the sensor data.

Sensor data may be used in the assessment analysis in a variety of ways. As one example, the sensor data may be used to estimate exposure of the client to a particular element, and this exposure may have a known association with a higher or lower likelihood of transitioning to a particular state and therefore impact the generated likelihood for a client transitioning to the particular state. Optionally, a current quality of a client may relate to a higher or lower likelihood of transitioning to a particular state and therefore impact the generated likelihood for a client transitioning to the particular state. In some embodiments, the data processor 920 may compute a first likelihood using only the sparse indicator information and also compute a second likelihood using both the sparse indicator information and the sensor data. The data processor 920 may also compute a change in likelihood between the first likelihood and the second likelihood, which may be attributable, at least in part, to the sensor data. Continued readings or receipt of sensor data may allow for updated likelihoods to be determined.

Sensors 930 may optionally be integrated directly into client device 910. Example sensors associated with the client are depicted in FIG. 9. For example, client device 910 may include one or more air quality sensors 931, pressure sensors, 932, humidity sensors 933, general sensors 934, light sensors 935, temperature sensors 936, acceleration or motion sensors 937, vibration sensors 938, or rotation sensors 939. It will be appreciated that general sensor 934 may represent any other sensor not specifically described here that may be incorporated into client device 910 and that more or fewer sensors may be incorporated into client device 910. Optionally, sensor data from the one or more sensors of client device 910 may be communicated to assessment system 905 by inclusion in analysis request 915. Optionally, sensor data from the one or more sensors of client device 910 may transmitted separately. For example, sensor data may be pushed to assessment system 905 directly by client device 910. As another example, sensor data may be pulled by assessment system 905, such as by way of one or more query/response communication exchanges.

System 900 may also include a standalone sensor device 940 that may also provide sensor data to assessment system 905 data processor 920. As an example, standalone sensor device 940 illustrated in FIG. 9 may include one or more general sensors 941, smoke and/or particulate sensors 942, and chemical sensors 943. It will be appreciated that more or fewer sensors may be included in standalone sensor device 940 and that general sensor 941 may represent any other sensor or sensor type that may be incorporated into a standalone sensor device 940. It will further be appreciated that multiple and/or different standalone sensor devices 940 may be incorporated into system 900.

Standalone sensor device 940 may also provide sensor data to assessment system 905. As illustrated in FIG. 9, standalone sensor device 940 may provide the sensor data to a cloud server 945 for relaying to assessment system 905. Cloud server 945 may include a data store 950 for storage of sensor data received from standalone sensor device 940. It will be appreciated that data from sensors 931-939 may also be optionally transmitted by client device 910 to cloud server 945 for optional storage by data store 950 and relay to assessment system 905. Sensor data collected by standalone sensor device 940 may, however, instead be provided directly to assessment system 905 by a data push or a data pull communication.

Once data processor 920 possesses the sparse indicator data, the data processor may analyze or characterize the sparse indicator information, such as by way of one more bucketing processes, such as depicted with respect to FIG. 8. Possession of the sensor data from client device 910 and/or standalone sensor device 940 may allow the data processor 920 to further characterize a state or status of the client associated with the client device 910.

The analysis result(s) may be forwarded to a signal generator 955, which may use the analysis result(s), for example, to generate a communication 960 indicating one or more likelihoods for the client to transition to the particular state. In some embodiments, communication 960 may also identify a change in likelihood, relevant sensor data and/or sparse indicator information that contributed to the likelihood analysis.

Figure 10:
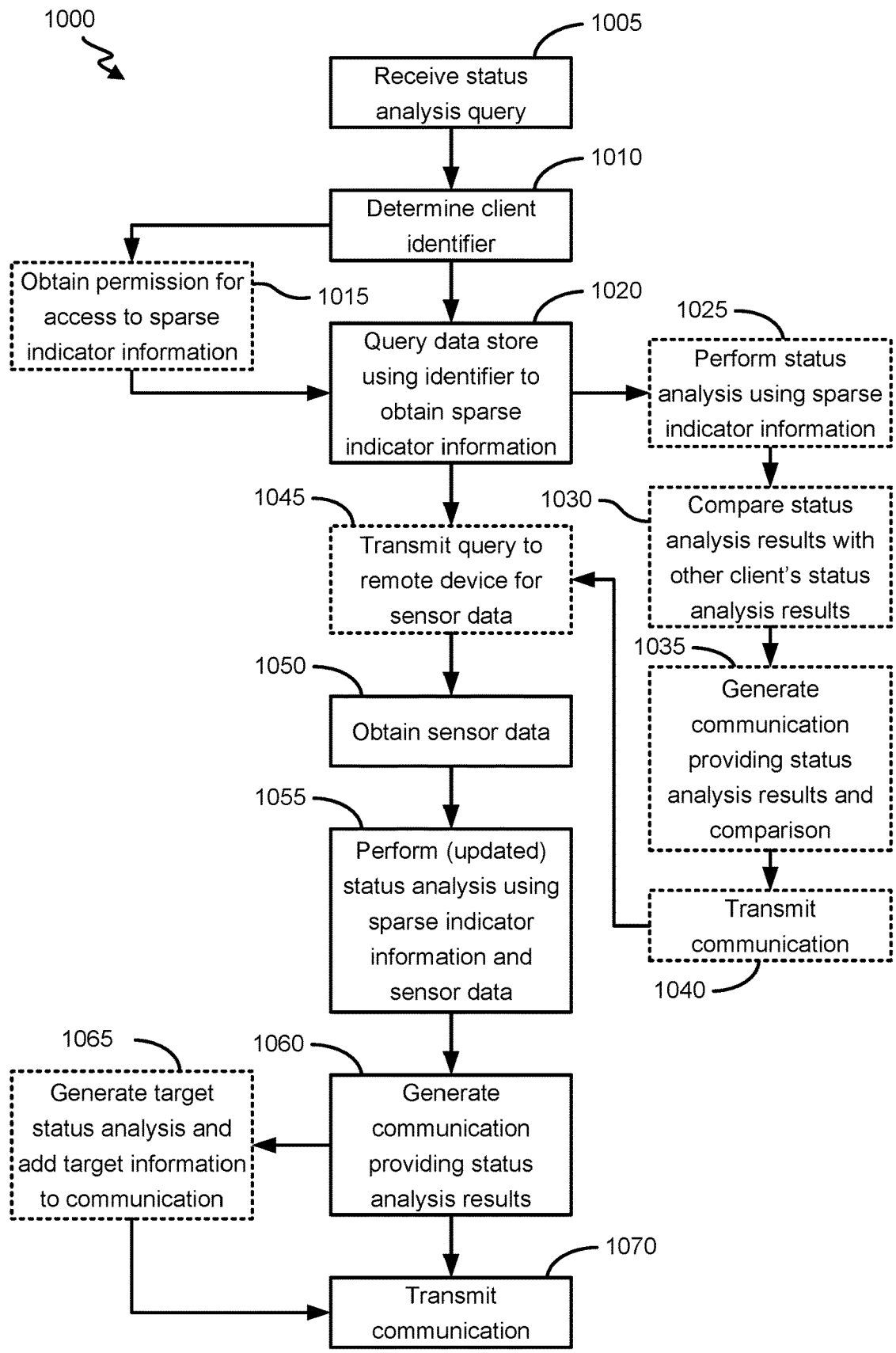
FIG. 10 shows a representation of a process for generating communications using sparse indicator information and sensor data.

FIG. 10 shows a representation of a process 1000 for generating communications using sparse indicator information and sensor data. Initially, at block 1005, a status analysis query may be received, such as by an assessment system. Status analysis query may correspond to an instruction from a client or requestor to perform a status analysis on behalf of or corresponding to a client.

At block 1010, a client identifier may be determined. Optionally, the client identifier may be directly obtained from the status analysis query. Optionally, the client identifier may be obtained by performing a look-up in one or more data stores or databases. The client identifier may be useful, for example, for later identifying other data, such as sparse indicator information and/or sensor data associated with the client.

Optionally, at block 1015, permission for accessing sparse indicator information for the client may be obtained, such as by transmitting a request for authorization and receiving authorization information. For example, the request may be generated by an assessment system and transmitted to a client device or a requestor device for access permission. Upon receiving the request, the client device or requestor device may obtain authorization, such as via one or more inputs corresponding to the authorization, for access by the assessment system to the sparse indicator information.

At block 1020, a database or data store is queried to obtain sparse indicator information associated with the client. For example, the client identifier determined at block 1010 may be used to facilitate obtaining the sparse indicator information, such as by including the client identifier in the query. If required, authorization information obtained at block 1015 may be included in the query to the database or data store.

Optionally, an initial status analysis may be performed using the sparse indicator information, such as indicated in FIG. 10 at block 1025. The initial status analysis may correspond, for example, to an initial status analysis performed without use of sensor data.

The status analysis results so obtained may optionally be compared, at block 1030, with one or more other client's status analysis results. Optionally, the one or more other client's status analysis results correspond to an aggregated status analysis results. For example, an average, median, or mode likelihood of all clients having status analyses performed may be used as the aggregated status analysis result. As another example, the aggregated status analysis result may correspond to an average, median, or mode likelihood of clients sharing one or more characteristics with the client for which the present analysis is being performed.

At block 1035, a communication providing the initial status analysis result and results of the comparison may optionally be generated. At block 1040, the communication providing the initial status analysis result and results of the comparison may be transmitted. Optionally, the initial status analysis result and results of the comparison may be stored without transmission at this point and retrieved at a later time point for transmission. For example, the initial status analysis result and results of the comparison may be retrieved and added to a later status analysis communication transmission.

At block 1050, sensor data may be obtained. Without limitation, the sensor data obtained may correspond to one or more of chemical sensor data, potentiometric sensor data, solute sensor data, microfluidic sensor data, environmental sensor data, activity sensor data, accelerometer data, altitude sensor data, biometric sensor data, location sensor data, weather sensor data, biometric sensor data, biomarker sensor data, pH sensor data, cytometric sensor data, optical sensor data, smoke detector data, particulate sensor data, electrical current sensor data, electrical resistance sensor data, and electrical impedance sensor data. It will be appreciated that other sensor data not enumerated here may be obtained. The sensor data obtained may be associated with the client. For example, the sensor data may be obtained using one or more sensors incorporated into a client device, such as a wearable device, or using one or more sensors associated with a location of the client. The sensor data may be obtained at block 1050 in response to an optional transmission of a query, as indicated by block 1045, to a remote device for the sensor data. The sensor data may provide an indication of a current quality of the client. For example, the sensor data may provide information regarding one or more solutes used to identify or indicate a state of the client. In some embodiments, the solute may be present on a surface of the client or in a fluid obtained from the client.

At block 1055, an (updated) status analysis is performed using the sparse indicator information obtained at block 1020 and the sensor data obtained at block 1050. The (updated) status analysis may provide information relative to a likelihood of the client for transitioning to a particular state based on the sparse indicator information and the sensor data. Optionally, a comparison may be made between the results of the status analysis performed at block 1025 and the (updated) status analysis performed at block 1055. In this way, the impact of the sensor data on the status analysis can be directly determined via the comparison.

At block 1060 a communication is generated providing, at least, the results of the (updated) status analysis. If an initial status analysis was performed at block 1025, the result of this initial status analysis may optionally be included in the communication. Optionally, sensor data may also be included in the communication.

Optionally, at block 1065, a target status analysis may be generated, such as will be described below with reference to FIG. 11. Target status analysis may be generated using one or more of sparse indicator information obtained at block 1020, sensor data obtained at block 1050, and analysis results generated at block 1055, and information related to the target status analysis may be added to the communication generated at block 1060. For example, the results of the target status analysis may be added to the communication. As another example, target sensor data that may be identified in a process of determining the target status analysis may be added to the communication.

At block 1070, the communication may be transmitted. For example, the communication may be transmitted to a client device and/or to a requestor device. It will be appreciated that blocks 1050-1070 may be repeated one or more additional times, such as on a periodic or aperiodic basis, as updated sensor data is obtained.

Figure 11:
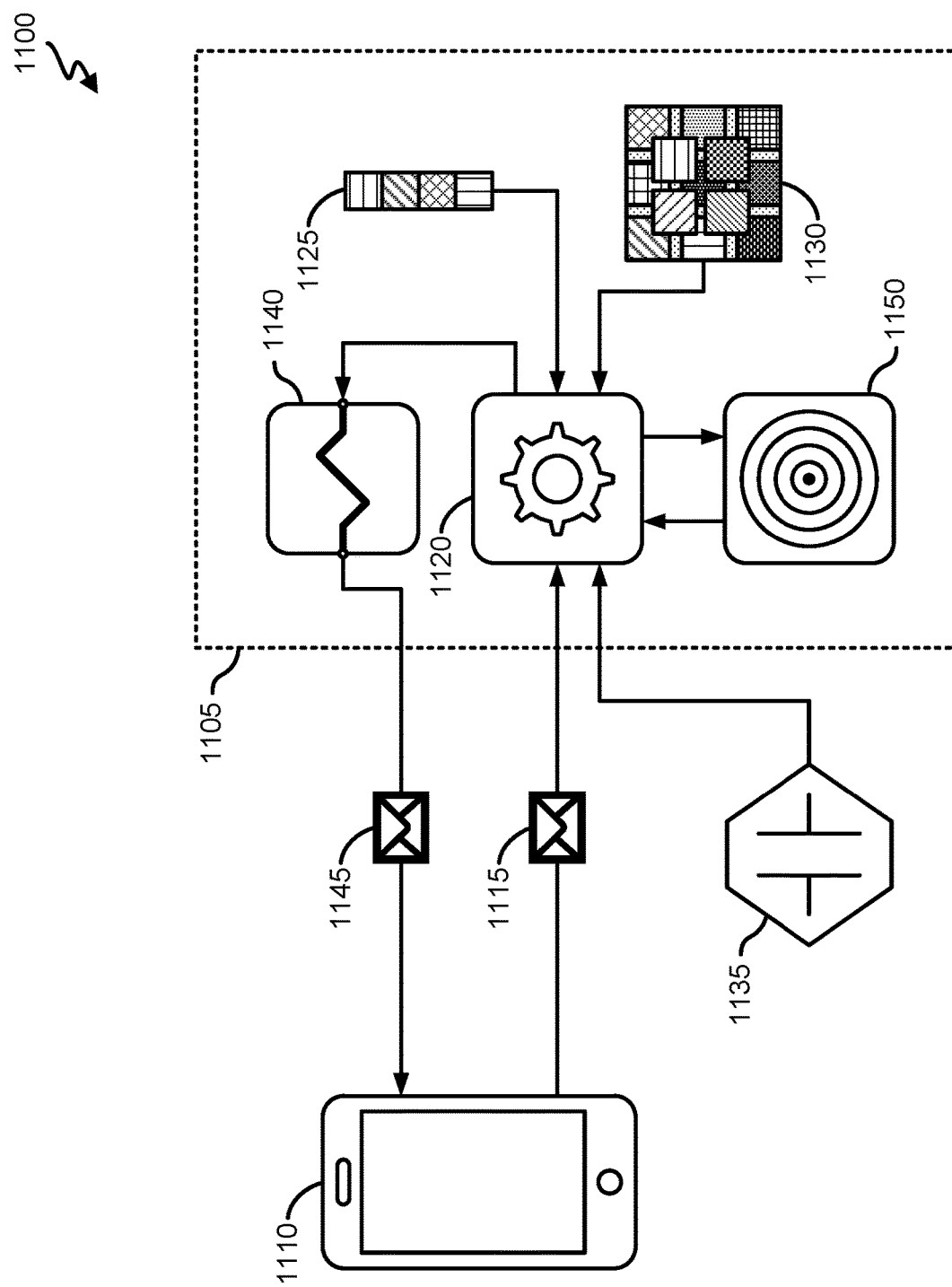
FIG. 11 shows a representation of a system for generating communications including target information using sparse indicator information and sensor data.

Referring next to FIG. 11, a representation of a system 1100 for analyzing sparse indicator information and sensor data is shown. System 1100 may represent portions of assessment network 100 or 300 and may, for example, include additional or fewer elements than indicated in FIG. 11. System 1100 may be in data communication with one or more other components of assessment network 100 or 300 not shown in FIG. 11, such as requestor device, one or more facilities, one or more data generators, and/or one or more data stores, for example.

System 1100 includes an assessment system 1105 and client device 1110. Client device may generate and transmit an analysis request 1115 to assessment system 1105 to initialize determination of a status analysis for a client using sparse indicator information associated with the client and sensor data associated with the client. Analysis request 1115 may be received at a data processor 1120 of assessment system 1105, for example. Data processor 1120 may query a data store to obtain the sparse indicator information 1125 associated with the client. The data processor 1120 may use the sparse indicator information 1125 in the performance of a status analysis to determine a likelihood for the client of transitioning into a particular state.

Data processor may also query the data store to obtain aggregated information 1130, which may be associated with or related to sparse indicator information for a plurality of other clients. For example, aggregated information 1130 may include sparse indicator information for the plurality of other clients and then the sparse indicator information for the plurality of other clients may be used in analyses to determine likelihoods for the plurality of other clients of transitioning into the particular state. The determined likelihoods for the plurality of other clients may then be aggregated (e.g., averaged) and used in a comparison of the likelihood determination for the client of transitioning into the particular state. As another example, aggregated information 1130 may correspond directly to the aggregated likelihood. In these ways, the client may be able to see how they compare with another population. In one embodiment, the plurality of other clients share one or more characteristic(s) with the client.

Assessment system 1105 may also receive sensor data from sensor 1135, which may be forwarded directly and/or automatically from sensor 1135 to data processor 1120 in a sensor data push configuration. Although illustrated in FIG. 11 as a separate sensor, sensor 1135 may optionally be integrated into client device 1110, similar to sensors 930 depicted in FIG. 9.

It will be appreciated that, in some embodiments, client device 1110 may include or have installed thereon software applications for interfacing with sensor 1135 or otherwise facilitating the collection of sensor data from sensor 1135. In some embodiments, a first software application is installed on client device 1110 for generating analysis request 1115 and a second software application is installed on client device 1110 for obtaining sensor data from sensor 1135. Optionally, a third software application is installed on client device 1110 for forwarding of facilitating forwarding of sensor data from sensor 1135 to assessment system 1105. Optionally, forwarding or facilitating forwarding of sensor data from sensor 1135 to assessment system 1105 includes forwarding sensor data from sensor 1135 to assessment system by way of one or more intermediate networked systems, such as a cloud server.

Optionally, sensor data from sensor 1135 may be obtained by assessment system 1105 in a data pull configuration. For example, data processor 1120 may transmit a sensor data query to sensor 1135 or a system associated with sensor 1135, such as a cloud server that stores data generated by sensor 1135 or client device 1110, etc., and the sensor data may be transmitted to data processor 1120 in response to the sensor data request. A sensor data query may include information associated with the particular client, such as an identifier associated with the particular client, in order to allow the appropriate sensor data generated by sensor 1135 to be returned to assessment system 1105, such as in a configuration where a cloud server stores sensor data associated with a plurality of individuals. In some embodiments, permission or authorization for access to sensor data may be requested and provided to sensor 1135 or a system associated with sensor 1135 to ensure security and appropriate access to the sensor data.

Data from sensor 1135 may be used with sparse indicator information 1125 by data processor 1120 in a status analysis to determine a likelihood for the client transitioning to a particular state. The analysis result(s) and aggregated likelihood, for example, may be forwarded to a signal generator 1140, which may use the analysis result(s) and aggregated likelihood information to generate a communication 1145 indicating one or more likelihoods for the particular client to transition to the particular state and comparing with aggregated likelihoods. Optionally, communication 1145 may include sensor data obtained by sensor 1135.

FIG. 11 also depicts a target generator 1150, which may use sparse indicator information, sensor data from sensor 1135, and analysis results from a status analysis in determination of one or more targets. Optionally, targets may include, for example, target likelihoods for transitioning to a particular state. Optionally, targets may include, for example, target sensor data. Optionally, targets may facilitate the client changing behavior or exposure to impact a likelihood of transitioning to a particular state.

Target generator 1150 may optionally obtain sparse indicator information and/or analysis results from data processor 1120. In addition, target generator 1150 may obtain sensor data from sensor 1135 or a system associated therewith using a data push or data pull configuration. Optionally, sensor data may be provided to target generator 1140 by data processor 1120.

Target generator 1150 may use all, none, or portions of the sparse indicator information 1125, sensor data from sensor 1135, and analysis results generated by data processor 1120 in generating targets. For example, it may be desired to generate a target likelihood of a client transitioning to a particular state, and this target likelihood may be identified, at least in part, by changing one or more parameters sensed by the sensor 1135. In this way, target generator may generate one or more target likelihoods and obtain recommended changes (i.e., target sensor data) for achieving the target likelihoods. As an example, air quality data may be obtained by sensor 1135, and target generator 1150 may generate a target air quality metric in tandem with determination of a target likelihood that is impacted by particular sensor data that may be obtained by sensor 1135. Targets generated by target generator 1150 may also correspond to actions or behaviors to be performed by a client. For example, different motion amounts of the client may correspond to different likelihoods of the client transitioning to a particular state and so a target motion sensor value may be identified to facilitate achieving the target likelihood.

In a particular embodiment, the target(s) may be associated with actions that may affect a change in the likelihood of transitioning to a particular state. In some embodiments, the targets may correspond to or be associated with actions for increasing the likelihood of transitioning to a particular state. In some embodiments, the targets may correspond to or be associated with actions for decreasing the likelihood of transitioning to a particular state.

Optionally, sensor 1135 may be used to measure whether particular targets are met or unmet by the client. For example, motion data obtained by an accelerometer may be used by target generator 1140 in assessing whether a motion target for the client is met or unmet. In some embodiments, information regarding whether a target is met or unmet may be used in performing a further status analysis corresponding to a determination of a likelihood of the client transitioning to a particular state.

Figure 12:
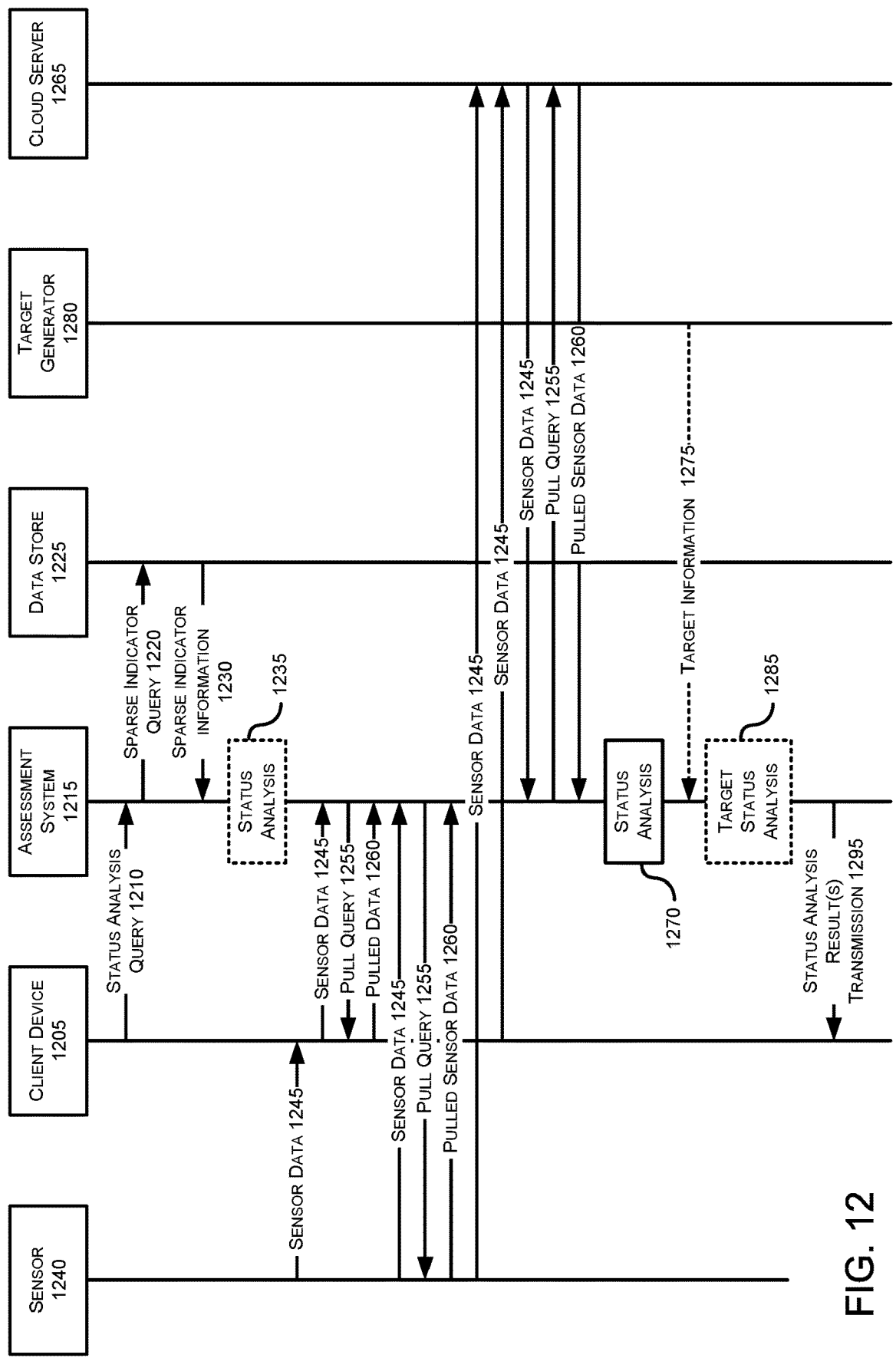
FIG. 12 shows a communication exchange between systems and devices of a data processing network, in accordance with some embodiments.

FIG. 12 shows a communication exchange between systems and devices of a data processing network, in accordance with some embodiments. For example, a client device 1205 may generate a status analysis query 1210 that is received by an assessment system 1215. In order to perform the requested status analysis, assessment system may use sparse indicator information. In some embodiments, the sparse indicator information is immediately available at assessment system 1215. If the sparse indicator information is not available, assessment system 1215 may generate and transmit a sparse indicator query 1220 to a data store 1225 or a system associated with the data store. In response, the sparse indicator information 1230 may be transmitted to assessment system. Optionally, assessment system 1215 may perform a status analysis 1235 using only the sparse indicator information 1230.

To perform a further status analysis, assessment system 1215 may use data from sensor 1240. Sensor data 1245 from sensor 1240 may be provided to assessment system 1215 in a variety of ways. For example, sensor 1240 may obtain and provide sensor data 1245 to client device 1205. Client device may then push sensor data 1245 to assessment system 1215. Alternatively, assessment system 1215 may generate and transmit a sensor data pull query 1255 to client device and receive the pulled sensor data 1260 in response. As another example, sensor 1240 may push sensor data 1245 directly to assessment system 1215. Alternatively, assessment system 1215 may generate and transmit a sensor data pull query 1255 to sensor 1240 and receive the pulled sensor data 1260 in response. As another example, sensor 1240 or client device 1205 may transmit sensor data 1245 to a cloud server 1265, such as by way of one or more data push or data pull processes. Assessment system 1215 may receive sensor data 1245 pushed from cloud server 1265. Alternatively, assessment system 1215 may generate and transmit a sensor data pull query 1255 to cloud server 1265 and receive the pulled sensor data 1260 in response. It will be appreciated that sensor data 1245 from sensor 1240 may also be obtained by assessment system 1215 by other techniques.

After obtaining sensor data 1245 from sensor 1240, assessment system may perform a status analysis 1270 using the sparse indicator information 1230 and the sensor data 1245. It will be appreciated from the foregoing disclosure that the status analysis 1270 and status analysis 1235 may include a likelihood of the client transitioning to a particular state. In addition, a comparison may be made between the results of status analysis 1270 and the status analysis 1235 to determine an impact of the sensor data 1245 on the likelihood of the client transitioning to a particular state.

Target information 1275 may optionally be generated by target generator 1280 and communicated to assessment system or a portion thereof for use in a target status analysis 1285.

Finally, a status analysis result(s) transmission 1290 may be generated by assessment system 1215 and sent to client device 1205. It will be appreciated that the status analysis result(s) may correspond to results of status analysis 1235, status analysis 1270 and/or target status analysis 1285.

Figure 13:
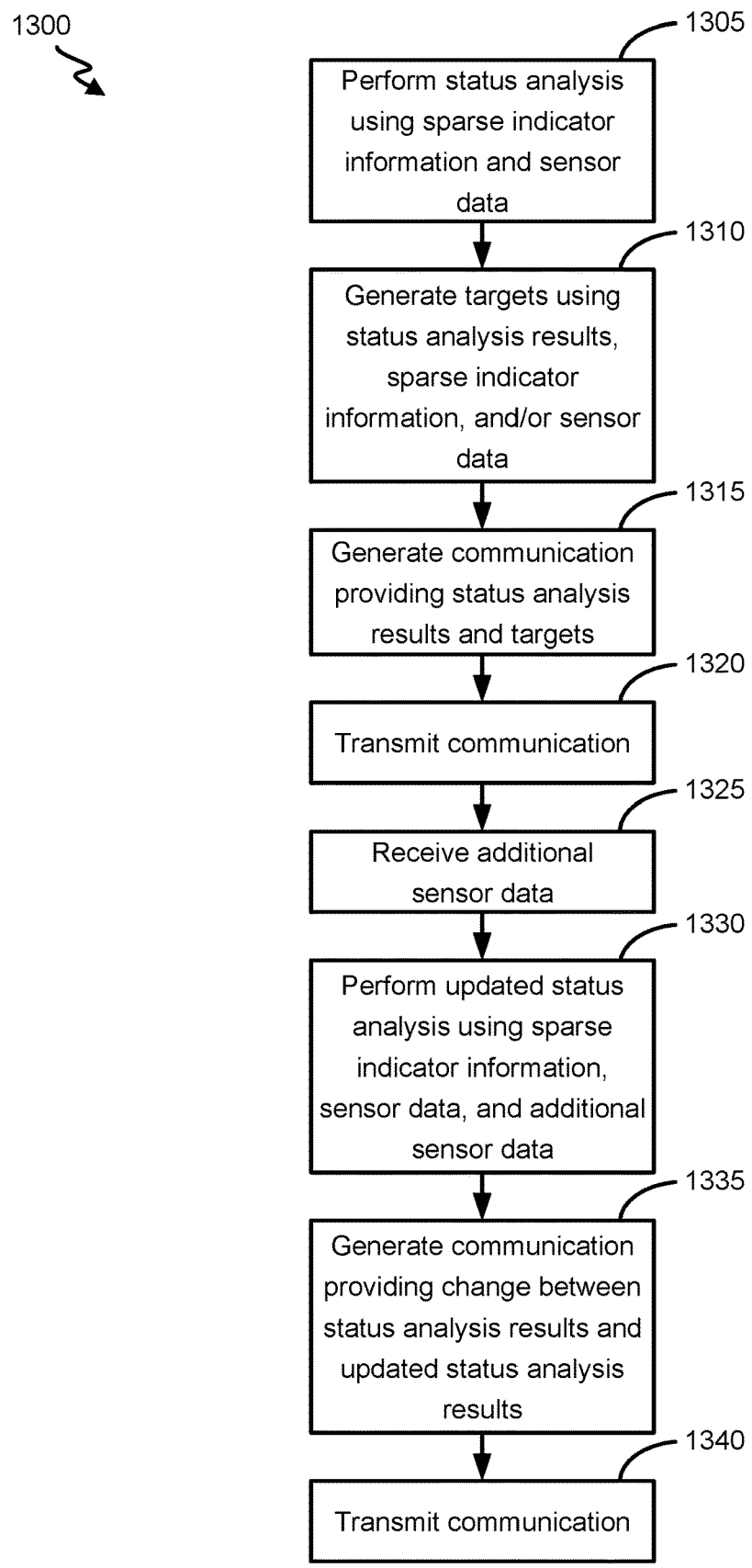
FIG. 13 shows a representation of a process for generating communications including target information using sparse indicator information and sensor data.

FIG. 13 shows a representation of a process 1300 for generating communications including target information using sparse indicator information and sensor data. Initially, at block 1305, a first status analysis is performed using sparse indicator information and sensor data, such as described above with reference to FIG. 9.

At block 1310, targets may be generated using one or more of the status analysis results, sparse indicator information, and sensor data, such as described above with reference to FIGS. 10-12.

At block 1315, a first communication may be generated providing at least the status analysis results and the targets. Optionally, the first communication may include information related to the sensor data and the sparse indicator data. The first communication may optionally provide a comparison of status analyses performed using only the sparse indicator information, both the sparse indicator information and the sensor data, and of a target status analysis.

At block 1320, the communication may be transmitted. Depending on the entity requesting the status analysis and the particular status analysis request, the communication may be transmitted to one or more devices, such as a device associated with a requestor, a device associated with a client, a device associated with a facility, etc.

Target(s) may be used by clients, for example, to facilitate modification of behaviors or to facilitate performing actions that may impact a likelihood for transitioning to a particular state. For example, the target(s) may correspond to an instruction for a client to follow. In order to determine whether the target(s) have been met or unmet by the client, sensor data related to the target(s) may be used. For example, sensors may be possessed by the client or located at a same location as the client or may monitor various characteristics of the client and may aid in determining whether the target(s) have been met or unmet. For example, if a target corresponds to a particular action, a sensor that monitors that particular action may provide informative data regarding the target. As a specific example, if a target corresponds to an instruction for a client to reduce an exposure to particulates (e.g., smoke), data from a particulate sensor monitoring an area occupied by the client may provide insights as to whether the client is following the instruction.

At block 1325, additional sensor data is received, such as sensor data related to the targets or sensor data relating to or providing an indication of an updated state of the client. Optionally, the sensor data related to the targets may be directly received. Optionally, the sensor data related to the targets may be received in response to a query for the sensor data, as described above. Optionally, the sensor data may be received directly from the sensor that generated the sensor data. Optionally, the sensor data may be received from a client device associated with or including the sensor. Optionally, the sensor data may be received from a cloud server.

At block 1330, an updated status analysis may be performed using one or more of the sparse indicator information, the sensor data used in block 1305, and the additional sensor data, such as sensor data related to the targets or sensor data relating to an updated state of the client received at block 1325. This status analysis may be compared with a previous status analysis generated using the sparse indicator information and previous sensor data. The status analysis may optionally be compared with a previous target status analysis.

At block 1335, an updated communication may be generated providing at least the updated status analysis results. Optionally, the updated communication may include information related to the update sensor data, the sparse indicator information, and the sparse indicator data. At block 1320, the communication may be transmitted. Depending on the entity requesting the status analysis and the particular status analysis request, the communication may be transmitted to one or more devices, such as a device associated with a requestor, a device associated with a client, a device associated with a facility, etc.

It will be appreciated that receiving updated sensor data related to the targets may allow for tracking of whether the targets have been met or unmet. Further, receiving the updated sensor data may also allow for reevaluation of the likelihood of the client transitioning to a particular state based on the updated sensor data. This reevaluation may facilitate the client determining whether progress towards the target is being achieved and/or whether the target is further away in view of the updated sensor data.

Figure 14:
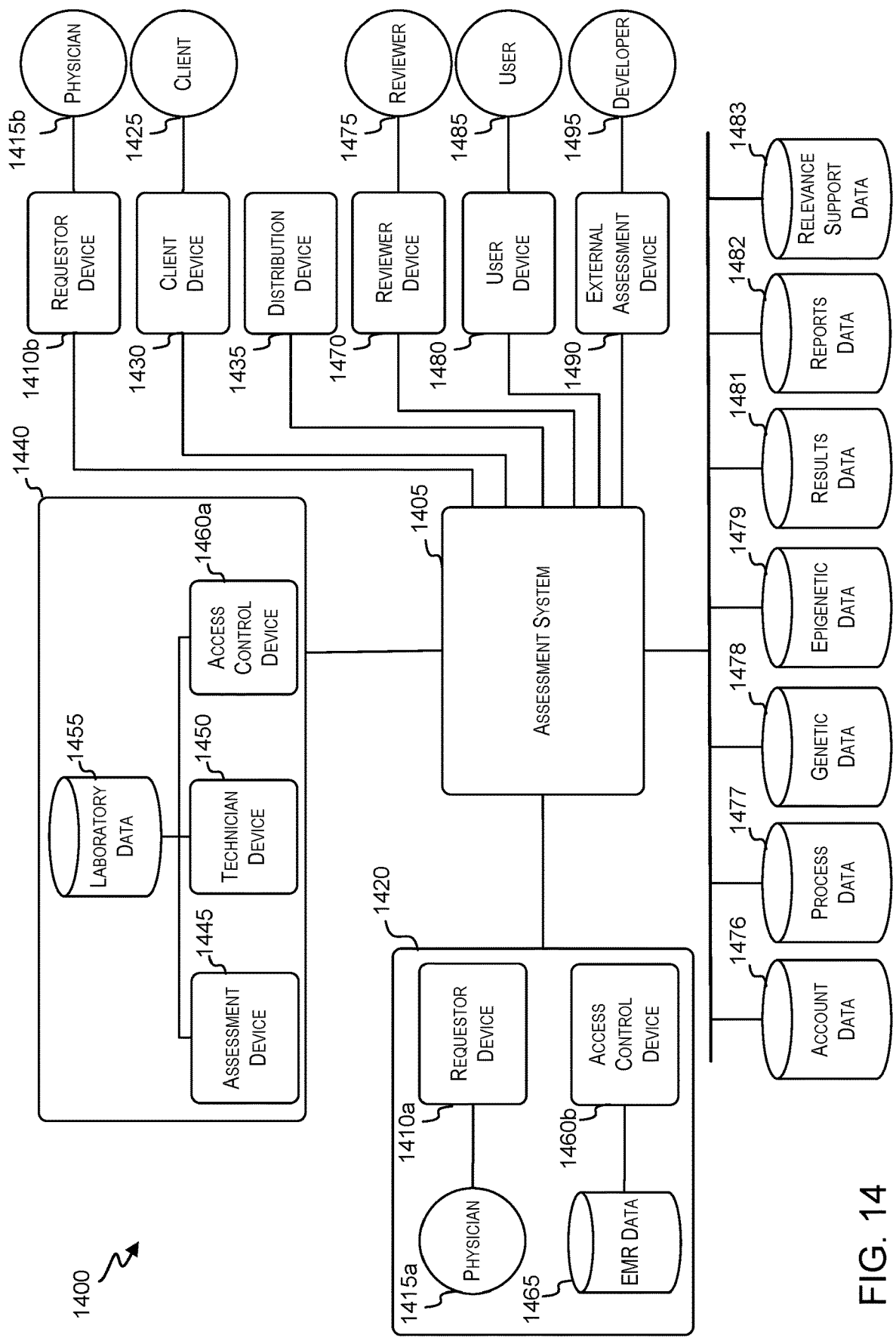
FIG. 14 shows a representation of a genetic assessment network, in accordance with some embodiments.

Referring next to FIG. 14, a genetic assessment network 1400 is shown in one embodiment. Through the interaction of multiple devices and entities, an assessment system 1405 can generate an output that includes a risk variable and/or risk assessment indicating an estimated risk of each of one or more particular conditions (e.g., breast cancer and ovarian cancer) for a particular individual (also referred to herein as a client or subject).

More specifically, assessment system 1405 receives an electronic request from a requestor device 1410. Assessment system 1405 may include one or more electronic devices (e.g., servers and/or computers) and may, but not need, reside partly or entirely at a remote server. Requestor device 1410 may be one configured and located to receive input from a physician 1415. In one instance, requestor device 1410a is located in an external physician-associated facility 1420, such as a physician's office or hospital. In one instance, requestor device 1410b includes an internally linked requestor device 1410b, such as ones that itself receive invitations, from assessment system 1405, to generate electronic requests.

The electronic request can include an order to conduct a genetic analysis and/or to conduct one or more types of risk assessments. The electronic request may identify, or otherwise indicate, one or more conditions to be evaluated during the genetic analysis and/or risk assessment. The electronic request may identify a patient and/or include additional data pertaining to the patient, such as identifying, health, and/or medication data of the patient.

The patient may be equated to, by assessment system 1405, a client 1425. In some instances, a client device—associated with client 1425—initially transmits a preliminary electronic request for the genetic analysis and/or risk assessment to assessment system 1405. For example, such a preliminary electronic request may be initiated via client interaction with a website associated with assessment system 1405. The same or a subsequent preliminary request may identify a particular physician (e.g., by name, office location, phone number, and/or email address) and/or may request that a physician 1415b associated with an internally linked requestor device 1410b submit such a request.

When a particular physician (or other medical entity) is identified in a preliminary electronic request, assessment system 1405 may identify a destination address (e.g., IP address or email address) associated with the physician and transmit a communication identifying information associated with the preliminary request (e.g., the client, a type of genetic analysis, and so on). The communication may include a partial order and/or an input field that would confirm that the order requested by client 1425 is to be generated and transmitted back to assessment system 1405. Such a communication may facilitate receipt of the electronic request from requestor device 1410b.

When it is requested that a physician 1410b associated with an internally linked requestor device 1410b submit such a request, assessment system 1405 may transmit a similar communication to a requestor device 1410b that may have been selected from amongst multiple internally linked requestor devices. The selection may be based on a load balancing technique, physician office hours, physician expertise, locations of the multiple requestor devices, a pseudo-random selection technique, and/or an insurance affiliation.

Once the electronic request has been received from a requestor device 1410 (e.g., in response to a preliminary electronic request from a client device 1430), assessment system 1405 may evaluate the electronic request to ensure that all required data (e.g., which may include a name, address, insurance, billing and/or payment information, such as credit card information) has been provided from physician 1415a and that all required data pertaining to client 1425 has been identified (e.g., via the electronic request, a preliminary request and/or stored data). If assessment system 1405 determines that all required information has not been identified, a request for such information may be transmitted to requestor device 1410 and/or client device 1430.

When all required information has been provided, assessment system 1405 can send an instruction communication to a distribution device 1435. The instruction communication can include (for example) a name and address of client 1425 and, in some instances, an indication as to what is to be sent to client 1425. For example, an electronic request may indicate a type of analysis that is to be performed on a biological sample (e.g., a genetic analysis pertaining to a risk of getting one or more particular types of cancers) and/or a type of biological sample (e.g., a saliva sample) that is to be analyzed. The instruction communication may identify the type of analysis, type of biological sample and/or kit associated with collection thereof. The instruction communication may thus facilitate and/or trigger a physical distribution of a kit for collecting a biological sample to a client address. The kit may include, for example, instructions as to how to collect a sample, a container for storing the sample, an envelope or package for sending the container and sample to be analyzed, and/or information pertaining to an order or type of analysis to be conducted.

A sample from client 1425 may then be received at a laboratory 1440. Laboratory 1440 may include one or more assessment devices 1445 configured to sequence all or part of the genome and/or all or part of the epigenome using the sample. For example, an assessment device 1445 may include a DNA sequencer and/or PCR machine. Laboratory 1440 may further include one or more technician devices 1450, such as a desktop or laptop computer. Data generated by or at one or more laboratory devices (e.g., assessment device 1445 or technician device 1450) may be stored at a laboratory data store 1455, which may be remote from all laboratory devices or part of a laboratory device. The laboratory data may, for example, include identifying client information (e.g., a name and address), laboratory information (e.g., location and name), device specifications (e.g., manufacturer and model of assessment devise) and genetic data (e.g., genetic sequences).

An access control device 1460a may control which devices and/or entities may gain access to the laboratory data, which may apply to devices and/or entities internal to laboratory 1440 and/or to devices and/or entities external to laboratory 1440. Access control device 1460a may implement one or more rules, such as restricting access to client data to one or more particular devices (e.g., associated with assessment system 1405). Such access may further or alternatively be controlled via logins, passwords, device identifier verification, etc.

In various instances, access control device 1460a controls access via control of pushed transmissions and/or via control of processing pull requests. For example, a rule may indicate that laboratory data pertaining to a sample is to be automatically be transmitted to a particular assessment system 1405 (and/or device associated therewith) upon completion of a laboratory-based assessment or detection of particular data (e.g., data matching a request). Access control device 1460a may then monitor for such a condition to be met and may then generate and transmit appropriate data.

In addition to receiving laboratory data, assessment system 1405 may further collect one or more other types of data that may be used to assess, for example, a health risk. For example, one other type of data may include health-related inputs provided at a client device 1430, such as inputs that indicate medical history, current conditions, familial health statuses or conditions, age, eating habits, exercise patterns, occupation, exposure to environments associated with toxic chemicals, and so on. Another type of data may include data automatically detected at a client device 1430. For example, a wearable client device may track activity patterns so as to estimate calories burned per day, or the wearable client device may estimate a pulse distribution, user temperature, sleep patterns and/or indoor/outdoor time. This data may be directly transmitted (e.g., after a request and/or authorization handshake) to assessment system 1405 and/or via another client device (e.g., via accessing health data on a phone or computer client device). Yet another type of data may include protected health information (PHI) data and/or electronic medical record (EMR) data, which may be stored, for example, at a EMR data store 1465 at and/or associated with an external physician-associated facility, such as one having provided an electronic request to perform an analysis or assessment pertaining to a client and/or one as identified via input at a client device 1430. To illustrate, the other data may identify one or more symptoms and/or physician evaluation results for a client or may include a result of one or more medical tests (e.g., mammogram, MRI, pulmonary function, EKG, etc.).

In various instances, the other data may be transmitted to assessment system 1405 prior to any, or in response to a, request from assessment system 1405 for such. For example, client input other data may be provided as part of a preliminary request from client device 1430 and EMR data may be provided as part of an electronic request from requestor device 1410a. As another example, upon receiving a preliminary request from a client device, assessment system

1405 may request that a client authorize access to health data stored on the client device, such that it may be (e.g., via an app) retrieved and transmitted to assessment system 1405.

Thus, assessment system 1405 may have access to—for a given subject—one or more genetic sequences, epigenetic modification data, client-reported data, medical record data, medical test data, activity (e.g., exercise) data, and/or other types of data. Assessment system 1405 may therefore evaluate genetic data in combination with other types of data in order to generate a risk analysis result. In one instance, an initial evaluation involves detecting whether, for each data type, the data includes an abnormal data element (e.g., as evaluated with respect to the human species or a particular population). For example, assessment system 1405 may identify whether genetic data includes any variants with respect to genes of interest, or assessment system 1405 further evaluate a medical history (e.g., as provided by a physician) to determine whether the client had a prior cancer diagnosis. As another example, a family history may be evaluated to determine whether an above threshold number of relatives were diagnosed with cancer or whether a close relative was diagnosed with cancer prior to a threshold age. As yet another example, data from a wearable device may be assessed to determine whether a client is not meeting a threshold for exercise and/or for sleep or to determine whether a client is outside more than a threshold percentage of time.

Each one of these abnormalities may be individually associated with some increased risk for being diagnosed with a condition, such as cancer. These associations may be identified via a local or remote look-up table. Assessment system 1405 may aggregate the data in any of a variety of manners. For example, assessment system 1405 may identify a maximum (quantitative or categorical) risk variable associated with each of two, more or all data types, or aggregate system 1405 may generate a weighted sum of risk variable. As another example, a protocol for how to generate an overall risk variable based on a combination of abnormality data based on a machine-learning or cluster protocol.

In some instances, a risk associated with a particular abnormality (e.g., variant) and/or with a combination of abnormalities is unknown or is associated with a below-threshold confidence. Upon detecting such an abnormality or combination (or a threshold quantity thereof), the particular abnormality and/or combination can be identified in a review-request communication and sent to a reviewer device 1470. Reviewer device 1470 may then present the identification to a reviewer 1475 and detect input that is indicative of an estimated risk to associate with the abnormality and/or combination.

A result generated by assessment system 1405 can include a quantitative or qualitative (e.g., categorical) risk variable. For example, the risk variable may include a percentage probability or range of getting a particular condition. As another example, the risk variable may include three risk categories (low risk, moderate risk, and high risk).

Assessment system 1405 may generate an electronic report that includes the result and/or that is selected based on the result. For example, different preventative-measure content may be included in reports depending on a risk category. As another example, a report may identify one or more abnormalities (e.g., one or more variants) and/or corresponding normal bases, ranges, data and so on. A report may identify a condition (e.g., disease) pertaining to an analysis (e.g., "Breast Cancer Risk Analysis"). A report may identify types of data (e.g., particular genes and/or other type of data) used in the analysis. A report may identify a confidence in a result (e.g., a risk variable). A report may identify a recommendation (e.g., to consult with a physician or to receive a particular medical test).

Assessment system 1405 may update and may have access to a variety of data stores, part or all of which may be remote from, co-localized with assessment system 1405, and/or included in assessment system 1405. One or more of the data stores may include a relational data store, such that data from one data store or structure within a data store may be used to retrieve corresponding data from another data store or structure. The data stores may include, for example, an account data store 1476, which may include login credentials for one or more users and/or types of data access to be granted to each user; process data store 1477, which may identify laboratory analysis characteristics pertaining to particular data elements (e.g., identifying a laboratory, piece of equipment and/or processing time); genetic data 1478, which may identify one or more genetic sequences associated with a given sample or client; and/or epigenetic data store 1479, which may identify one or more epigenetic sequences or signatures associated with a given sample or client. The data stores may further or alternatively include a results data store 1481, which may identify one or more abnormalities identified by and/or one or more results generated by assessment system 1405 that are associated with a given sample or client; a reports data store 1482, which may include one or more report templates (e.g., each associated with one or more result types) and/or one or more reports to be transmitted or having been transmitted to a client device; and/or a relevance support data store 1483, which may identify which types of data (e.g., genes, genome portions, activity patterns, inputs, medical records, medical tests, etc.) are established to be, potentially, established not to be, or unknown whether to be relevant for evaluating a particular type of risk (e.g., a risk of developing a particular condition).

Genetic assessment network 1400 can also include a user device 1480 configured to detect input from a user 185. User 185 may be associated with an account or other authentication data indicating that access to some or all of the data is to be granted. Accordingly, user 185 may be able to interact with various interfaces (presented at user device 1480) to view data pertaining to one or more particular clients (e.g., in an identified or deidentified manner), to view summary data that relates to data from multiple clients, to explore relationships between data types, and so on. In some instances, an interface may be configured to accept inputs from a user 185 so as to enable the user to request data pertaining to samples with variants in particular genes; particular variants; particular phenotypes or condition risks; ethnicity information; trait information; symptom presence; and/or family-history patterns.

Genetic assessment network 1400 can also include an external assessment device 1490 configured to detect input from a developer 1495. Via such inputs, external assessment device 1490 may send electronic requests for genetic and/or other data (e.g., relating to particular genes, a particular client and/or particular client inputs) to assessment system 1405. An electronic request from an external assessment device 1490 may identify, for example, particular portions of the genome and/or epigenome (e.g., requesting sequences of particular genes and/or identification of any variants or epigenetic modifications detected at the particular genes), family-history data pertaining to one or more identified conditions (e.g., any cancer), and/or medical record data identifying past diagnoses.

In some instances, an interface is configured to identify data types that may be or that are available for at least some subjects or for a particular subject. For example, assessment system 1405 may provide a webpage that accepts queries for genes and ultimately allows a developer 1495 to select particular genes of interest and what data pertaining to the gene is of interest (e.g., a sequence, variant data, epigenetic modification data, and/or categorizations of any variant or epigenetic modification). Similarly, the interface may identify other types of medical-test data, medical-record data, subject input, activity-tracking data, and so on that may be available, such that a developer 1495 may select data of interest. These fields may identify, for example, types of data available for a particular subject (e.g., one having been identified via input from the developer), types of data that the developer is authorized (e.g., generally or upon receiving client approval) to access, or types of data collected for at least one subject in a set of subjects. Thus, one or more interfaces may enable a developer 1495 to specify a semi-arbitrary collection of data of interest.

Assessment system 1405 may evaluate the request to determine, for example, whether a corresponding client 1425 authorized such access (which may be verified via a communication exchange between assessment system 1405 and client device 1430) and/or whether such access is relevant to a purported type of analysis. If the evaluation indicates that access is to be granted, assessment system 1405 may (for example) send an instruction communication to laboratory 1440 to conduct a new analysis of an existing sample, send a data request to a device (e.g., access control device 1460b, client device 1430) and/or retrieve data from a data store (e.g., and extract pertinent information from any larger data structure, such as extracting gene-specific data from a genome). Provision of such data may be conditioned upon or may require payment (e.g., by a client or developer) of a fee.

Various devices in genetic assessment network 1400 may communicate with one or more other devices in genetic assessment network 1400 via a network, such as the Internet, a local-area network or a short-range network. Communications may be sent in a secure manner to, e.g., inhibit unauthorized access to health data. Techniques such as token authentication and/or encryption may be used.

It will be appreciated that the representations of devices and configurations depicted in FIG. 14 are illustrative. For example, while a single laboratory 1440, client device 1430, and genetic data store 1478, etc. are shown, a system may include multiple laboratories 1440, client devices 1430, genet data stores 1478, etc. As another example, while access control devices 1460a, 1460b are shown as being connected to laboratory data store 1455 and EMR data store 1465, additional access control devices may be present in system 1400. For example, an access control device 1405 may be included within or connected to assessment system 1405 so as to control access that requestor device 1410b, client device 1430, distribution device 1435, reviewer device 1470, user device 1480 and/or external assessment device 1490 may achieve.

Figure 15:
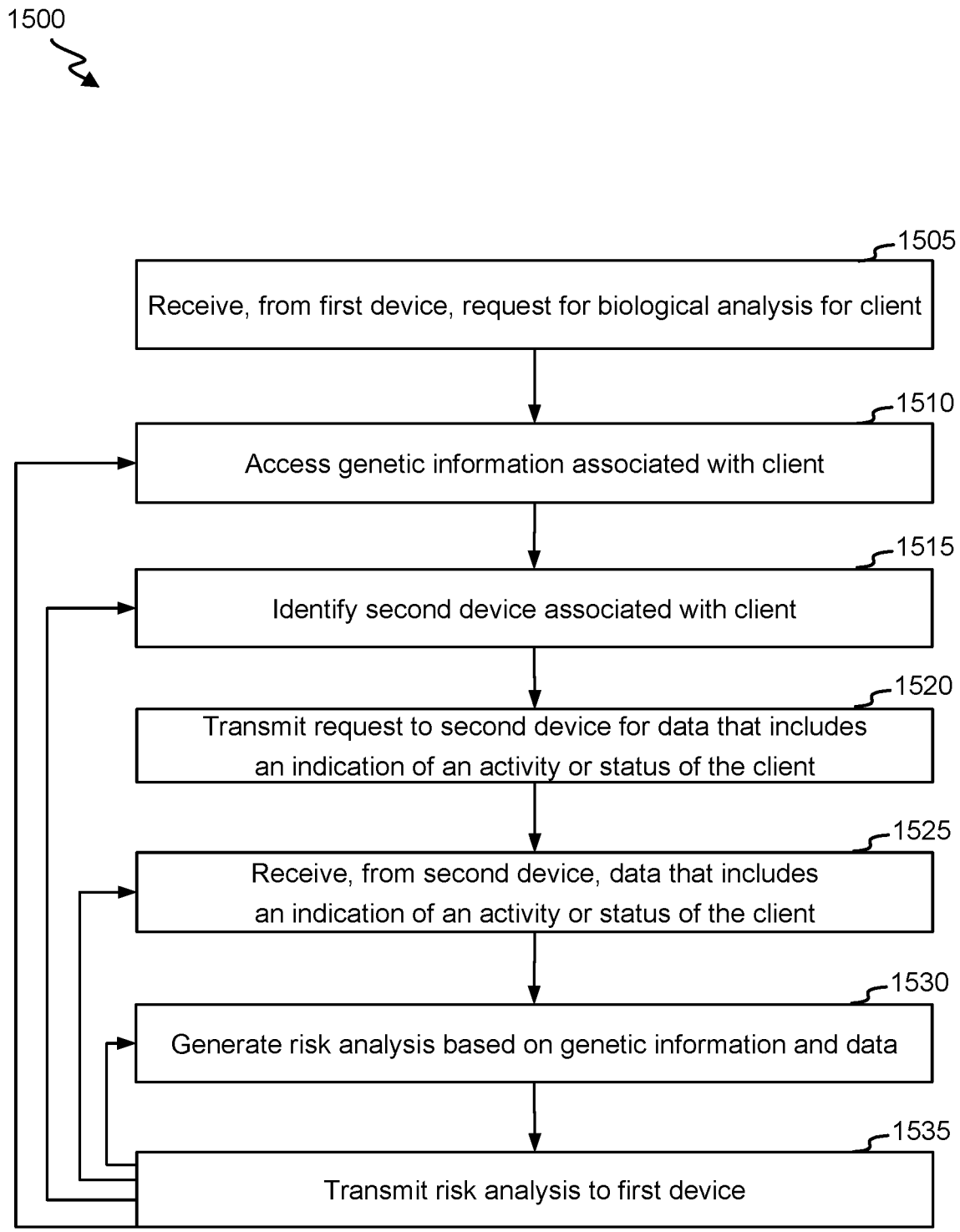
FIG. 15 shows an embodiment of a process for conducting risk analyses based on genetic information.

Referring next to FIG. 15, an embodiment of a process 1500 for conducting risk analyses based on genetic information is shown. Process 1500 may be performed in part or in its entirety by, for example, assessment system 1405. At block 1505, an electronic request is received from a first device for a biological analysis for a client. In one instance, the electronic request includes a preliminary request from a device associated with the client. The preliminary request may have been received via a website and may identify and/or be associated with a condition for which a risk is to be assessed (e.g., a cancer type). For example, the request may include a submission of input on a webpage identifying a type of risk analysis for breast cancer, where the input identifies the client.

In one instance, the electronic request includes, for example, a request (e.g., order) from a device associated with an external or internally linked physician. The electronic request can identify the client (e.g., by name and/or address). The electronic request can identify a condition (e.g., disease) that the biological analysis is to pertain to. For example, the electronic request can indicate that Physician X is ordering a lab-based assessment to be conducted that for Patient Y to determine how much at risk Patient Y is for developing Cancer Z.

At block 1510, genetic information associated with the client is accessed. In one instance, the genetic information is retrieved from a local or remote data store using an identifier of the client. The genetic information may include data provided from a lab device or data provided by an external system controlling the data. The genetic information may identify one or more sequences (e.g., pertaining to each of one or more genes). The genetic information may identify whether one or more variants were detected and/or what variants were detected.

At block 1515, a second electronic device associated with the client is identified. In instances where the request received at block 1505 was from a first device associated with the client, the second electronic device may (but need not) be a different device than the first device. The second electronic device may include, for example, a wearable device, a smart phone or a computer. The electronic device can include, for example, a device that has access to health, activity, or exercise data. In one instance, the second electronic device (or yet another device associated with the client) includes one or more sensors that collect data related to the health, activity or exercise data. For example, the sensors may include an accelerometer and/or gyroscope and/or may be configured to detect movement, location, heart rate and so on. Such sensor data may be processed to estimate, for example, a percentage of the day that the client was exercising, sleeping, sitting, etc.; number of calories burned; and/or heart-rate distribution characteristics. Such statistics may be stored locally at the sensor-including device and/or transmitted to another electronic device associated with the client, such that the statistics may be provided by each of one or both of the devices.

At block 1520, an electronic request for data that includes an indication of an activity or status of the client is transmitted to the second device. For example, the request may be for data including an indication of activity, such as data indicating how many steps a client takes on an average day, a median estimated calorie burn per day, or a mean and standard deviation of nightly sleep hours. As another example, the request may be for data including an indication of status, such as a heart rate status. The data is received from the second device in response to the request at block 1525.

At block 1530, a risk analysis is generated based on the genetic information and data. The risk analysis may be further based on other types of data as well, such as medical record data, medical test data, and/or client inputs. The risk analysis may include a risk variable, such as a risk category.

The risk analysis (e.g., a risk variable) is transmitted to the first device. The risk analysis may be transmitted, for example, as part of an electronic report. The transmission may include sending the risk analysis to an email address or account identifier of the client, such that the risk analysis may be retrieved by the client upon accessing the account or email account.

Process 1500 may, in some instances, return to repeat one or more blocks. Upon such a return, the process may thereafter proceed to repeated each of one or more of the blocks subsequent to the return block. For example, it may be determined that additional genetic information is pertinent to the biological analysis, such that block 1510 is repeated to access the additional genetic data such that it can be evaluated during a repeated generation of the risk analysis. As another example, a new (additional or subsequent) second device associated with the client may be identified (e.g., via provision of client input at a webpage or on a known client device identifying the new device or automated short-range detection of a particular device type, such as a wearable device, at a known client device). Blocks 1515, 1520, 1525 and 1530 may then be repeated to utilize new activity- and/or status-related data made available via the new device. As yet another example, a known second device may provide new data (e.g., that identifies updated or changed activity patterns or recent sleep schedules) via a repetition of block 1525, which may be used to update the risk analysis at block 1530. As still another example, block 1530 may be repeated to generate a risk analysis using existing data but in a different manner (e.g., by applying different weights to data or combining it with additional types of data). In each of these instances, transmission of an updated risk analysis may be performed via a repetition of block 1535 upon, for example, mere generation of the updated risk analysis, detecting a change in the risk analysis (or at least a threshold change), detecting that a defined time period has elapsed since a prior transmission, and so on.

Figure 16:
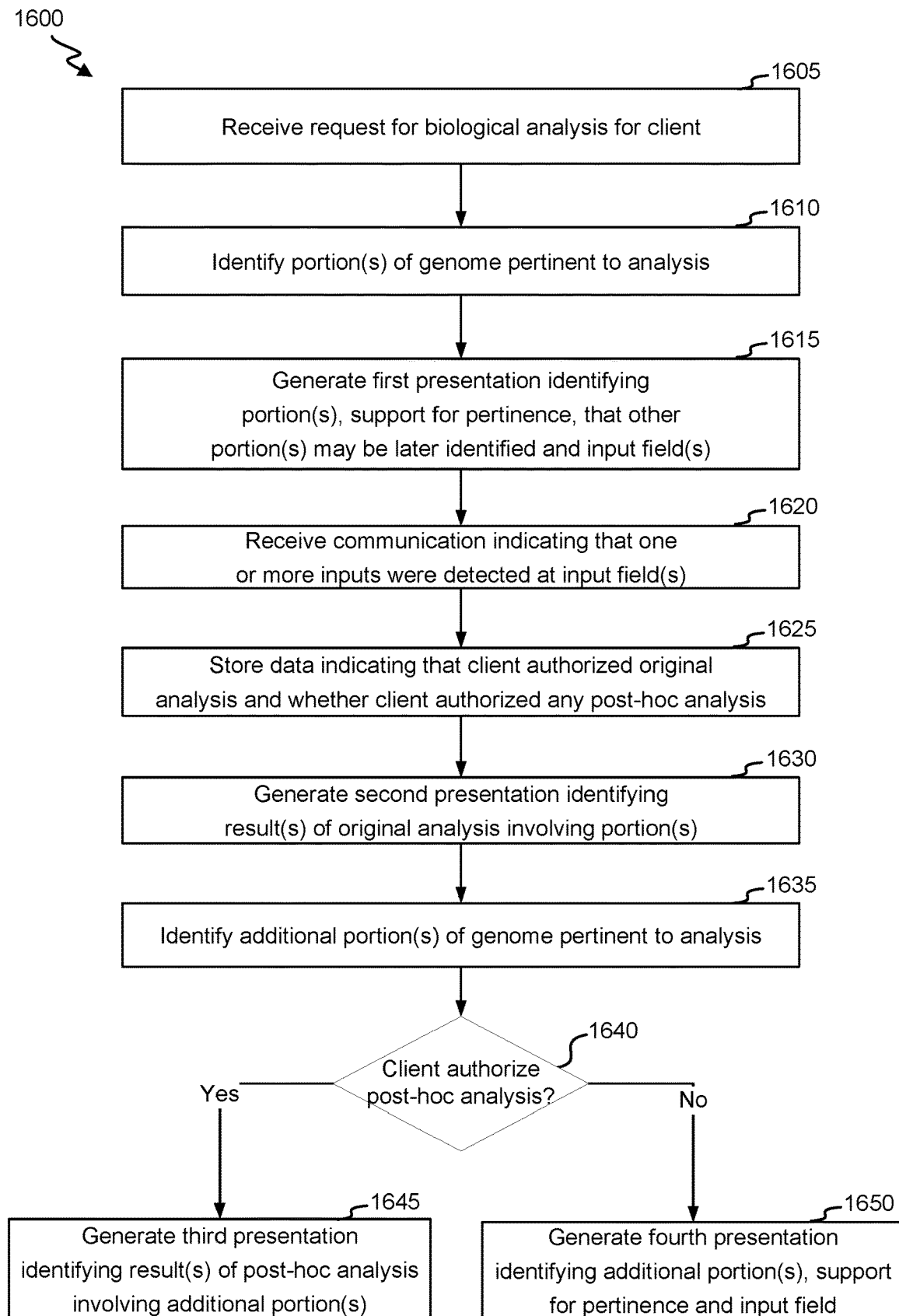
FIG. 16 shows an embodiment of a process for conducting risk analyses based on genetic information.

Referring next to FIG. 16, an embodiment of a process 1600 for conducting risk analyses based on genetic information is shown. Process 1600 may be performed in part or in its entirety by, for example, assessment system 1405. At block 1605, an electronic request is received for a biological analysis for a client. In one instance, the electronic request includes a preliminary request from a device associated with the client. The preliminary request may have been received via a website and may identify and/or be associated with a condition for which a risk is to be assessed (e.g., a cancer type). For example, the request may include a submission of input on a webpage identifying a type of risk analysis for breast cancer, where the input identifies the client.

In one instance, the request may be received from a device associated with an external or internally linked physician. The electronic request can identify the client (e.g., by name and/or address). The electronic request can identify a condition (e.g., disease) that the biological analysis is to pertain to. For example, the electronic request can indicate that Physician X is ordering a lab-based assessment to be conducted that for Patient Y to determine how much at risk Patient Y is for developing Cancer Z.

At block 1610, one or more portions of the human genome pertinent to the analysis are identified (e.g., via a look-up table or rule). The one or more portions may include, for example, one or more genes.

At block 1615, a first presentation is generated that identifies the one or more portions (e.g., by gene name) and that identifies support for contending that the one or more portions are pertinent for conducting the biological analysis. The support may include, for example, citations of and/or links to articles, summaries of published or unpublished data and/or reference to one or more other entities or data stores that associate a given portion with a condition associated with the analysis.

The first presentation further indicates that one or more other portions may later be identified as being relevant to the analysis (e.g., by an entity requested to conduct the analysis and/or other entity). The first presentation further includes one or more input fields. The one or more input fields may include, for example, an accept button that acknowledges terms of conducting an analysis and/or accessing data. In various instances, a single input (e.g., of an accept option) may be indicative of an authorization to conduct an original analysis pertaining to a risk analysis for a condition and to conduct a post-hoc analysis should one or more other portions subsequently be identified as pertaining to a risk analysis for a condition, or one input may authorize an original analysis and another may indicate whether a post-hoc analysis is authorized as well.

The first presentation may be transmitted to a device having transmitted the request received at block 1605 and/or a device of the client. The first presentation may be presented, for example, via a webpage.

At block 1620, a communication is received that indicates that one or more inputs were detected. The one or more inputs may authorize the original analysis and may indicate whether (or that) a post-hoc analysis is authorized.

At block 1625, data indicating that the client authorized an original analysis (e.g., and, in some instances, identifying a type of analysis is stored). For example, data may be stored that includes identifying information about the client and the date that the input-indicating communication was received. In one instance, the one or more input fields in the first presentation are configured such that an authorization is either provided for both the original and for post-hoc analyses or for neither. In such instances, separate indications as to whether a post-hoc analysis was authorized may not be needed. In one instance, the one or more input fields are configured to enable an authorization for an original analysis to be provided and either an authorization or rejection (e.g., via an opt-in or opt-out input) of post-hoc analysis to be provided. The stored data may then reflect whether such post-hoc analysis was authorized.

At block 1630, a second presentation is generated that identifies one or more results of the original analysis identified based on genetic information associated with the portion(s) of the genome. The second presentation may be transmitted to a device having transmitted the request received at block 1605 and/or a device associated with the client. The second presentation may be presented, for example, via a webpage or an email.

At block 1635, one or more additional portions of the genome (e.g., one or more additional genes) are identified as being pertinent to the analysis. Such identification may be a result, for example, of detecting an update in a look-up table or rule.

At block 1640, it is determined whether authorization was provided to perform post-hoc analysis for the client. Such determination may be made by using the data stored at block 1625 (e.g., querying a data store using an identifier of the client). When it is determined that post-hoc analysis was authorized, the additional portion(s) of the client's genome may be accessed, which may involve (for example) retrieving the data from a local data store or a remote data store controlled by assessment system 1405; sending an electronic request with an identifier of the one or more additional portions and the client to another device; and/or facilitating performing a new laboratory analysis on a stored biological sample of the client. The additional portion(s) of the client's genome may then be used to generate one or more results, which may include (for example) an updated risk variable and/or whether (and/or how) a risk variable changed since a previous (e.g., original) analysis. A third presentation is then generated at block 1645 that identifies the one or more results. The third presentation may include a report, may identify the one or more additional portions and/or may identify support for a contention that each of the one or more additional portions pertains to the biological analysis (e.g., via identification of one or more articles). The third presentation may be transmitted to a device having transmitted the request received at block 1605 and/or a device of the client and may be presented at the device via a webpage or email.

When it is determined that post-hoc analysis was not authorized, a fourth presentation is generated at block 1650 that identifies the one or more additional portions and support for a contention that each of the one or more additional portions pertains to the analysis (e.g., by identifying and/or linking to articles). The fourth presentation further includes an input field that may be configured to receive an input indicating that performance of the post-hoc analysis (and/or access to the one or more additional portions) is authorized. The fourth presentation may be transmitted to a device having transmitted the request received at block 1605 and/or a device of the client and may be presented at the device via a webpage or email.

It will be appreciated that, in some instances, a post-hoc analysis need not use an additional portion of the genome. For example, new understandings may indicate how various aspects of a given gene should be processed differently to evaluate a risk of a condition. As another example, a post-hoc analysis may relate to a new condition (e.g., a previously detected variant discovered while investigating a risk for developing a first condition (e.g., cancer) may be uncovered to be informative as to a risk for developing a second condition (e.g., dementia)). As yet another example, a post-hoc analysis may relate to a predicted efficacy of one or more treatments in treating a condition.

Figure 17:
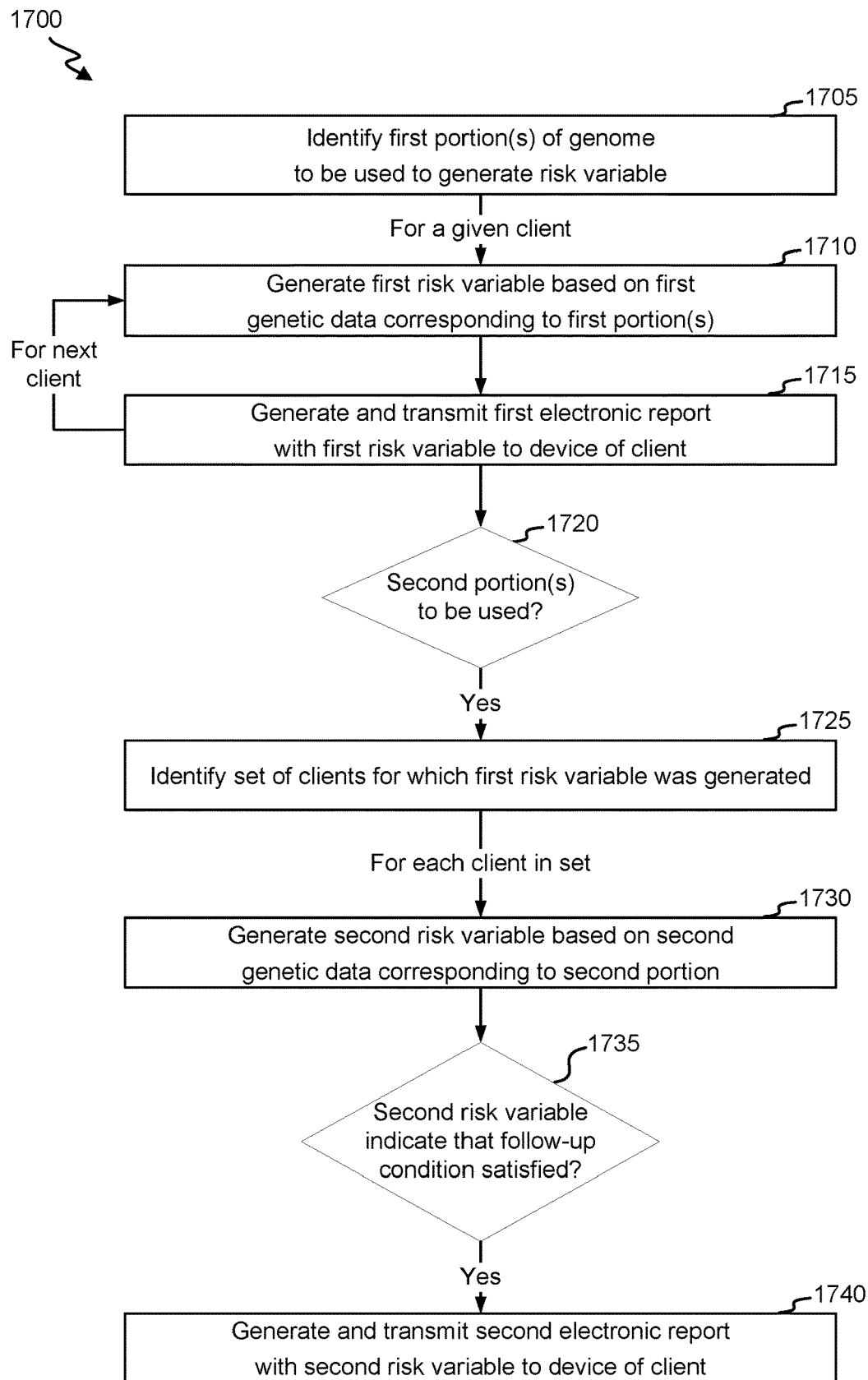
FIG. 17 shows an embodiment of a process for conducting risk analyses based on genetic information.

Referring next to FIG. 17, an embodiment of a process 1700 for conducting risk analyses based on genetic information is shown. Process 1700 may be performed in part or in its entirety by, for example, assessment system 1405. At block 1705, one or more first portions of the genome (e.g., one or more genes) to be used to generate a risk variable (e.g., identifying a predicted likelihood of developing a medical condition or disease) are identified. The one or more first portions may be identified, for example, based on a look-up table or rule.

At block 1710, for a given client, a first risk variable is generated based on first genetic data corresponding to the first portion(s). The client can include one for which a request for conducting the analysis was received and/or for which lab data has been availed (e.g., received from a lab device). At block 1715, a first electronic report that includes the first risk variable is generated and transmitted to a device of the client. Blocks 1710 and 1715 can be repeated for one or more other clients.

At block 1720, it is determined whether one or more second portions have been identified as ones to be used to generate the risk variable. For example, an update in a look-up table or rule may indicate that they are to be used. When it is determined that the one or more second portions are to be used, process 1700 continues to block 1725 where a set of clients are identified. The set of clients can include, for example, a set in which a biological analysis of a particular type (e.g., pertaining to a particular condition or disease) had been conducted for each client in the set and/or each client in the set provided input indicative of an authorization of a post-hoc analysis. Each of blocks 1730-1740 is then performed for each client in the set.

At block 1730, a second risk variable is generated based on second genetic data corresponding to the second portion(s). The second risk variable may also be based on each of one, more or all of the one or more first portions. At block 1735, it is determined, based on the second risk variable, whether a follow-up transmission condition is satisfied. For example, a follow-up transmission condition may be configured to be satisfied when, for a given client, a second risk variable is different than a first risk variable or is different by at least a threshold amount or in a threshold manner (e.g., such that the second risk variable indicates more risk than did the first risk variable).

When it is determined that the follow-up transmission condition is satisfied, at block 1740, a second electronic report is generated to include the second risk variable and transmitted to a device of the client. The second electronic report may indicate that the risk variable had be regenerated and/or identify the first risk variable.

Figure 18:
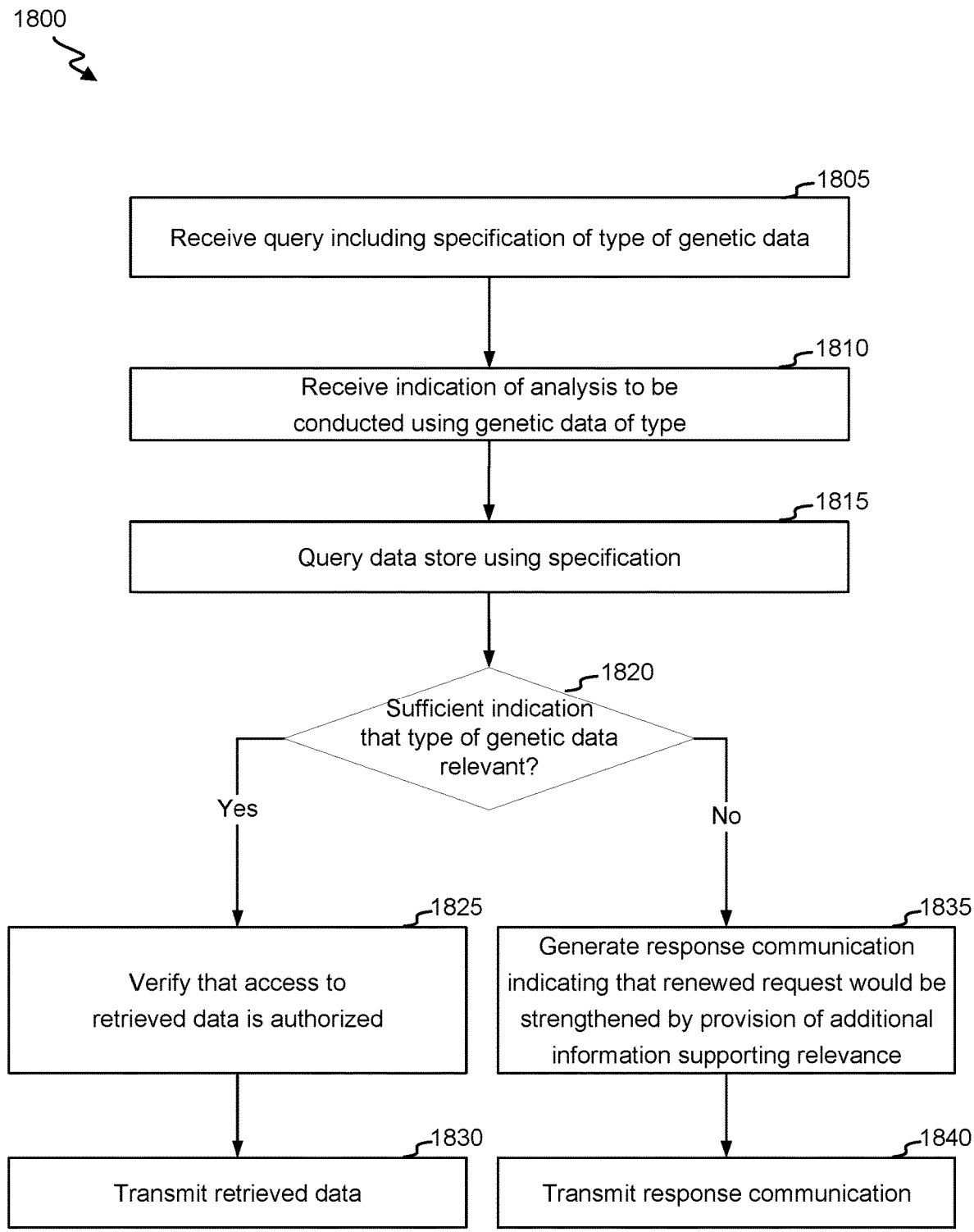
FIG. 18 shows an embodiment of a process for evaluating genetic-data queries based relevance assessments.

FIG. 18 shows an embodiment of a process 1800 for evaluating genetic-data queries based relevance assessments. Process 1800 may be performed in part or in its entirety by, for example, assessment system 1405. At block 1805, a query is received (via an electronic communication) that includes a specification of a type of genetic data. The specification may include an identification, for example, of one or more portions of the genome (e.g., one or more genes). In some instances, the query further identifies a subject (e.g., person) and/or a set of subjects. The query may be received, for example, from a developer device or device with account data indicating that access to genetic data is restricted.

At block 1810, an indication of a type of analysis to be conducted using the genetic data is received. The indication may include, for example, an identification of one or more types of diseases (e.g., one or more types of cancer). Thus, in one instance, blocks 1805 and 1810 include receiving one or more communications that request genetic data (e.g., identifying sequences and/or variants) pertaining to one or more genes for each of one or more subjects such that an analysis can be conducted pertaining to a risk of those subject(s) for developing a particular disease.

At block 1815, a local or remote data store is queried using the specification (e.g., and an identifier of each of the one or more clients).

At block 1820, a determination is made as to whether there is a sufficient indication that the type of genetic data requested via the query is relevant to the analysis identified at block 1810. For example, block 1820 may include determining whether evaluating data pertaining to each of a set of identified genes is informative with regard to a risk of developing a particular cancer. This determination may be made, for example, using a data structure that associates particular genes and conditions and/or via execution of a defined rule.

When it is determined that sufficient indication is available, process 1800 continues to block 1825, where it is verified that access to data retrieved at block 1815 is authorized. When such a verification is made, the data is transmitted at block 1830.

Figure 19:
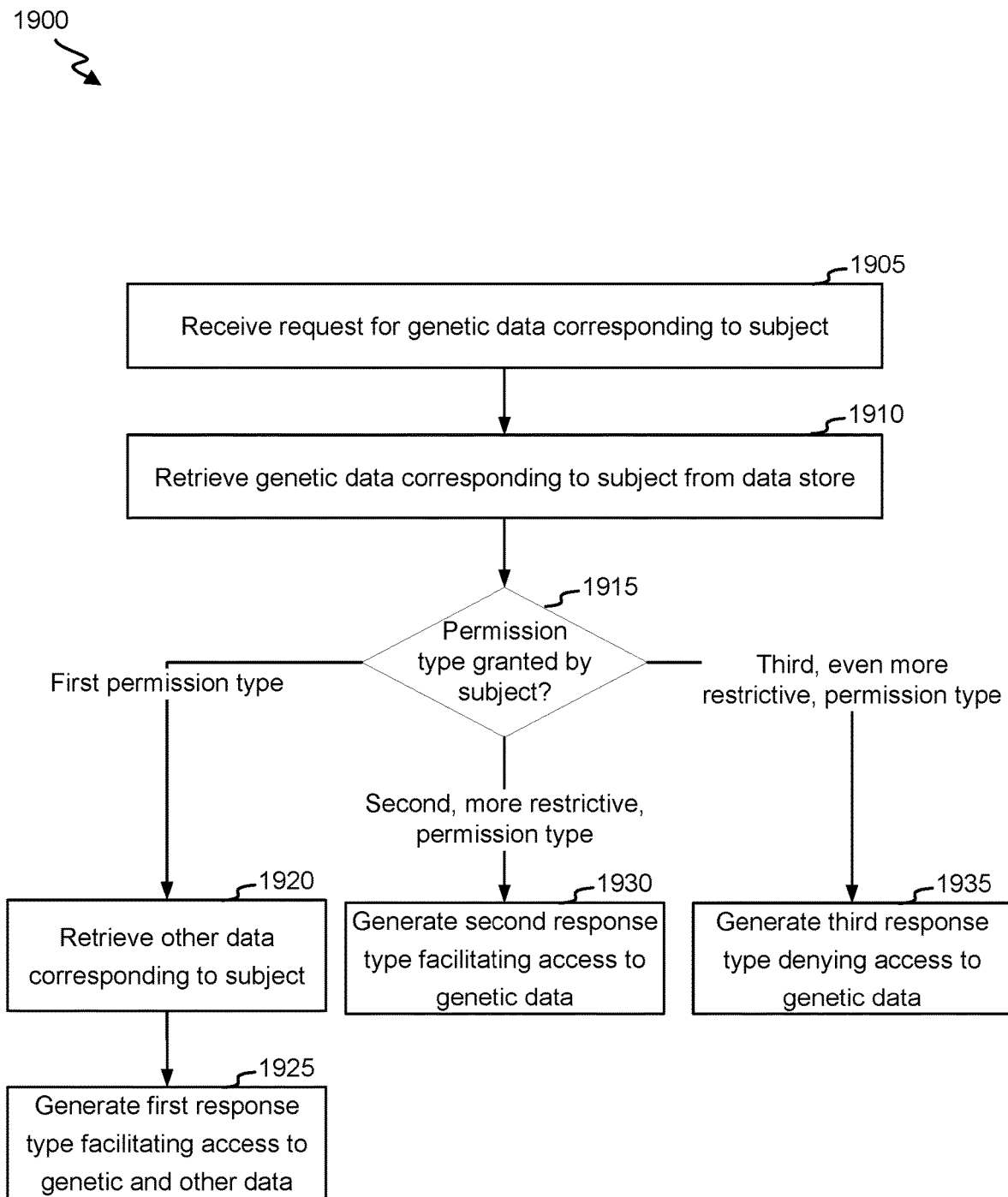
FIG. 19 shows an embodiment of a process for differentially responding to requests for access to genetic data based on subject-provided permission types.

When it is determined that sufficient indication is not available, process 1800 continues to block 1835, where one or more response communications are generated. The one or more response communications can identify that it was determined (as block 1820) that there was not a sufficient indication that the type of genetic data requested via the query is relevant to the identified analysis. The one or more response communications can further indicate that a renewed request for the genetic data would be strengthened by provision of additional information supporting the relevance. The additional information may include, for example, identification of one or more articles or studies and/or provision of unpublished data. The one or more response communications may identify how such additional information may be provided. In one instance, such additional information may be identified even without explicit identification or provision of such from an entity associated with the query. For example, a look-up table and/or rule may be updated in time based on new articles or studies. At block 1805, the response communication is transmitted to a device having transmitted the query, FIG. 19 shows an embodiment of a process 1900 for differentially responding to requests for access to genetic data based on subject-provided permission types. Process 1900 may be performed in part or in its entirety by, for example, assessment system 1405. At block 1905, a request for genetic data corresponding to a subject is received. The request may be received, for example, from a developer device. The request may (in some instances) correspond to or indicate that a whole genome is requested or that one or more particular portions are being requested. The request may identify the subject, for example, by name and/or other identifier (e.g., social security number).

At block 1910, the genetic data corresponding to the data is retrieved from a local or remote data store. The genetic data may include, for example, one or more sequences and/or identification of variants.

At block 1915, a determination is made as to what type of permission type was granted by the subject with regard to data access. The determination may be made, for example, by querying a data store (e.g., a permissions or account data store) or by transmitting a communication to a device of the client to request identification of the permission type (e.g., the communication identifying an entity requesting access) and receiving a corresponding respond.

A first permission type may result in process 1900 proceeding to block 1920, where other data corresponding to the subject is retrieved. The other data may include, for example, responses provided via input to one or more questions via a webpage, medical record data, data from or based on a client device's sensor data indicative of a subject's activity or status, etc. At block 1925, a first response type may be generated that facilitates access to the subject's genetic data and to the other data. For example, a response may include the data or may provide one or more electronic addresses at which some or all of the data can be found.

A second permission type may result in process 1900 proceeding to block 1930, where a second response type is generated that facilitates access to the genetic data. However, the second response type may not facilitate access to the other data (or at least to all of the other data) for which access is facilitated in response to detecting the first permission type.

A third permission type may result in process 1900 proceeding to block 1935, where a third response type is generated that indicates that access to the genetic data is denied.

Figure 20:
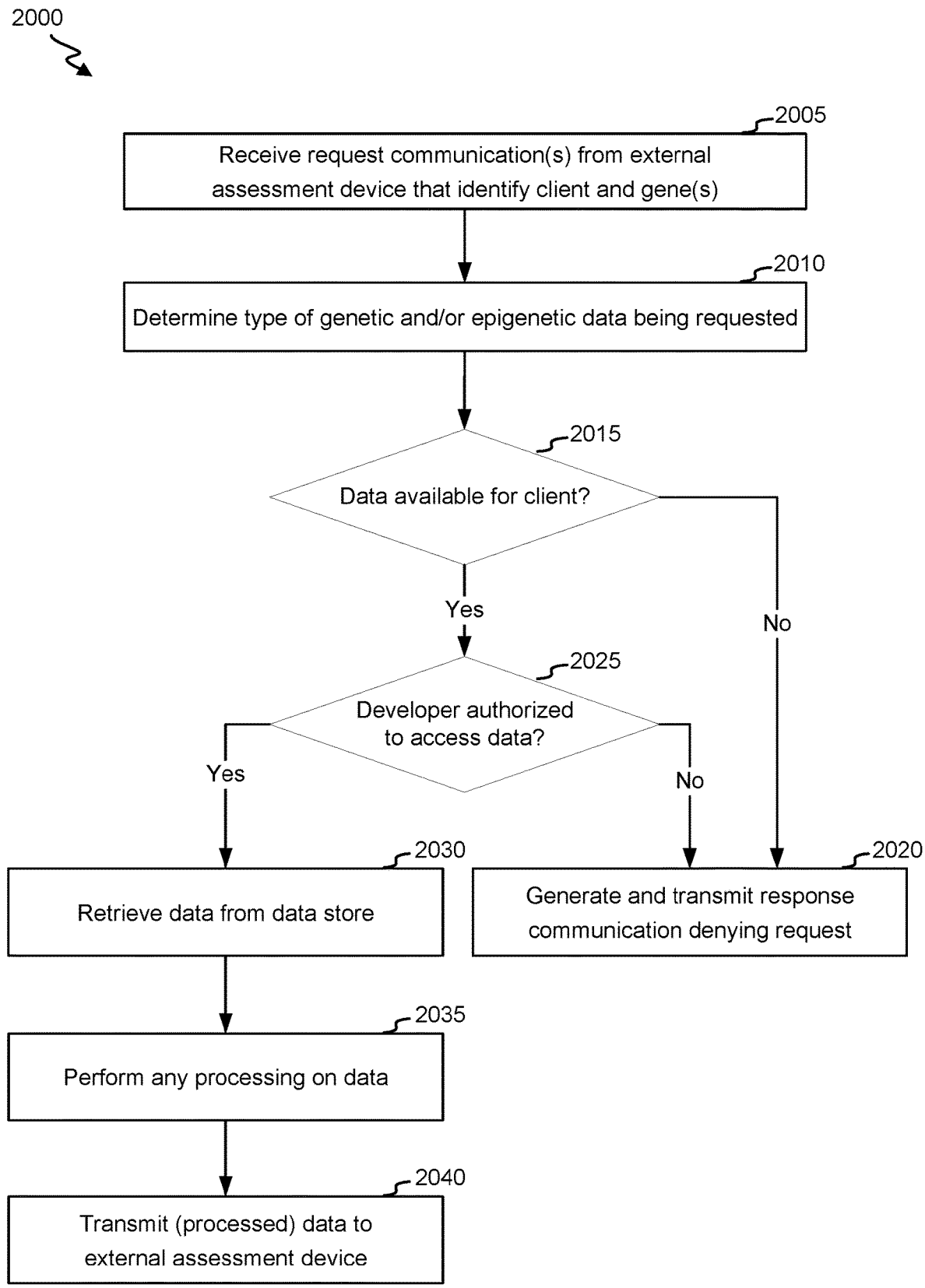
FIG. 20 shows an embodiment of a process for processing custom queries from external assessment devices for genetic and/or epigenetic data.

FIG. 20 shows an embodiment of a process 2000 for processing custom queries from external assessment devices for genetic and/or epigenetic data. Process 2000 may be performed in part or in its entirety by, for example, assessment system 1405. At block 2005, one or more electronic request communications are received from an external assessment device. The one or more request communications can identify a client (e.g., by name, social security number or other identifier) and/or one or more genes (e.g., by name; by specifying a chromosome, chromosome arm, and position on the arm; or molecular address). The external assessment device can include a device associated with (e.g., owned and/or operated by) a developer. The client and/or gene(s) identified in the request communication(s) may correspond to a client and/or gene(s) identified via input from a developer provided at the external assessment device.

At block 2010, one or more types of genetic and/or epigenetic data being requested is determined. The one or more types may be, for example, identified within the request communication(s) (e.g., reflective of developer input), identified via a preference or authorization for a developer, etc. The type of genetic and/or epigenetic data can include, for example, a genetic sequence, an epigenetic sequence, whether (e.g., and where and of what type) a genetic variation was detected, whether (e.g., and where and of what type) an epigenetic modification was detected, a categorization (e.g., pathogenic or benign) of any detected genetic variation, and/or a categorization of any detected epigenetic modification.

At block 2015, it is determined whether data of the requested type for the requested gene(s) and client is or can be available. For example, the determination may involve determining whether the gene(s) had been sequenced for the client, whether a sample remains available for additional sequencing and/or whether processing of existing sequences is possible (e.g., to identify variants).

When it is determined that the data is (e.g., and, in some instances, cannot be) available, process 2000 continues to block 2020 where a response communication denying the request is generated and transmitted to the external assessment device. When it is determined that the data is (e.g., or can be) available, process 2000 continues to block 2025 where it is determined whether a developer associated with the external assessment device is authorized to access the data. The determination may be made, for example, by looking up authorizations associated with the developer and client or by transmitting a communication to a device of the client (e.g., identifying the developer and gene(s)) requesting whether access is authorized and monitoring for a reply.

When it is determined that the developer is not authorized to access data, process 2000 again continues to block 2020 where a response communication denying the request is generated and transmitted to the external assessment device. When it is determined that the developer is authorized to access the data, process 2000 continues to block 2030, where the data is retrieved from a remote or local data store (e.g., by submitting a query that includes an identifier of the client and of the gene(s)).

At block 2035, any processing on the data is performed. For example, processing may include filtering the data to remove information (e.g., client-identifying information). As another example, processing may include transforming the data to be of the requested type of genetic and/or epigenetic data. At block 2040, the retrieved data (or processed version thereof) is transmitted to the external assessment device. For example, the data may be transmitted over a webpage and/or made available via a download.

Substantial variations may be made in accordance with specific requirements. For example, customized hardware might also be used, and/or particular elements might be implemented in hardware, software (including portable software, such as applets, etc.), or both. Further, connection to other access or computing devices such as network input/output devices may be employed.

In the foregoing specification, aspects of the invention are described with reference to specific embodiments thereof, but those skilled in the art will recognize that the invention is not limited thereto. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine- or processor-executable instructions, which may be used to cause a machine or one or more processors to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Where components are described as being configured to perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

While illustrative embodiments of the application have been described in detail herein, it is to be understood that the inventive concepts may be otherwise variously embodied and employed, and that the appended claims are intended to be construed to include such variations, except as limited by the prior art.

We claim:

1. A system for generating communications based on variant information and sensor data, comprising:
    one or more hardware processors; and
    a non-transitory computer readable storage medium in data communication with the one or more hardware processors, the non-transitory computer readable storage medium comprising instructions that, when executed by the one or more hardware processors, cause the one or more hardware processors to perform operations including:
        obtaining, at the one or more hardware processors, genetic-variant data corresponding to one or more variants associated with a client, wherein each of the one or more variants corresponds to an instance of one or more bases positioned at one or more first positions in a first genetic sequence differing from a corresponding one or more bases positioned at corresponding one or more second positions in a reference genetic sequence, wherein the first genetic sequence is a genetic sequence of the client;
        obtaining sensor data providing an indication of a current circumstance of the client;
        processing the genetic-variant data and the sensor data to generate a disease-risk metric corresponding to a predicted risk of the client developing a particular disease;
        generating a communication indicative of the disease-risk metric; and
        transmitting the communication to a remote device.

2. The system for generating communications based on variant information and sensor data as recited in claim 1, wherein the operations further include:
    performing a second disease-risk analysis using the genetic-variant data corresponding to one or more variants, wherein the second disease-risk analysis corresponds to determination of a second disease-risk metric for the client;
    generating a second communication indicative of the second disease-risk metric; and
    transmitting the second communication to the remote device.

3. The system for generating communications based on variant information and sensor data as recited in claim 1, wherein the operations further include:
    identifying an aggregated disease-risk metric for a plurality of other clients different from the client, wherein the communication includes the aggregated disease-risk metric.

4. The system for generating communications based on variant information and sensor data as recited in claim 1, wherein the operations further include:
    generating one or more targets for the client, wherein the one or more targets are associated with changing the disease-risk metric for the client, and wherein the communication includes the one or more targets.

5. The system for generating communications based on variant information and sensor data as recited in claim 4, wherein the operations further include:
    receiving additional sensor data providing an updated indication of an updated quality of the client;
    performing a second disease-risk analysis using the genetic-variant data corresponding to one or more variants, the sensor data, and the additional sensor data, wherein the second disease-risk analysis corresponds to determination of a second disease-risk metric for the client;
    generating a second communication indicative of the second disease-risk metric; and
    transmitting the second communication.

6. The system for generating communications based on variant information and sensor data as recited in claim 1, wherein the operations further include:
    transmitting a request for permission to access the genetic-variant data corresponding to one or more variants associated with the client;
    receiving a response including authorization to access the genetic-variant data corresponding to one or more variants associated with the client; and
    using the authorization in obtaining the genetic-variant data corresponding to one or more variants.

7. The system for generating communications based on variant information and sensor data as recited in claim 1, wherein the sensor data includes one or more of chemical sensor data, potentiometric sensor data, solute sensor data, microfluidic sensor data, biometric sensor data, biomarker sensor data, pH sensor data, cytometric sensor data, optical sensor data, electrical current sensor data, electrical resistance sensor data, and electrical impedance sensor data.

8. The system for generating communications based on variant information and sensor data as recited in claim 1, wherein the sensor data corresponds to sensor data obtained by one or more sensors associated with or worn by the client.

9. The system for generating communications based on variant information and sensor data as recited in claim 1, wherein obtaining the sensor data includes:
  transmitting a query to a second remote device, wherein the query includes a request for the sensor data associated with the client; and
  receiving, in response to the query, the sensor data.

10. The system of claim 1, wherein the operations further include:
  determining, at the one or more hardware processors, that the first genetic sequence includes the one or more variants;
  accessing a work flow for assigning variants to categories, wherein the work flow includes a plurality of stages organized according to a hierarchical structure, and wherein a trajectory through the work flow is determined based on successive results generated for one or more of the plurality of stages;
  for each variant of the one or more variants, performing a work flow iteration by:
    iteratively performing, at the one or more hardware processors, an automated processing in accordance with each of one or more stages of the plurality of stages according to the work flow based on at least one of:
      a position associated with the variant;
      the one or more bases associated with the variant; and
      a result of a previous stage;
      wherein a result of the stage is generated at least partly in response to the automated processing, and wherein a next stage is determined based on the result of the stage;
    wherein performing an automated processing in accordance with a stage of the one or more stages includes:
      performing, at the one or more hardware processors, a look-up function using an identifier of the variant to determine whether stored data indicates that the variant is to be assigned to a specific category of a plurality of categories; and
      generating the result of the iterative performance of the automated processing that identifies the specific category when the stored data indicates that the variant is to be assigned to the specific category; and
    assigning the variant to a category of the plurality of categories based on results of the iterative performance of the automated processing;
  determining whether a number of variants assigned to a particular category of the plurality of categories exceeds a predefined threshold; and
  generating a second communication indicative of whether a number of variants assigned to the particular category exceeds the predefined threshold.

11. The system of claim 1, wherein the operations further include:
  receiving, using the one or more hardware processors, requests from a plurality of client devices for assessing genetic risks associated with a first medical condition, wherein the plurality of client devices are respectively associated with a plurality of clients;
  determining genetic information for each of the plurality of clients, wherein genetic information for a client includes sequence information for a plurality of genes for the client;
  analyzing a first subset of the genetic information to obtain respective genetic risk assessment results for each of the plurality of clients, wherein the respective genetic risk assessment results are associated with the first medical condition;
  making the respective genetic risk assessment results available to the plurality of clients;
  determining a plurality of permissions, each permission corresponding to an authorization provided by a particular client for sharing the sequence information for the plurality of genes for the particular client with one or more external assessment systems, wherein an external assessment system corresponds to a remote system distinct from the one or more hardware processors, and wherein the external assessment system has independent access to a data store including analysis results generated by the external assessment system;
  after determining the plurality of permissions, receiving a data request from a particular external assessment system, wherein the data request corresponds to a request for sequence information for one or more genes for each of the plurality of clients for assessing genetic risks associated with a second medical condition different from the first medical condition, wherein the sequence information for the one or more genes corresponds to a second subset of the genetic information, and wherein the second subset of the genetic information is at least partially different from the first subset of the genetic information;
  determining that an access authorization level for the particular external assessment system is sufficient for accessing the second subset of the genetic information;
  determining that the plurality of permissions authorize sharing the second subset of the genetic information for each of the plurality of clients with external assessment systems;
  obtaining the second subset of the genetic information for each of the plurality of clients and contact information for each of the plurality of clients; and
  transmitting a response to the data request, wherein the response to the data request includes the second subset of the genetic information for each of the plurality of clients and the contact information for each of the plurality of clients, and wherein
    receiving the second subset of the genetic information for each of the plurality of clients at the particular external assessment system facilitates the particular external assessment system generating second respective genetic risk assessment results associated with the second medical condition using the second subset of the genetic information, and
    receiving the contact information for each of the plurality of clients at the particular external assessment system facilitates the particular external assessment system providing the second respective genetic risk assessment results to the plurality of client devices.

12. The system of claim 1, wherein the operations further include:
  for each client of a set of clients:
    receiving, using the one or more hardware processors, a set of reads, each read of the set of reads being associated with the client of the set of clients, each read of the set of reads including a set of identifiers, the set of identifiers being arranged in a particular order in the read;

aligning each read of the set of reads with a portion of a reference data set; and generating a depth vector for the client of the set of clients that includes a plurality of elements, each element of the plurality of elements being generated based on a quantity of reads that include an identifier aligned to a portion that includes a particular position within the reference data set; and performing, using the one or more hardware processors, a transformation processing of the depth vectors to produce a plurality of components, each component of the plurality of components assigned a component order based on an extent to which the component accounts for cross-client differences;

identifying a subset of the plurality of components based on the component order; and for each component in the subset:
  generating, for each client of the set of clients, a weight for the component;
  determining, for each client of the set of clients, that the weight for the component indicates that the client is to be associated with a new variant;
  determining positional data for the new variant based on values in the component; and
  storing, for each client of the set of clients, an association between an identifier of the client of the set of clients and variant data that includes the positional data.

13. A computer implemented method for generating communications based on variant information and sensor data, the method comprising:
  obtaining, at one or more hardware processors, genetic-variant data corresponding to one or more variants associated with a client, wherein each of the one or more variants corresponds to an instance of one or more bases positioned at one or more first positions in a first genetic sequence differing from a corresponding one or more bases positioned at corresponding one or more second positions in a reference genetic sequence, wherein the first genetic sequence is a genetic sequence of the client;
  obtaining sensor data providing an indication of a current circumstance of the client;
  processing the genetic-variant data and the sensor data to generate a disease-risk metric corresponding to a predicted risk of the client developing a particular disease;
  generating a communication indicative of the disease-risk metric; and
  transmitting the communication to a remote device.

14. The method for generating communications based on variant information and sensor data as recited in claim 13, further comprising:
  performing a second disease-risk analysis using the genetic-variant data corresponding to one or more variants, wherein the second disease-risk analysis corresponds to determination of a second disease-risk metric for the client;
  generating a second communication indicative of the second disease-risk metric; and
  transmitting the second communication to the remote device.

15. The method for generating communications based on variant information and sensor data as recited in claim 13, further comprising:
  identifying an aggregated disease-risk metric for a plurality of other clients different from the client, wherein the communication includes the aggregated disease-risk metric.

16. The method for generating communications based on variant information and sensor data as recited in claim 13, further comprising:
  generating one or more targets for the client, wherein the one or more targets are associated with changing the disease-risk metric for the client, and wherein the communication includes the one or more targets.

17. The method for generating communications based on variant information and sensor data as recited in claim 16, further comprising:
  receiving additional sensor data providing an updated indication of an updated quality of the client;
  performing a second disease-risk analysis using the genetic-variant data corresponding to one or more variants, the sensor data, and the additional sensor data, wherein the second disease-risk analysis corresponds to determination of a second disease-risk metric for the client;
  generating a second communication indicative of the second disease-risk metric; and
  transmitting the second communication.

18. The method for generating communications based on variant information and sensor data as recited in claim 13, further comprising:
  transmitting a request for permission to access the genetic-variant data corresponding to one or more variants associated with the client;
  receiving a response including authorization to access the genetic-variant data corresponding to one or more variants associated with the client; and
  using the authorization in obtaining the genetic-variant data corresponding to one or more variants.

19. The method for generating communications based on variant information and sensor data as recited in claim 13, wherein the sensor data includes one or more of chemical sensor data, potentiometric sensor data, solute sensor data, microfluidic sensor data, biometric sensor data, biomarker sensor data, pH sensor data, cytometric sensor data, optical sensor data, electrical current sensor data, electrical resistance sensor data, and electrical impedance sensor data.

20. A non-transitory computer readable storage medium for generating communications based on variant information and sensor data, the non-transitory computer readable storage medium comprising instructions that, when executed by one or more hardware processors, cause the one or more hardware processors to perform operations including:
  obtaining, at one or more hardware processors, genetic-variant data corresponding to one or more variants associated with a client, wherein each of the one or more variants corresponds to an instance of one or more bases positioned at one or more first positions in a first genetic sequence differing from a corresponding one or more bases positioned at corresponding one or more second positions in a reference genetic sequence, wherein the first genetic sequence is a genetic sequence of the client;
  obtaining sensor data providing an indication of a current circumstance of the client;
  processing the genetic-variant data and the sensor data to generate a disease-risk metric corresponding to a predicted risk of the client developing a particular disease;
  generating a communication indicative of the disease-risk metric; and
  transmitting the communication to a remote device.

* * * * *